US012583882B2

(12) United States Patent
Genieser et al.

(10) Patent No.: US 12,583,882 B2
(45) Date of Patent: Mar. 24, 2026

(54) EQUATORIALLY MODIFIED POLYMER LINKED MULTIMERS OF GUANSINE-3', 5'-CYCLIC MONOPHOSPHATES

(71) Applicant: Mireca Medicines GmbH, Tübingen (DE)

(72) Inventors: Hans-Gottfried Genieser, Lemwerder (DE); Frank Schwede, Bremen (DE); Andreas Rentsch, Bremen (DE); Per Ekström, Lund (SE); Valeria Marigo, Modena (IT); Francois Paquet-Durand, Tübingen (DE)

(73) Assignee: Mireca Medicines GmbH, Tübingen (DE)

( * ) Notice: Subject to any disclaimer, the term of this patent is extended or adjusted under 35 U.S.C. 154(b) by 643 days.

(21) Appl. No.: 17/883,398

(22) Filed: Aug. 8, 2022

(65) Prior Publication Data

US 2022/0402964 A1     Dec. 22, 2022

Related U.S. Application Data

(63) Continuation of application No. 16/316,934, filed as application No. PCT/EP2017/066113 on Jun. 29, 2017, now Pat. No. 11,407,781.

(30) Foreign Application Priority Data

Jul. 11, 2016     (EP) .................................... 16178924

(51) Int. Cl.
| | |
|---|---|
| *A61K 31/7068* | (2006.01) |
| *A61P 27/02* | (2006.01) |
| *C07H 19/213* | (2006.01) |
| *C07H 19/23* | (2006.01) |
| *C07H 21/00* | (2006.01) |

(52) U.S. Cl.
CPC ......... *C07H 21/00* (2013.01); *A61K 31/7068* (2013.01); *A61P 27/02* (2018.01); *C07H 19/213* (2013.01); *C07H 19/23* (2013.01)

(58) Field of Classification Search
None
See application file for complete search history.

(56) References Cited

U.S. PATENT DOCUMENTS

| | | |
|---|---|---|
| 5,625,056 A | 4/1997 | Genieser |
| 2011/0014174 A1 | 1/2011 | Mink |
| 2018/0009311 A1 | 1/2018 | Hays |
| 2019/0292214 A1 | 9/2019 | Genieser |

FOREIGN PATENT DOCUMENTS

| | | |
|---|---|---|
| WO | 89/07108 | 8/1989 |

OTHER PUBLICATIONS

Guadagni et al., Progress in Retinal and Eye Research, vol. 48, 2015, pp. 62-81. (Year: 2015).*
Tsai et al., Pharmacology & Therapeutics, vol. 122, 2009, pp. 216-238. (Year: 2009).*
Jäger, R., et al., "Activation of PDE2 and PDE5 by specific GAF ligands: delayed activation of PDE5," British Journal of Pharmacology, 2010, vol. 161, pp. 1645-1660.
Valtcheva, N., et al., "The Commonly Used cGMP-dependent Protein Kinase Type I (cGKI) Inhibitor Rp-8-Br-PET-cGMPS Can Activate cGKI in Vitro and in Intact Cells," Journal of Biological Chemistry, Jan. 2, 2009, vol. 284, No. 1, pp. 556-562.
Wei, J-Y., et al., "Identification of Competitive Antagonists of the Rod Photoreceptor cGMP-Gated Cation Channel: β-Phenyl-1, N2-etheno-Substituted cGMP Analogues as Probes of the cGMP-Binding Site," Biochemistry, 1996, vol. 35, pp. 16815-16823.

* cited by examiner

*Primary Examiner* — Traviss C McIntosh, III
(74) *Attorney, Agent, or Firm* — DUANE MORRIS LLP; Gregory M. Lefkowitz; Brandon A. Chan

(57)     ABSTRACT

Embodiments of the invention are directed to new equatorially modified polymer linked multimers of guanosine-3', 5'-cyclic monophosphate (cGMP) analogues that inhibit the cGMP-signaling system. The invention is also directed to related monomeric compounds, which may serve as monomeric precursors of the multimers, and/or also show itself inhibitory activity and/or impact the inhibitory activity of the related multimers. The invention further relates to the use of such compounds as reagents for signal transduction research and as modulators of cyclic nucleotide-regulated binding proteins and isoenzymes thereof, and as ligands for affinity chromatography, for antibody production or for diagnostic applications, e.g., on chip surfaces.

19 Claims, 3 Drawing Sheets

FIG. 1

*rd1* administration paradigm

Figure 2:
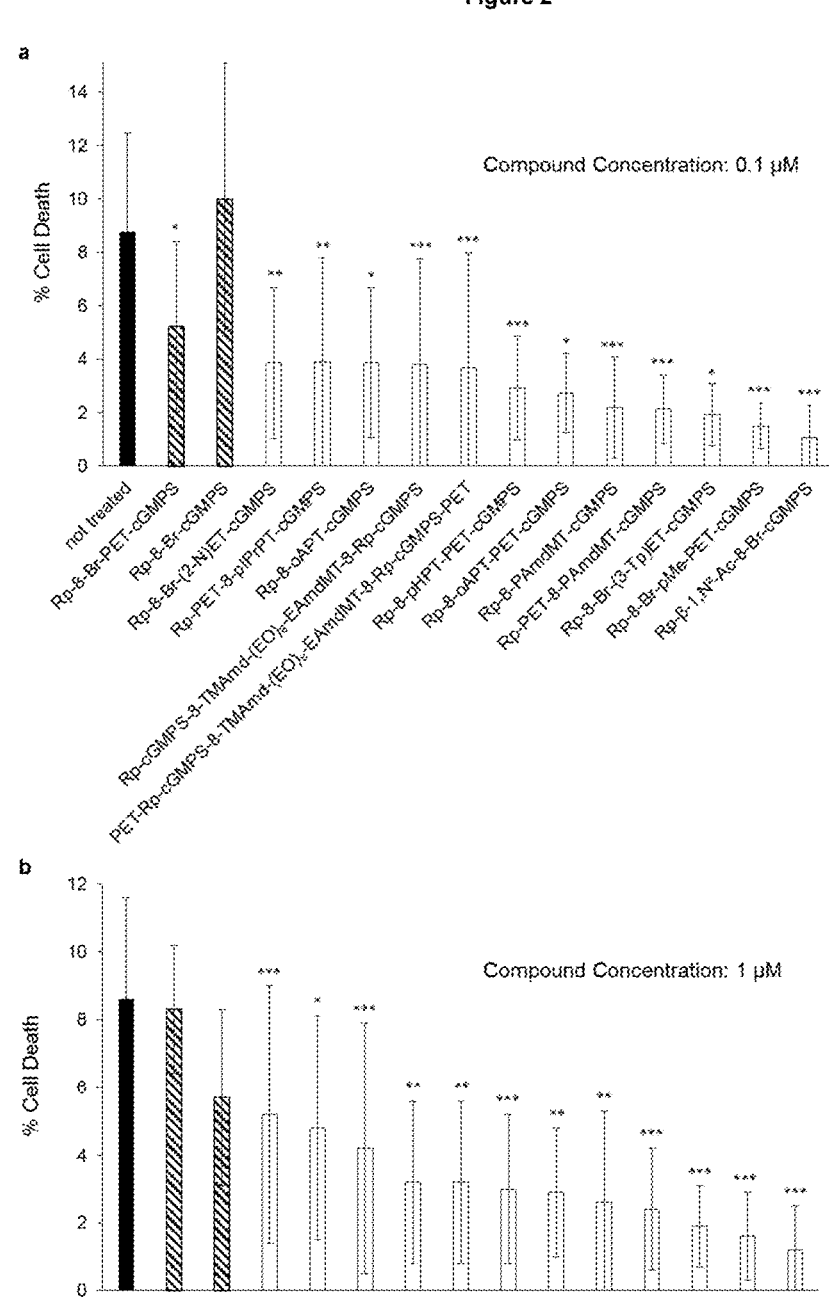

EQUATORIALLY MODIFIED POLYMER LINKED MULTIMERS OF GUANSINE-3', 5'-CYCLIC MONOPHOSPHATES

CROSS-REFERENCE TO RELATED APPLICATIONS

This application claims priority to U.S. patent application Ser. No. 16/316,934, filed on Jan. 10, 2019, which is a 371 national stage entry of International Application No. PCT/EP2017/066113, filed on Jun. 29, 2017, which claims priority to European Patent Application No. 16178924.3, filed on Jul. 11, 2016. The entirety of each of these applications is hereby incorporated by reference for all purposes.

FIELD OF THE INVENTION

The present invention relates to novel equatorially modified polymer linked multimers of guanosine-3', 5'-cyclic nucleotide monophosphates, including tethered di-, tri- and tetramers, and their application in the fields of medicine and pharmacy. The invention also relates to specific precursor monomers. The invention further relates to the use of such compounds as reagents for signal transduction research and as modulators of cyclic nucleotide-regulated binding proteins and isoenzymes thereof, and as ligands for affinity chromatography, for antibody production or for diagnostic applications, e.g., on chip surfaces.

BACKGROUND OF THE INVENTION

Adenosine-3',5'-cyclic monophosphate (cAMP) and guanosine-3',5'-cyclic monophosphate (cGMP) are purine nucleobase-containing cyclic nucleotides and were discovered as endogenous molecules in 1957 and 1963, respectively. They act as second messengers for a multitude of cellular processes, such as gene control, chemotaxis, proliferation, differentiation, and programmed cell death. Several diseases are associated with unusually high or low levels of cGMP and/or cAMP.[1] The syntheses of sulfur-modified Rp-guanosine-3',5'-monophosphorothioate (Rp-cGMPS) and Rp-8-Cl-cGMPS with a sulfur atom introduced into the equatorial exocyclic position of the 3',5'-cyclic phosphate have been described and their inhibitory effect on cGMP-dependent protein kinase (PKG) as a member of the cellular cGMP-system has been reported. However, especially Rp-cGMPS showed a lack of specificity for PKG versus cAMP-dependent protein kinase (PKA), which is inhibited at similar concentrations. Furthermore, insufficient membrane permeability of hydrophilic analogues like Rp-cGMPS and Rp-8-Cl-cGMPS are a major limitation for biological experiments and prohibit a wider application of these analogues. During the last years, a number of Rp-cGMPS analogues, such as Rp-8-Br-cGMPS[2] and Rp-8-Br-PET-cGMPS[2b, 3] with partially improved membrane permeability and biological activity have been developed. These analogues were now at least sufficiently potent to allow for a broader testing of cyclic nucleotide-based inhibitors of the cGMP-system in the biological setting. However, such analogues are still not optimal and sometimes have to be applied in the higher micromolar up to the millimolar range to excert their biological effects. Especially in cells with upregulated cGMP-system either by pharmacological agents or in pathological situations, analogues like Rp-8-Br-PET-cGMPS have demonstrated suboptimal efficacies or even partially ag-onistic properties.[4]

Knowledge on the identity and presence of PKG substrates in different cells, tissues and organ-isms is restricted. Hence the physiological as well as pathological importance of the cGMP-PKG system is not well understood, which is likely to have reduced the general understanding of cGMP-related phenomena, as well as the development of therapies in diseases and conditions where such substrates are involved. If more efficient and reliable cGMP analog-based inhibitors could be developed, these would thus be expected to make it possible to address cGMP-system related questions much more sharply than what can currently be achieved.

Retinal Dystrophies (RD) are severely disabling neurodegenerative diseases of the eye that pro-gressively reduce visual function. These diseases affect rod and/or cone photoreceptors that are the sensory neurons of the retina responsible for converting light stimuli into electro-chemical signals that enable vision. The primary degeneration can affect either rods or cones but often proceeds to complete blindness.

RD is genetically heterogeneous and is linked to more than 250 different genes with different functions and different patterns of expression in the retina. This multitude of target genes ham-pers the development of gene therapy approaches and instead calls for the use of broad, muta-tion-independent neuroprotective therapeutic approaches to target common cell death mechanisms. Published studies provide some information on intracellular mechanisms underlying the degenerative process and have identified some factors playing key roles in photoreceptor cell death. These studies have mostly come from cell and animal models that display gene mutations homologous to RD found in patient cohorts. One such approach uses primary photoreceptors differentiated from retinal stem cells,[5] that when provoked or when originating from RD models, respectively, have been demonstrated to be appropriate models for the characterization of retinal cell death pathways and useful to test small molecules with neuroprotective activities.[6] Another approach involves retinal explants from RD models, which also can be used to study cell death mechanisms and experimental treatment.[4]

The genes mutated in RD are usually associated with photoreceptor specific functions. cGMP plays a direct role in the phototransduction cascade, which takes place within the photoreceptor cells when these are hit by light. In many cases, RD mutations lead to an excessive accumulation of cGMP in photoreceptors,[7] for instance in situations where genes for enzymes involved in photoreceptor cGMP metabolism are affected. Importantly though, photoreceptor accumulation of cGMP can be seen also in situations where the mutated genes have no direct relation to cGMP metabolism,[7] which consequently identifies the cGMP system as a potential target for a muta-tion-independent treatment approach. With respect to genes directly involved in the cGMP metabolism, this is the case for mutations in phosphodiesterase 6 (whose subunits are encoded by genes PDE6B, PDE6A, PDE6G for rod photoreceptors and PDE6C, PDE6H for cone photoreceptors) the photoreceptor enzymes that hydrolyse cGMP to 5'-GMP. The Pde6b gene is mutated in the retinal degeneration 1 (rd1) mouse model of retinitis pigmentosa (RP), which has been well studied in many laboratories. In a supposed chain of events, the accumulation of cGMP in the photoreceptors of the PDE6B mutant retina occurs as a direct consequence of the actual gene defect, and this may thus be seen as an early and mechanistically fundamental degeneration component. In the next step(s), the increased cGMP can be envisaged to have at least one of four targets: 1) PKGs, which when activated by cGMP, will phosphorylate specific proteins, 2) cyclic nucleotide gated ion channels (CNGC), which, when activated by cGMP, allow for a cGMP con-trolled influx of $Na^+$ and $Ca^{2+}$, 3) PDEs, and 4) hyperpolarization-activated cyclic nucleotide-gated (HCN) channels. The first two cGMP targets are directly connected with photoreceptor degeneration,[4, 8] while the cGMP targets PDE and HCN channels may be additionally involved in the degenerative process. Due to their direct connection with early degenerative events, PKG and CNGC can be regarded as disease drivers, even though the downstream mechanisms are still not understood in great detail.[4, 8] It is likely that there may be yet other cGMP targets.

Previously, certain equatorially modified cGMP-derived PKG inhibitors, e.g., Rp-8-Br-cGMPS, Rp-8-Br-PET-cGMPS were found to offer some protection of rd1 and rd2 mutant photoreceptors both in in vitro (rd1 and rd2) and in in vivo (rd1) model system of analyses.[4] The rd2 model car-ries a mutation apparently unrelated to the cGMP sys-tem.[4,7] However, these current state-of-the-art equatorially modified cGMP-analogues have to be applied at high extra-cellular doses to exert any inhibitory effects on the patho-logically imbalanced cGMP-system, thus implying the risk of extracellular or intracellular side effects.

A promising class of compounds, now, has been con-ceived by the inventors to show improved inhibitory effects compared to state of the art compounds Rp-8-Br-cGMPS and Rp-8-Br-PET-cGMPS are equatorially modified (inhibi-tory) polymer linked multimeric cGMP (PLM) analogues, which however have not been synthesized or studied before. A chemically related activatory polymer linked dimeric cGMP (PLD) analogue, without equatorial modification, in turn, was reported to induce significantly increased activa-tion of either PKG Ia or CNGC, depending on the spacer length, when compared to monomeric cGMP[10]. One draw-back of this single related report, however, was the low yielding synthetic linkage strategy[10, 12], which does not give effective access.

There are currently no approved prevention or treatment methods available for RD, and the development of new and improved compounds able to directly interfere with the cell death path-way(s) and prevent photoreceptor demise is needed. It is thus an object of the present invention to provide new equatorially modified cGMP analogues for the inhibition of the cell death pathways activated during the retinal degenerative process. Preferably, to show their effec-tiveness with respect to potential intervention of photore-ceptor cell death, the new equatorially modified cGMP analogues should be effective inhibitors of cell death in primary photoreceptors differentiated from retinal stem cells and in RD-related cells or tissues. It is a further object of the invention to provide new equatorially modified cGMP ana-logues as research tools to identify and vali-date the cGMP-system in other cell lines of neuronal origin and in general cell cultures or tissue systems. In an additional object, the new equatorially modified cGMP analogues should be more effective than Rp-8-Br-cGMPS and Rp-8-Br-PET-cGMPS to inhibit the cGMP-system in cell culture and tissue sys-tems. Another object of the invention is to provide new equatorially modified cGMP analogues for affinity chroma-tography, for antibody production, for diagnostic applica-tions or as additives for transplantation storage solutions for organs or tissues. A further object of the invention is to provide new equatorially modified cGMP analogues for the pharmacological inhibition of disease-related unbalanced cGMP in the medicinal setting also outside of retina and retinal photoreceptors.

Another object of the invention is to establish new equa-torially modified (inhibitory) polymer linked multimeric cGMP analogues while applying more robust and regiose-lective synthetic methods with improved yields, compared to the single related report of an activatory PLD com-pound[10], to give effective access.

SUMMARY OF THE INVENTION

Accordingly, the object of the present invention is solved by providing new equatorially modified (inhibitory) poly-mer linked multimeric cGMP analogues, while also applying more robust and regioselective synthetic methods with improved yields to give effective access to the said new equatorially modified (inhibitory) polymer linked multim-eric cGMP analogues.

In a further aspect, the objects of the invention are achieved by a pharmaceutically acceptable new equatorially modified polymer linked multimeric cGMP (PLM) analogue or a related monomeric precursor thereof, with improved properties compared to state of the art compounds Rp-8-Br-cGMPS and Rp-8-Br-PET-cGMPS for treating or diagnos-ing a pathology, condition or disorder associated with dys-regulation of a cGMP-effected cellular target, wherein preferably the target is, including, but not limited to, at least one of a cGMP-dependent protein kinase (PKG), a hyper-polarization-activated cyclic nucleotide-gated (HCN) chan-nel, a phosphodiesterase (PDE) and a cGMP-gated channel (CNGC). In a further aspect, the objects of the invention are achieved by a new equatorially modified polymer linked multimeric cGMP analogue or a related monomeric precur-sor thereof employed as a suitable research tool to interfere with the cGMP-system in cell cultures or tissues or as a diagnostic tool.

Preferably, the cGMP analogue is a chemically conju-gated multimer of equatorially modified guanosine-3', 5'-cy-clic nucleotide monophosphates, including tethered di-, tri-and tetramers according to formula (I) or formula (II) or a monomeric precursor cGMP-analogue according to formula (III).

BRIEF DESCRIPTION OF THE FIGURES AND FORMULAS

Formula I General constitution of compounds of the invention (branched and linear analogues).

Formula Ib More detailed illustration of Formula I.

Formula II General constitution of compounds of the invention (linear analogues).

Formula IIb More detailed illustration of Formula II.

Formula III General constitution of G units as discrete compounds of the invention or units of compounds accord-ing to Formula I or II.

Formula IV and V General constitution of G units accord-ing to Formula III, featuring exemplary imidazolinone sub-stitution.

Figure 1:
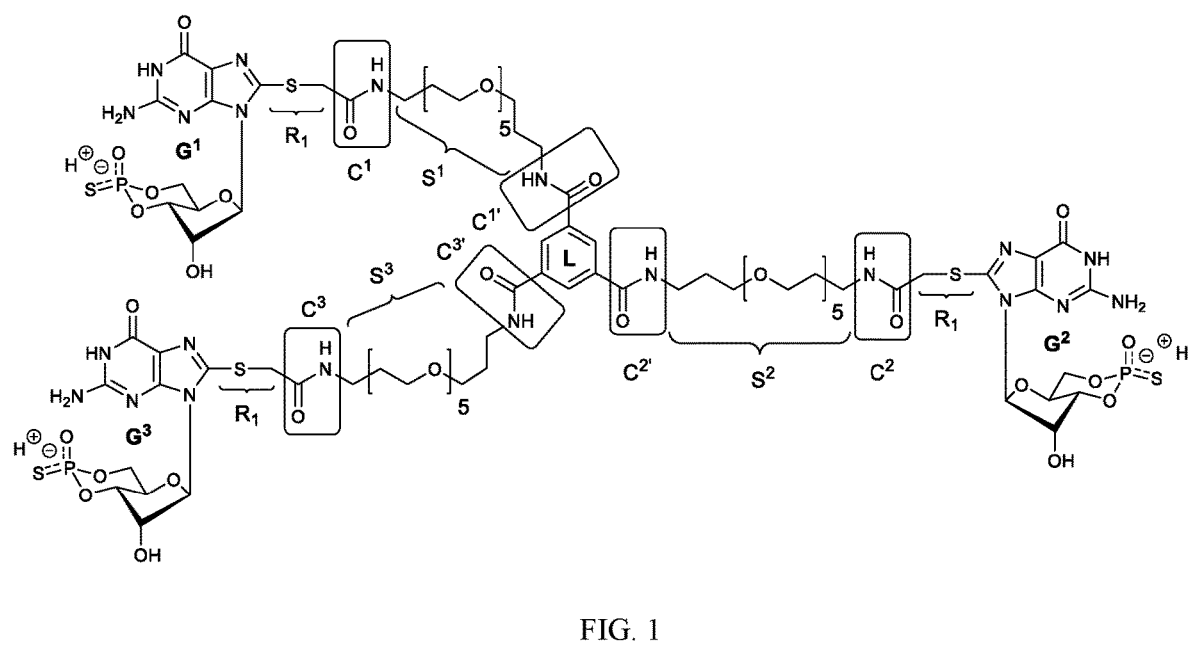

FIG. 1 Example of a trimeric compound according to the invention, illustrating the used variables.

FIG. 2 Protective effect of exemplary compounds of the invention against cell death in primary rod-like cells (com-pared to known compounds Rp-8-Br-cGMPS and Rp-8-Br-PET-cGMPS).

Legend: Primary rod-like cells derived from the rd1 mutant mouse undergo spontaneous cell death 11 days after differentiation. Rod-like cells were exposed to compounds at day 10 of culture and analyzed 24 hours later. A.: 0.1 μM concentration of tested compounds. B.: 1 μM concentration of tested compounds. Percentage of dying cells was evaluated by Ethidium Homodimer assay. Untreated cells are shown as control sample (black bar). Reference compounds Rp-8-Br-cGMPS and Rp-8-Br-PET-cGMPS are shown as dashed bars. Data are shown as means±SD from at least three biological replicates.

Figure 3:
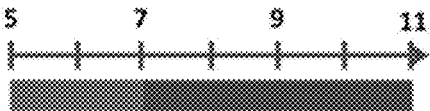

FIG. 3 Culturing paradigm for rd1 explant experiments.

Legend: The animals at the age of postnatal day 5 (PN5) were killed by decapitation and retinas were dissected out with retinal pigment epithelium attached as described previously.[9] The retinas were flattened out on the membranes of commercially available 6-well culture inserts, after which 1.5 ml of a custom made culturing medium was added to each well. These explants were then kept in culture for two days without any treatment after which the test analogue of the invention at the desired concentration was added at a medium change at PN7 ("7" in Figure). There was then a new medium change at PN9 ("9" in Figure), with same concentration of analogue of the invention, upon which the cultures were kept until PN11 ("11" in Figure). At this time point the experiment was finished by a fixation procedure. This paradigm is therefore called PN5+2+4. Controls, i.e. rd1 explants without any treatment, used the same paradigm. Healthy animals (wild type, wt) may be used for comparisons. The lighter part of horizontal bar represents the first period, with no treatment, and the darker part indicates the actual treatment period.

Figure 4:
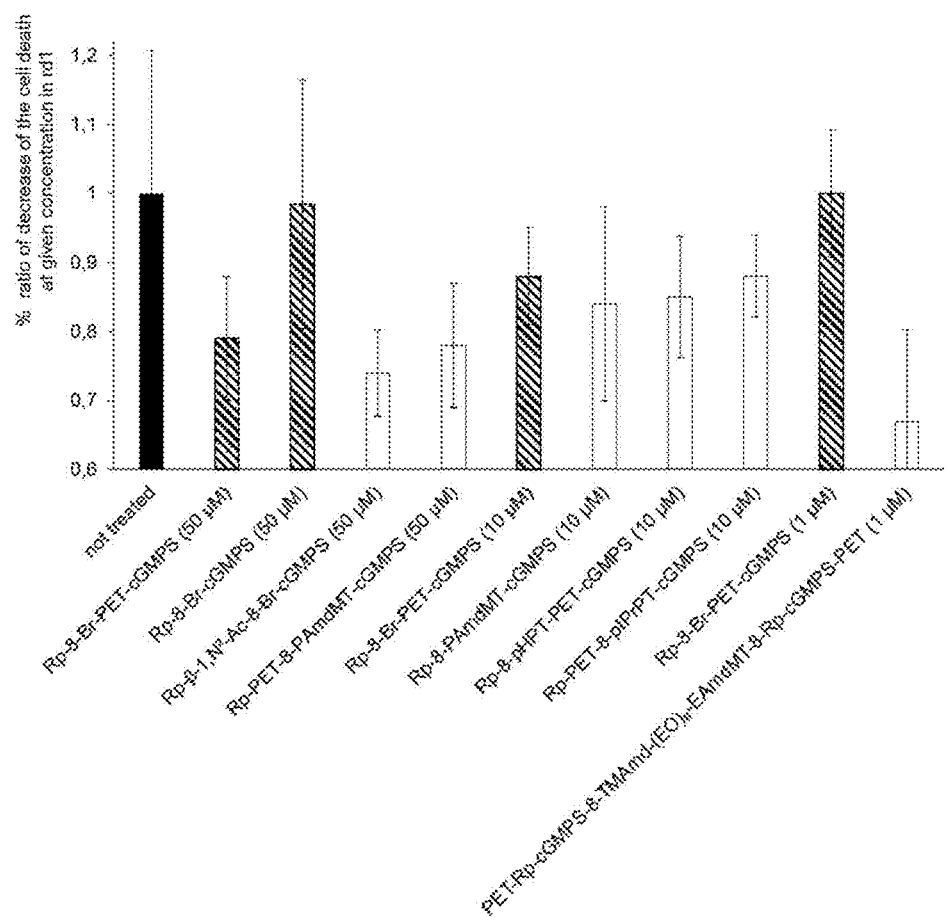

FIG. 4 Protective effects of exemplary compounds of the invention against cell death in retinal explants (compared to known compounds Rp-8-Br-cGMPS and Rp-8-Br-PET-cGMPS).

Legend: Effects of selected analogues at given concentrations of the invention on the cell death of photoreceptors of rd1 explants. The cell death was assessed by so called TUNEL stain on fixated and sectioned material, after which the number of dying cells was counted and analysed, and compared with that from untreated rd1 explants. In order to allow more direct comparisons between the different analogues and concentrations a ratio of treated/untreated specimens was calculated. The left-most bar represents untreated explants as such, which then have the ratio 1.0 since there is no effect. The next bar then concerns Rp-8-Br-PET-cGMPS at 50 μM, where the effect ratio was about 0.78, meaning that this treatment reduced the photoreceptor cell death by more than 20%. The rest of the treatments can be interpreted in the same way. Bars represent standard deviation and the number of tests was 8.

DETAILED DESCRIPTION OF THE INVENTION

The present invention relates to new equatorially modified polymer linked multimeric cGMP (PLM) analogues and related monomeric precursors thereof. Therein the term "equatorially modified" refers to modifications of the equatorial exocyclic position of the 3',5'-cyclic phosphate ($R_8$ in formula III). The present invention has utility as improved pharmacological agents and research tools.

The concept of achieving increased activity by potentially addressing more than one binding site of a target protein simultaneously with a single molecule has been reported once before using an activatory polymer linked dimeric cGMP analogue (PLD), without equatorial modification.[10] Therein a homologous series of one PLD, differing only in the length of the PEG spacer, was synthesized and tested for the ability to activate cGMP-dependent protein kinase Iα (PKG Iα) and cyclic nucleotide-gated ion channels (CNG channels). The results suggested, that PLDs feature an enhanced activatory potential compared to monomeric cGMP, while this enhancement, however, fundamentally depends on an optimum spacer length (between the cGMP units), which is unique for each addressed protein. Thus with increasing deviation from this optimum spacer length the effect was reported to decrease and eventually to disappear.

Based on this work it was proposed, that the inhibitory potency of a known antagonistic cGMP analogue, featuring a phosphorothioate group with Rp-configuration, could also be improved through linkage to a second unit of said analogue via a polymeric spacer.[11] This, however, has never actually been performed. The proposal also did not include a recommendation or evaluation of which position within the molecule would be suitable for the attachment of the linking spacer. It was thus not known at what position the spacer would be tolerated, in order to achieve an increased inhibitory effect in particular for the other PKG isoforms 1B and II, if such an increased inhibitory effect could be obtained at all. Furthermore, there neither was a synthetic protocol for the preparation of such multimeric antagonistic compounds, nor a description of the nature of coupling functions or functionalization of precursors, suitable to perform linkage to further units and/or spacers, apart from the one synthesis that had actually been performed. For said synthesis (of an activatory analogue) cGMP, carrying a thiol-group in the 8-position, was reacted with bifunctional PEG vinylsulphone to furnish a dimer linked via the 8-position.[10-11] A yield for this method was not provided. However, the reported conditions, as published later[12] and in accordance with our own experience, favour addition at the 7-instead of the 8-position. One therefore has to conclude, that the desired dimer linked via the 8-position is only obtained with poor yields using this strategy. More robust and regioselective methods with improved yields were thus needed to give effective access to the inhibitory analogues of such compounds for further exploration.

As described above the potential of PLDs had so far only been studied for a single homologous series of an activatory analogue and its impact on PKG isoform Iα and CNG channels. Other targets of the cGMP signalling cascade such as PKG Iβ and II were not researched in this context. It was thus not known, what modifications would be needed to address these targets.

In a complex cellular system like primary rod-like cells, as used herein as a model for retinal cell death pathways, the cGMP system is dysregulated. Overactivation of more than one cGMP target could therefore provoke cell death. It was not known which cGMP target(s) needed to be addressed to achieve a protective effect. If for instance inhibition of multiple targets was necessary, it was uncertain, whether PLD or PLM analogues in general would be suitable. Previous work only focused on spacer length as modifier to improve and optimize activity of a PLD compound and results suggested a quite selective target affinity, depending on the spacer length. Accordingly, addressing two or more targets with the same PLD, appeared, if feasible at all, only possible with an intermediate spacer length at which the activation potential for both targets would be significantly decreased.

The effect of nucleobase modification (e.g. substituents), variation of the coupling moiety or linkage position, as well as combination of two different cGMP units within a PLM on the activation potential was not addressed before.

Most essential factors related to the concept of using multimeric cGMP analogues to inhibit the cGMP signalling pathway were thus unknown.

When we set out to explore and establish the first compounds of this kind, we first started with the synthetically easier accessible activatory analogues ($R_8$=O, see formula III) and studied their ability to activate PKG isoforms Ia, JR and II. A first set of analogues was coupled via the 8-($R_1$) position. To replace the insufficient coupling strategy of prior art, various more robust, regioselective and higher yielding methods were developed, involving for instance peptide (amid)- and click chemistry. The new PLDs were significantly more active than the one reported in the art.[10] They also essentially maintained their improved activation potential over a rather broad variation of spacer lengths, while all applied new coupling methods gave very similar results. Surprisingly it was further found, that nucleobase manipulation of PLDs and/or variation of the coupling function, which both has not been studied before, overrules the previously proposed target selectivity induced by spacer length. In particular, variations at $R_4$ and/or $R_5$ (such as the β-phenyl-1, $N^2$-etheno (PET) moiety; see formula III) induced very strong PKG Ia activation even at a spacer lengths, where previously no increased activation was observed and the effect was much stronger, than any spacer length related effect. The exchange of the sulfonyl coupling function, which overlaps with modifications of the $R_1$ moiety, also increased PKG activation significantly. Another structural aspect of the new PLDs concerns the linkage position at which the two cGMP analogues are coupled to each other. Thereby the observed activity enhancement of PLDs was not restricted to linkage via the $R_1$ position. It was still present, when linkage was varied along the G unit. Thus, as a non limiting example, PLDs coupled via the PET-moiety (at $R_4$+$R_5$), displayed a similarly increased PKG agonist potential as PET-substituted derivatives tethered via the $R_1$-position. Surprisingly, mixed (heterogenous) PLDs, featuring two unequal G units (e.g. containing one PET-cGMP unit and one that lacks the PET moiety) with different binding affinities would give a PKG (isoform) activation profile, that to a large extend resembles the characteristics of both G units in their corresponding homogenous PLDs. Mixed PLDs that additionally contain mixed linking positions (e.g. PET-cGMP analogue unit linked via the $R_4$+$R_5$—PET-moiety and unit lacking the PET-moiety linked via the $R_1$-position) behaved similarly. These results indicate, that linkage to a second cGMP (analogue) is required to obtain strongly enhanced PKG activity, the second G unit, however, does not necessarily need to be of the same kind. As described, the second G unit can even be a signifanctly less effective activator of PKG (observed for the respective homogenous PLD) while the superior PKG activation of the first G unit (again observed for the respective homogenous PLD) is substantially preserved within the mixed PLD hybrid. These unexpected findings reveal another new great potential of (mixed) PLDs. Established effector compounds often need to be derivatized for specific biochemical applications. For instance, introduction of a fluorescent dye, to enable intracellular localization by means of microscopic or spectroscopic techniques, is a very common strategy. In order to obtain representative results, ideally such transformations, meant to facilitate assay read out, should have no impact on the target activation profile. However, these structural manipulations of the original compound frequently do result in a significant shift of target affinity and specificity or even loss of activation potential. This is especially the case, when the particular moiety can only be introduced at a pharmacophoric group or when it inhibits or weakens binding to the target protein due to steric hindrance. For applications that benefit from the use of multiple target compounds, in turn, a change in (or extension of) the target activation profile obviously can also be desirable. Developing a multi target compound, though, sometimes can be just as difficult as producing a target specific one. This is the case, whenever a modification, needed to address one target, inhibits binding to the second. Mixed PLDs as disclosed within the present invention, provide an improved solution to both of these problems. Their advantage springs from the fact, that two cGMP units (instead of one for monomers) contribute to the overall PKG activation profile. As described above, even such modifications, that would give a completely different target affinity (observed for the monomer or the homogeneous PLD), do not erase the enhanced activation characteristics of the parent compound, as long as they are performed at only one cGMP unit. In this respect, the effect of structural manipulation at a single cGMP unit is buffered within mixed PLDs. Thus, mixed PLDs allow a much broader diversity of modifications (at one cGMP unit), while the undesired decrease of PKG activation, caused by these modifications, is much less pronounced if present at all. On the other hand, mixed PLDs also support the design of multi target compounds. Functional groups (e.g. PET-group), intended to address different targets (e.g. different PKG isoform) apparently can be installed at one cGMP unit, giving an extended target activation spectrum of the mixed PLD.

The concept of polymer linked cGMP analogues was also extended from dimers to tri- and tetramers. Therein linkage of the particular cGMP units is accomplished either in a linear or branched fashion (see formula I and II). The increased number of cGMP units within tri- and tetramers results in even more diverse opportunities to combine (different) activator and target independent functionalized cGMP units. Tested analogues also gave significantly improved PKG activation similar to the dimeric analogues. For more detailed description concerning properties of multimeric activatory cGMP analogues see copending European patent application under file no. 16186700.7.

Accordingly, experiments with the related activatory analogues of the present invention revealed many valuable new properties of multimeric cGMP analogues. It clearly identified the positions R1, R4 and R5 as important modifiers of PKG activation potential, while tolerating rather broad variations, both when used as linkage position and to attach substituents.

This new knowledge was then transferred and tested for inhibitory equatorially modified PLM analogues of the present invention. Given the uncertainties stated above, it was not predictable, that the corresponding dimeric analogues compound 1 and 2 (Table 13) both showed significantly improved potencies to prevent cell death in primary rod-like cells. (FIG. 2), a biological system known to have an activated cGMP-signalling system, compared to state of the art compounds Rp-8-Br-cGMPS and Rp-8-Br-PET-cGMPS. This result is particularly interesting, as it is the first proof of an inhibitory effect caused bei a PLD analogue, and represents a proof of concept supporting the present invention. Furthermore, for the corresponding activatory analogues it was found, that derivatives carrying a substituent at the $R_4$ and/or $R_5$ position, such as the PET-group (as present in compound 2), gave very similar PKG affinities as analogues linked via these positions. This strongly suggests equatorially modified PLM analogues featuring said alternative linkage positions to display similar protective effects. Compound 1 and 2 differ only in terms of the PET-moiety. This moiety in turn induces a quite strong effect on the PKG affinity profile as experienced for the corresponding activators. One therefore needs to conclude, that at least for this testing system, rather broad alterations in the PKG affinity profile and thus substituents, are tolerated. In addition, if both compounds separately give good results, despite their differing PKG affinity profile, a mixed equatorially modified PLD, featuring one cGMP unit with a PET-substituent and one without, according to the inventors educated guess very likely constitute a similarly strong inhibitor as well, following the findings stated above. Also, it seems quite probable, that the concept can be applied to tri- and tetrameric equatorially modified PLMs as well. In order to further improve the protective effects, one focus was to find better substituents at the $R_1$, $R_4$ and/or $R_5$ position. Judging from corresponding activators, these modifiers had a strong impact on target affinity. Therefore numerous analogues featuring said modifications were synthesized and tested at monomeric precursor stage, to select promising candidates.

Surprisingly, all tested compounds of the invention showed significantly improved potencies to prevent cell death in primary rod-like cells (FIG. 2), compared to state of the art compounds Rp-8-Br-cGMPS and Rp-8-Br-PET-cGMPS. The majority was even more effective than the dimeric compounds 1 and 2, making them promising candidates to be transformed into PLM analogues.

As a non limiting example of this matter β-1, $N^2$-acetyl-8-bromoguanosine-3', 5'-cyclic monophosphorothioate (Rp-isomer, compound 21, Table 14) is assembled to the corresponding dimer 3 (Table 13), which displays further improved protective effects in primary rod-like cells.

As another non limiting example of this matter 8-Bromo-(3-thiophen-yl-1, $N^2$-etheno)guanosine-3', 5'-cyclic mono-phosphorothioate (Rp-isomer, compound 23, Table 14) is assembled to the corresponding dimer 20 (Table 13), which displays further improved protective effects in primary rod-like cells.

It was furthermore unexpected, that all tested monomeric and multimeric compounds of the invention produced significantly improved cell survival compared to Rp-8-Br-cGMPS and Rp-8-Br-PET-cGMPS in retinal explants from rd1 mouse, an accepted animal model for RP with pathologically high cGMP-levels and imbalanced cGMP-system in photoreceptor cells (FIG. 4).

It was particularly surprising, that not only monomeric and multimeric compounds of the invention with increased lipophilicities compared to Rp-8-Br-PET-cGMPS, but also those with reduced lipophilicities (Table 17), showed improved protection against cell death in primary photoreceptor cells and explants from rd1 mouse compared to Rp-8-Br-cGMPS.

The new equatorially modified cGMP analogues are compounds of formula (I) or (II)

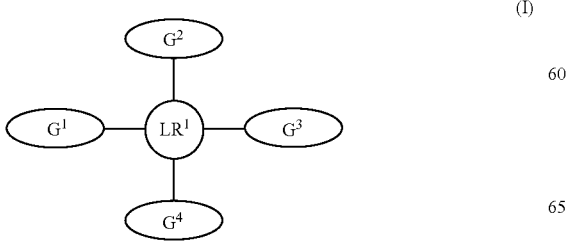

(I)

10

-continued (II)

wherein:

G units $G^1$ and $G^2$ are independently compounds of formula (III) and G units $G^3$ and $G^4$ independently from $G^1$ and $G^2$ and independently from each other are compounds of formula (III) or absent, wherein in case of formula (II) $G^4$ is always absent if $G^3$ is absent, (III)

and wherein in formula (III)

X, Y and Z are N $R_1$, $R_4$, $R_5$, and $R_8$ independently can be equal or individual for each G unit ($G^1$, $G^2$, $G^3$ and $G^4$), while $R_1$ can independently be H, halogen, azido, cyano, acyl, aracyl, nitro, alkyl, aryl, aralkyl, amido-alkyl, amido-aryl, amido-aralkyl, amido-O-alkyl, amido-O-aryl, amido-O-aralkyl, OH, O-alkyl, O-aryl, O-aralkyl, O-acyl, O-aracyl, SH, S-alkyl, S-aryl, S-aralkyl, S-acyl, S-aracyl, S(O)-alkyl, S(O)-aryl, S(O)-aralkyl, S(O)-acyl, S(O)-aracyl, $S(O)_2$-alkyl, $S(O)_2$-aryl, $S(O)_2$-aralkyl, $S(O)_2$-acyl, $S(O)_2$-aracyl, SeH, Se-alkyl, Se-aryl, Se-aralkyl, NR9R10, carbamoylR11R12, NH-carbamoylR11R12, O-carbamoylR11R12, SiR13R14R15 wherein R9, R10, R11, R12, R13, R14, R15 independently from each other can be H, alkyl, aryl, aralkyl;

$R_2$ is absent;

$R_3$ is OH;

$R_4$ can independently be absent, H, amino, alkyl, aralkyl, nitro, N-oxide, or can form together with Y and $R_5$ and the carbon bridging Y and $R_5$ an imidazole ring which can be unsubstituted or substituted with alkyl, aryl or aralkyl, or can form together with Y and $R_5$ and the carbon bridging Y and $R_5$ an imidazolinone as depicted (structure IV, V, n=1) or an homologous ring (n=2 to 8) which each can be unsubstituted or substituted (not depicted) with alkyl, aryl or aralkyl;

11

(IV)

(V)

$R_5$ can independently be H, halogen, azido, cyano, acyl, aracyl, nitro, alkyl, aryl, aralkyl, amido-alkyl, amido-aryl, amido-aralkyl, amido-O-alkyl, amido-O-aryl, amido-O-aralkyl, OH, O-alkyl, O-aryl, O-aralkyl, O-acyl, O-aracyl, SH, S-alkyl, S-aryl, S-aralkyl, S-acyl, S-aracyl, S(O)-alkyl, S(O)-aryl, S(O)-aralkyl, S(O)-acyl, S(O)-aracyl, $S(O)_2$-alkyl, $S(O)_2$-aryl, $S(O)_2$-aralkyl, $S(O)_2$-acyl, $S(O)_2$-aracyl, SeH, Se-alkyl, Se-aryl, Se-aralkyl, NR30R31, carbamoylR32R33, NH-carbamoylR32R33, O-carbamoylR32R33, SiR34R35R36 wherein R30, R31, R32, R33, R34, R35, R36 independently from each other can be H, alkyl, aryl, aralkyl, or can form together with $R_4$, Y and the carbon bridging Y and $R_5$ an imidazole ring which can be unsubstituted or substituted with alkyl, aryl or aralkyl, or can form together with $R_4$, Y and the carbon bridging Y and $R_5$ an imidazolinone ring as depicted (structure IV, V, n=1) or an homologous ring (n=2 to 8) which each can be unsubstituted or substituted (not depicted) with alkyl, aryl or aralkyl;

$R_6$ is OH;

$R_7$ is O;

and $R_8$ is SH, S-alkyl, S-aryl, S-aralkyl, SeH, Se-alkyl, Se-aryl or Se-aralkyl, borano ($BH_3$), methylborano, dimethylborano, cyanoborano ($BH_2CN$), S-PAP, Se-PAP, S-BAP or Se-BAP, wherein PAP is a photo-activatable protecting group with non limiting examples of, optionally, PAP=o-nitro-benzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged) and 6,7-bis (carboxymethoxy)coumarin-4-yl)methyl (BCMCM-caged);

and wherein BAP is a bio-activatable protecting group with non limiting examples of, optionally, BAP=methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, 4-benzoyloxybenzyl;

and wherein linking residues $LR^1$, $LR^2$, $LR^3$ and $LR^4$ independently can replace or covalently bind to any of the particular residues $R_1$, $R_4$ and/or $R_5$ of the G units ($G^{1-4}$) they connect, wherein in case they bind to any of the residues $R_1$, $R_4$ and/or $R_5$, an endstanding group of the particular residue ($R_1$, $R_4$ and/or $R^5$), as defined above, is transformed or replaced in the process of establishing the connection and is then further defined as part of the particular linking residue ($LR^{1-4}$) within the assembled compound, while $LR^1$ is (a) a tri- or tetravalent branched hydrocarbon moiety or (b) a divalent hydrocarbon moiety each with or without incorporated heteroatoms such as, but not limited to, O, N, S, Si, Se, B, wherein the backbone preferably contains 1 to 28 carbon atoms and can be saturated or unsaturated, substituted or unsubstituted, while each attachment point independently can be a substituted or unsubstituted carbon- or heteroatom and in case poly ethylene glycole (PEG) moieties are incorporated in accordance to the definition, the preferred number of carbon atoms can be exceeded by the number present in the PEG moieties, wherein all PEG moieties together can contain a total amount of 1 to 500 ethylene glycol groups ($-(CH_2 CH_2O)_n-$ with n=1 to 500) in case of divalent linking residue ($LR^1$)

or 1 to 750 ethylene glycol groups ($-(CH_2 CH_2O)_n-$ with n=1 to 750) in case of trivalent linking residue ($LR^1$)

or 1 to 1000 ethylene glycol groups ($-(CH_2 CH_2O)_n-$ with n=1 to 1000) in case of tetravalent linking residue ($LR^1$), and, if substituted, substituents include, but are not limited to, optionally one or more alkyl groups, halogen atoms, haloalkyl groups, (un)substituted aryl groups, (un)substituted heteroaryl groups, amino, oxo, nitro, cyano, azido, hydroxy, mercapto, keto, carboxy, carbamoyl, expoxy, methoxy, ethynyl, and/or substituents can further be connected to each other, forming a ringsystem with 1 to 4 rings, with or without incorporated heteroatoms, saturated or unsaturated, substituted or unsubstituted, aliphatic or aromatic;

$LR^2$, $LR^3$ and $LR^4$ are divalent hydrocarbon moieties with or without incorporated heteroatoms such as, but not limited to, optionally heteroatoms O, N, S, Si, Se, B, wherein the backbone preferably contains 1 to 28 carbon atoms and can be, saturated or unsaturated, substituted or unsubstituted, while each attachment point independently can be a substituted or unsubstituted carbon- or heteroatom and in case poly ethylene glycole (PEG) moieties are incorporated in accordance to the definition, the preferred number of carbon atoms can be exceeded by the number present in the PEG moieties, wherein all PEG moieties together can contain a total amount of 1 to 500 ethylene glycol groups ($—(CH_2CH_2O)_n—$ with n=1 to 500)

and, if substituted, substituents include, but are not limited to, optionally one or more alkyl groups, halogen atoms, haloalkyl groups, (un)substituted aryl groups, (un) substituted heteroaryl groups, amino, oxo, nitro, cyano, azido, hydroxy, mercapto, keto, carboxy, carbamoyl, expoxy, methoxy, ethynyl, and/or substituents can further be connected to each other, forming a ringsystem with 1 to 4 rings, with or without incorporated heteroatoms, saturated or unsaturated, substituted or unsubstituted, aliphatic or aromatic;

wherein in case of formula (II) if $G^4$ is absent, $LR^4$ is absent, too, and wherein in case of formula (II) if $G^3$ and $G^4$ are absent, $LR^3$ and $LR^4$ are absent, too, and wherein $G^1$, $G^2$, $G^3$ and $G^4$ can further be salts and/or hydrates while, optionally, non limiting examples of suitable salts of the particular phosphate moiety are lithium, sodium, potassium, calcium, magnesium, zinc or ammonium, and trialkylammonium, dialkylammonium, alkylammonium, e.g., triethylammonium, trimethylammonium, diethylammonium and octylammonium;

and wherein $G^1$, $G^2$, $G^3$ and $G^4$ can optionally be isotopically or radioactively labeled, be PEGylated, immobilized or be labeled with a dye or another reporting group, wherein the reporting group(s) and/or dye(s)

(a) are coupled to $G^1$, $G^2$, $G^3$ and/or $G^4$ via a linking residue ($LR^5$), bound covalently to or replacing any of the particular residues $R_1$, $R_4$ and/or $R_5$ independently for each G unit ($G^1$, $G^2$, $G^3$ and/or $G^4$)

while $LR^5$ can be as defined for $LR^2$ or (b) in case of formula (I) can replace $G^3$ and/or $G^4$ and wherein examples of optionally suitable dyes include, but are not limited to, fluorescent dyes such as fluorescein, anthraniloyl, N-methylanthraniloyl, dansyl or the nitro-benzofurazanyl (NBD) system, rhodamine-based dyes such as Texas Red or TAMRA, cyanine dyes such as Cy™3, Cy™S, Cy™7, EVOblue™10, EVOblue™30, EVOblue™90, EVOblue™100 (EVOblue™-family), the BODIPY™-family, Alexa Fluor™-family, the DY-family, such as DY-547P1, DY-647P1, coumarines, acridines, oxazones, phenalenones, fluorescent proteins such as GFP, BFP and YFP, and near and far infrared dyes and wherein reporting groups optionally include, but are not limited to, quantum dots, biotin and tyro-sylmethyl ester;

and wherein

PEGylated refers to the attachment of a single or multiple $LR^{PEG}$ group(s) independently, wherein $LR^{PEG}$ can be as defined for $LR^2$, with the provisos that in this case (i) of $LR^2$ only one terminus is connected to a G unit ($G^1$, $G^2$, $G^3$ and/or $G^4$) by covalently binding to or replacing any of the particular residues $R_1$, $R_4$ and/or $R_5$ independently for each G unit ($G^1$, $G^2$, $G^3$ and/or $G^4$), and (ii) the other terminus of $LR^2$ is either an alkyl group or a reactive group that allows for conjugation reactions and/or hydrogen bonding while, optionally, non limiting examples of reactive groups are, $—NH_2$, $—SH$, $—OH$, $—COOH$, $—N_3$, $—NHS$-ester, halogen group, epoxide, ethynyl, allyl and with the proviso (iii) that $LR^{PEG}$ has incorporated ethylene glycol moieties ($—(CH_2CH_2O)_n—$ with n=2 to 500).

Chemical Definitions

Listed below are the definitions of various terms and phrases used to describe the compounds of the present invention. These definitions apply to the terms as they are used throughout the specification.

Halogen refers to F, Cl, Br, and I.

Alkyl refers to an alkyl group, which is a hydrocarbon moiety with 1 to 28, preferably 1 to 20 carbon atoms, with or without (integrated) heteroatoms such as but not limited to O, S, Si, N, Se, B, wherein the point of attachment unless specified otherwise is a carbon atom. Its constitution can be Linear saturated hydrocarbon moiety—including, but not limited to, methyl, ethyl, propyl, butyl and pentyl or Linear unsaturated hydrocarbon moiety—containing more preferably 2 to 20 carbon atoms, including, but not limited to, ethylen, propylen, butylen and pentylen or Branched saturated hydrocarbon moiety—deviating from the general alkyl definition by containing at least 3 carbon atoms and including, but not limited to, isopropyl, sec-butyl and tert.-butyl or Branched unsaturated hydrocarbon moiety—deviating from the general alkyl definition by containing at least 3 carbon atoms and including, but not limited to, isopropenyl, isobutenyl, isopentenyl and 4-methyl-3-pentenyl or Cyclic saturated hydrocarbon moiety—containing more preferably 3 to 8 ring atoms and including, but not limited to, cyclopentyl, cyclohexyl, cycloheptyl, piperidino, piperazino or Cyclic unsaturated hydrocarbon moiety—containing more preferably 3 to 8 ring atoms.

Herein the term saturated means the group has no carbon-carbon double and no carbon-carbon triple bonds. However, in the substituted case of saturated groups one or more carbon-oxygen or carbon-nitrogen double bonds may be present, which may occur as part of keto-enol and imine-enamine tautomerisation respectively. Independent from its constitution, an alkyl group, as defined herein, can be substituted or unsubstituted. Substituents include, but are not limited to, one or more alkyl groups, halogen atoms, haloalkyl groups, (un)substituted aryl groups, (un)substituted heteroaryl groups, amino, oxo, nitro, cyano, azido, hydroxy, mercapto, keto, carboxy, carbamoyl, expoxy, methoxy, ethynyl. In case alkyl, as defined herein, contains a poly ethylene glycol (PEG) moiety, the preferred number of carbon atoms can be exceeded by the number present in the PEG moiety, wherein the PEG moiety can contain a total amount of 1 to 500 ethylene glycol groups ($-(CH_2CH_2O)_n-$ with n=1 to 500).

It has to be noted, that $-(EO)_n-$ is used as an abbreviated expression for $-(CH_2CH_2O)_n-$ with n indicating the number of ethylene glycol groups. The number of ethylene glycol groups especially may be n=1-500 or as stated in the particular example.

Aralkyl refers to an alkyl group as described above, that connects to an unsubstituted or substituted aromatic or heteroaromatic hydrocarbon moiety, consisting of one or more aromatic or heteroaromatic rings with 3-8 ring atoms each. Substituents for both the alkyl and aryl part include, but are not limited to, one or more halogen atoms, alkyl or haloalkyl groups, substituted or unsubstituted aryl groups, substituted or unsubstituted heteroaryl groups, amino, nitro, cyano, hydroxy, mercapto, carboxy, azido, methoxy, methylthio.

Aryl refers to an aryl group, which is an unsubstituted or substituted aromatic or heteroaromatic hydrocarbon moiety, consisting of one or more aromatic or heteroaromatic rings with 3-8 ring atoms each. Substituents include, but are not limited to, one or more halogen atoms, haloalkyl groups, substituted or unsubstituted aryl groups, substituted or unsubstituted heteroaryl groups, amino, nitro, cyano, hydroxy, mercapto, carboxy, azido, methoxy, methylthio.

Acyl refers to a $-C(O)$-alkyl group, wherein the alkyl group is as defined above.

Aracyl refers to a $-C(O)$-aryl group, wherein the aryl group is as defined above.

Carbamoyl refers to a $-C(O)-NH_2$ group, wherein the hydrogens can independently from each other be substituted with an alkyl group, aryl group or aralkyl group, wherein alkyl group, aryl group or aralkyl group are as defined above.

O-acyl refers to an $-O-C(O)$-alkyl group, wherein the alkyl group is as defined above.

O-alkyl refers to an alkyl group, which is bound through an O-linkage, wherein the alkyl group is as defined above.

O-aracyl refers to a $-O-C(O)$-aryl group, wherein the aryl group is as defined above.

O-aralkyl refers to an aralkyl group, which is bound through an O-linkage, wherein the aralkyl group is as defined above.

O-aryl refers to an aryl group, which is bound through an O-linkage, wherein the aryl group is as defined above.

O-carbamoyl refers to a carbamoyl group, which is bound through an O-linkage, wherein the carbamoyl group is as defined above.

S-alkyl refers to an alkyl group, which is bound through a S-linkage, wherein the alkyl group is as defined above.

S-aryl refers to an aryl group, which is bound through a S-linkage, wherein the aryl group is as defined above. S-aralkyl refers to an aralkyl group, which is bound through a S-linkage, wherein the aralkyl group is as defined above.

S-aralkyl refers to an aralkyl group, which is bound through an S-linkage, wherein the aralkyl group is as defined above.

Se-alkyl refers to an alkyl group, which is bound through a Se-linkage, wherein the alkyl group is as defined above. Se-aryl refers to an aryl group, which is bound through a Se-linkage, wherein the aryl group is as defined above.

Se-aralkyl refers to an aralkyl group, which is bound through a Se-linkage, wherein the aralkyl group is as defined above. NH-alkyl and N-bisalkyl refer to alkyl groups, which are bound through an N linkage, wherein the alkyl groups are as defined above.

NH-aryl and N-bisaryl refer to aryl groups, which are bound through an N linkage, wherein the aryl groups are as defined above.

NH-carbamoyl refers to a carbamoyl group, which is bound through an N-linkage, wherein the carbamoyl group is as defined above.

Amido-alkyl refers to an alkyl group, which is bound through a $NH-C(O)-$ linkage, wherein the alkyl group is as defined above.

Amido-aryl refers to an aryl group, which is bound through a $NH-C(O)-$ linkage, wherein the aryl group is as defined above.

Amido-aralkyl refers to an aralkyl group, which is bound through a $NH-C(O)-$ linkage, wherein the aralkyl group is as defined above.

Endstanding group refers to a group of a particular residue ($R_1$, $R_4$ and/or $R_5$) which is (sterically) accessible and capable for covalently binding to a particular linking residue ($LR^{1-4}$). This may be a group at the actual terminal end of the residue ($R_1$, $R_4$ and/or $R_5$) or at any terminal end of any sidechain of the residue ($R_1$, $R_4$ and/or $R_5$), or which is otherwise located in the residue ($R_1$, $R_4$ and/or $R_5$) and sufficiently (sterically) accessible and capable for covalently binding to a particular linking residue ($LR^1$-4). The definition of the term endstanding group, if applicable, is independently also valid for the residues $LR^5$ and/or $LR^{PEG}$. Further, the term terminus refers to an endtsanding which is actually a terminal end of the concerned residue.

The person skilled in the art is well aware that a particular linking residue ($LR^{1-4}$) may represent a radical depending on the number of particular G units it binds to. Thus, in compounds of formula (II), the particular linking residue ($LR^{1-4}$) may be a biradical, or in case it is (intermediary) bound to only one particular G unit it may be a monoradical. Similarly, in case of compounds formula (I), depending on the number of particular G units it binds to, the particular linking residue ($LR^1$) may be a biradical, triradical, or tetraradical, or in case it is (intermediary) bound to only one particular G unit it may be a monoradical.

If an otherwise considered monovalent group is used with the modifier "divalent" as in "divalent alkyl" then this adds a second attachment point. Non limiting examples of divalent alkyl would be $-CH_2-$, $-CH_2CH_2-$, $-CH_2C(CH_3)_2CH_2-$.

Whenever side chains or residues are depicted as "floating groups" on a ring system, for example, in the formula:

then these side chains (or residues) may replace any hydrogen atom attached to any of the ring atoms, including depicted, implied, or expressly defined hydrogen, as long as a stable structure is formed. All resulting substitution patterns are thus included. For the given example, this corresponds to The person skilled in the art understands that many compounds that fall under formula III as defined above have tautomeric forms. It has to be noted that according to this specification all tautomeric forms fall under formula III if at least one of the tautomers falls under formula III as defined above.

In the chair form of saturated six-membered rings, bonds to ring atoms, and the molecular entities attached to such bonds, are termed "axial" or "equatorial" according to whether they are located about the periphery of the ring ("equatorial"), or whether they are orientated above or below the approximate plane of the ring ("axial"). Due to the given stereochemistry of the cyclic phosphate ring, the axial position can only be above the approximate plane of the ring.

In naturally occurring cyclic nucleotide monophosphates (cNMP), both R7 and R8 are oxygen, and the phosphorus double bond is "distributed or dislocated" between both atoms. In water at physiological pH, the compound has a negative charge between both oxygens, and a corresponding cation, such as H+ or Na+. Compounds of the present invention have the equatorial (R8) oxygen replaced by a different function, e.g., sulphur, while the axial (R7) oxygen can optionally be replaced too. Irrespective of the nature of the newly introduced R7 and/or R8, the corresponding compound structures herein are presented as charged compounds with a dislocated double bond at the phosphorus, as long as this is in accordance with valency rules. This style is chosen to account for, depict and disclose all possible "locations" of the phosphorous double bond and distribution of electron density or charge each within a single structure. The dislocated double bond, as used herein, depending on the nature of the particular R7 and R8, however, does not necessarily refer to an equally distributed charge or electron density between R7 and R8.

If R7 and R8 are not equal the phosphorus atom has four different ligands and becomes chiral resulting in two stereoisomeric forms. To describe the configuration of the chiral phosphorus, the Rp/Sp-nomenclature is used. Therein R/S follows the Cahn-Ingold-Prelog rules while "p" stands for phosphorus.

To give an example: if the equatorial residue $R_8$ is sulphur (while axial $R_7$ is oxygen), the corresponding cyclic guanosine-3', 5'-monophosphorothioate compound (cGMPS-analogue) is Rp-configurated at phosphorus, if the equatorial residue $R_8$ is a borano group, the corresponding cyclic guanosine-3', 5'-monoboranophosphate compound (cGMPB-analog) is Sp-configurated at phosphorus.

The person skilled in the art knows that for the use in the field of the medicine especially as part of medicaments certainly only physiologically acceptable salts of the compounds according to the invention may be used.

FURTHER SPECIFICATION OF STRUCTURES

In an embodiment the invention relates to a compound according to the definition hereinabove, wherein in case of formula (I) $G^4$ is absent, or, wherein in case of formula (II) $G^4$ and $LR^4$ are absent.

In another embodiment the invention relates to a compound according to the definition hereinabove, wherein in case of formula (I) $G^3$ and $G^4$ are absent, or, wherein in case of formula (II) $G^3$, $G^4$, $LR^3$ and $LR^4$ are absent.

In a further embodiment the invention relates to a compound according to the definition hereinabove, wherein in case of formula (I) $G^2$, $G^3$, $G^4$ and $LR^1$ are absent, or, wherein in case of formula (II) $G^2$, $G^3$, $G^4$, $LR^2$, $LR^3$ and $LR^4$ are absent. In this case the embodiment represent a compound which is a precursor of the multimers of the invention.

In an embodiment the invention relates to a compound according to any definition hereinabove, wherein all $R_8$ are SH.

According to the invention it is preferred, that linking residues $LR^1$, $LR^2$, $LR^3$ and $LR^4$ are further subdivided as depicted in formula (Ib) and (IIb), (Ib)
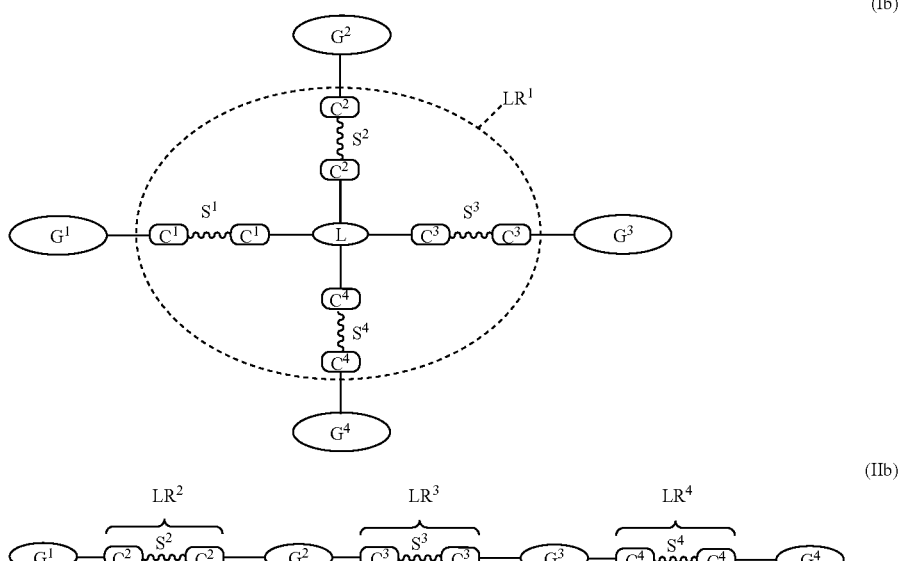
(IIb)
wherein:
coupling functions $C^1$, $C^{1'}$, $C^2$, $C^{2'}$, $C^3$, $C^{3'}$, $C^4$ and $C^{4'}$ independently from each other can be absent or as defined by structures selected from the group consisting of
-continued
$X_3 = NH, O, S$
$X_3 = NH, O, S$
$X = O, S,$
$NH, S(O),$
$S(O)_2, CH_2,$
$C(O)$

21

-continued

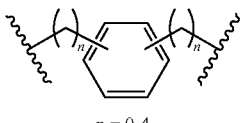

while connectivity can be as depicted or reversed as exemplified by $G^1$-O—C(O)—NH—$S^2$ versus $G^1$-NH—C(O)—O—$S^2$ and wherein in case the coupling function ($C^1$, $C^{1'}$, $C^2$, $C^{2'}$, $C^3$, $C^{3'}$, $C^4$ and/or $C^{4'}$) does not replace the residue of the G unit ($R_1$, $R_4$ and/or $R_5$ of $G^{1-4}$) but bind to it, the particular residue ($R_1$, $R_4$ and/or $R_5$) involved in coupling of G units (or G unit with dye(s) or other reporting group(s)) independently from each other is as defined further above, wherein an endstanding group is replaced by or transformed to a coupling function or selected from the group depicted hereinafter (wherein if present, Q1 connects to the G unit)

n = 0-6; m = 0-6;
$Q_1$ = absent, S, NH, O, C(O), S(O), S(O)$_2$;
$Q_2$ = NH, S, O, C(O), CH$_2$, OC(O), NC(O);

n = 0-4; m = 0-4
$Q_1$ = absent, S, NH, O, C(O), S(O), S(O)$_2$;

22

-continued $n_1$ = 0-4; $n_2$ = 0-4, $n_3$ = 0-4,
$Q_1$ = absent, S, NH, O, C(O), S(O), S(O)$_2$;
$Q_2$ = NH, S, O, C(O), CH$_2$, OC(O), NC(O);

n = 0-4; m = 0-4;
$Q_1$ = absent, S, NH, O, C(O), S(O), S(O)$_2$;

n1 = 0-4; n2 = 0-4, m = 0-4;
$Q_1$ = absent, S, NH, O, C(O), S(O), S(O)$_2$;
$Q_2$ = CH$_2$, O, NH, S;

and wherein
the linker (L) is selected from the group consisting of

| Dimeric Linkers | Trimeric Linkers | Tetrameric linkers |
| --- | --- | --- |
| 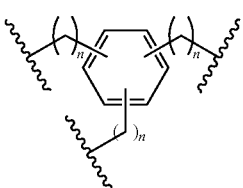 | | |
| n = 0-4 | n = 0-4 | n = 0-4 |

-continued

| Dimeric Linkers | Trimeric Linkers | Tetrameric linkers |
| --- | --- | --- |

$X = CH_2$, O, NH, S, S—S, C(O); n = 0-4

$X = CH_2$, O, NH, S, S—S, C(O); n = 0-4

$X = CH_2$, O, NH, S, S—S, C(O); n = 0-4 or $X = CH_2$, O, NH, S, S—S, C(O); n = 0-4

$X = CH_2$, NH, O, S; n = 0-4; m = 1-2

$X = CH_2$, NH, O, S; n = 0-4; m = 1-2

$X = CH_2$, NH, O, S; n = 0-4; m = 1-2 n = 0-4 n = 0-4 n = 0-4 or n = 0-4 n = 0-4 n = 0-4

-continued

| Dimeric Linkers | Trimeric Linkers | Tetrameric linkers |
|---|---|---| n = 0-4 n = 0-4 n = 0-4

X = NH, O, S; n = 0-4;

X = NH, O, S; n = 0-4;

X = NH, O, S; n = 0-4;

n = 0-6 n = 0-12

X = C, Si; n = 0-6 or m = 0-24, n = 0-6 n = 0-6 n = 0-6 n = 0-4 n = 0-4

-continued

| Dimeric Linkers | Trimeric Linkers | Tetrameric linkers |
|---|---|---|

X = O, S; n = 1-4

X = O, S; n = 1-4

X = CH, P; n = 0-4 n = 0-4

X = B, Si; n = 1-4 n = 1-4 n = 1-4 or n = 1-6; m = 1-11 n = 1-4

29            30

-continued

| Dimeric Linkers | Trimeric Linkers | Tetrameric linkers |
|---|---|---|
| | | |

X = N, CH; n = 1-6; m = 0-10 n = 0-6 while n for each sidechain within a particular linker of the list herebefore can have an equal or individual value as defined and all chiral, diastereomeric, racemic, epimeric, and all geometric isomeric forms of linkers (L) of the list herebefore, though not explicitly depicted, are included herein and kationic linkers (L) such as ammonium-derivatives are salts containing chloride-, bromide-, iodide- phosphate-, carbonate-, sulfate-, acetate- or any other physiologically accepted counterion and wherein spacers ($S^1$, $S^2$, $S^3$ and $S^4$) can be equal or individual within a particular compound, be absent or be —$(CH_2)_{n1}$—$(CH_2CH_2\beta)_m$—$(CH_2)_{n2}$— (with $\beta$=0, S or NH; m=1 to 500, n1=0 to 8, n2=0 to 8, while both n1 and n2 can independently be equal or individual), or —$(CH_2)_n$— (with n=1 to 24).

Particularly, in the preferred embodiment of the invention, wherein it is preferred, that linking residues $LR^1$, $LR^2$, $LR^3$ and $LR^4$ are further subdivided as depicted in formula (Ib) and (IIb), containing spacer moieties ($S^1$-4), coupling functions ($C^{1-4}$, $C^{1'-4'}$) and a linker (L, only multimers of structure Ib), coupling functions ($C^{1-4}$, $C^{1'-4'}$) establish covalent bonds between the spacer and a G unit ($G^1$-4) by connecting to or replacing any of the residues $R_1$, $R_4$ and/or $R_5$ (compare formula structure III)

and/or the spacer and a linker (L), dye or another reporting group and/or (in case the particular spacer is absent) a G unit ($G^{1-4}$) and a dye or another reporting group by connecting to or replacing any of the residues $R_1$, $R_4$ and/or $R_5$ and/or (in case the particular spacer is absent and/or a G unit is replaced by a dye or other reporting group) the linker (L) and a dye or another reporting group or a G unit ($G^{1-4}$, by connecting to or replacing any of the residues $R_1$, $R_4$ and/or $R_5$).

Coupling functions ($C^{1-4}$, $C^{1'-4'}$) are generated in a reaction between endstanding groups of the particular precursor parts according to well established methods of the art. Non limiting examples of precursor endstanding groups (of monomeric G units and (commercially available) linkers, dyes, reporting groups and spacers) and the corresponding coupling functions ($C^{1-4}$, $C^{1'-4'}$), to which they are transformed within the assembled (mono- or multimeric) compound according to the invention, are as depicted in Table 1. Coupling functions ($C^{1-4}$, $C^{1'-4'}$) can independently further be absent or be equal or individual within a particular mono- or multimeric compound.

TABLE 1

Endstanding groups and corresponding coupling functions ($C^{1-4}$, $C^{1'-4'}$)

| Endstanding Group of Monomeric G unit ($R_1$, $R_4$, $R_5$), L, dye, reporting group | Spacer ($S^1$, $S^2$, $S^3$, $S^4$) | (Corresponding) Coupling Function ($C^1$, $C^{1'}$, $C^2$, $C^{2'}$, $C^3$, $C^{3'}$, $C^4$, $C^{4'}$) |
|---|---|---|
| 1   | | |

TABLE 1-continued

Endstanding groups and corresponding coupling functions (C$^{1-4}$, C$^{1'-4'}$)

| Endstanding Group of Monomeric G unit (R$_1$, R$_4$, R$_5$), L, dye, reporting group | Spacer (S$^1$, S$^2$, S$^3$, S$^4$) | (Corresponding) Coupling Function (C$^1$, C$^{1'}$, C$^2$, C$^{2'}$, C$^3$, C$^{3'}$, C$^4$, C$^{4'}$) |
|---|---|---|
| 2 NH$_2$ | $^+$NH$_2$ (O) | $^+$NH$_2$ (N—H) |
| 3 NH$_2$ | Br | N—H |
| 4 NH$_2$ | O=C=N | O (N—H, N—H) |
| 5 NH$_2$ | O (epoxide) | O (N—H), OH |
| 6 NH$_2$ | O$_2$N—(C$_6$H$_4$)—O—C(=O)—O | O (N—H, O) |
| 7 NH$_2$ | O (acrylate ester) | O (N—H), O |
| 8 OH (C=O) | H$_2$N—N(H)—C(=O) | O, N(H)—N(H), O |
| 9 OH (C=O); OMe (C=O) | Br; OH | O (C=O—O) |
| 10 SH | maleimide (O, N, O) | S (succinimide: O, N, O) |
| 11 SH | I—CH$_2$—C(=O)—N(H) | S—CH$_2$—C(=O)—N(H) |

TABLE 1-continued

| Endstanding groups and corresponding coupling functions (C$^{1-4}$, C$^{1'-4'}$) | | |
| --- | --- | --- |
| Endstanding Group of Monomeric G unit (R$_1$, R$_4$, R$_5$), L, dye, reporting group | Spacer (S$^1$, S$^2$, S$^3$, S$^4$) | (Corresponding) Coupling Function (C$^1$, C$^1$', C$^2$, C$^2$', C$^3$, C$^3$', C$^4$, C$^4$') |
| 12 | | |
| 13 | | |
| 14 | | |
| 15 | | |
| 16 | | |
| 17 | | |
| 18 | | |
| 19 | | |
| 20 | | |

TABLE 1-continued

| Endstanding groups and corresponding coupling functions ($C^{1-4}$, $C^{1'-4'}$) | | |
| --- | --- | --- |
| Endstanding Group of Monomeric G unit ($R_1$, $R_4$, $R_5$), L, dye, reporting group | Spacer ($S^1$, $S^2$, $S^3$, $S^4$) | (Corresponding) Coupling Function ($C^1$, $C^{1'}$, $C^2$, $C^{2'}$, $C^3$, $C^{3'}$, $C^4$, $C^{4'}$) |

21

$X_1 = Br, I$
bound to aryl, heteroaryl, alkenyl $X_2 = $ alkyl, OH, O-alkyl
$X_3 = $ NH, O, S $X_3 = $ NH, O, S

22

$X_1 = Br, I$
bound to aryl, heteroaryl, alkenyl $X_2 = $ alkyl, OH, O-alkyl
$X_3 = $ NH, O, S $X_3 = $ NH, O, S

23

$X_1 = Br, I$
bound to aryl, heteroaryl, alkenyl $X_2 = $ alkyl, OH, O-alkyl

24

$X_1 = $ Cl, Br, I, OTf
bound to aryl, heteroaryl, alkenyl

25

26

27

A person skilled in the art understands, that synthetic equivalents of the precursor endstanding groups of Table 1, such as but not limited to NHS esters instead of carboxylic acids or triflates instead of halogens can be used as well to generate the particular corresponding coupling function. A person skilled in the art further understands, that endstanding groups of the synthetic precursors (residues $R_1$, $R_4$ and/or $R_5$, linker (L), dye, reporting group and spacer ($S^{14}$)) can be interchanged amongst each other, resulting in reversed connectivity of the coupling function within the mono- or multimeric analogue.

A non limiting example of a multimeric compound according to the invention, illustrating the used and defined variables above is given in FIG. 1.

Preferred Compounds According to the Invention

According the invention it is preferred that R1 is selected from group consisting of H, halogen, azido, nitro, alkyl, acyl, aryl, OH, O-alkyl, O-aryl, SH, S-alkyl, S-aryl, S-aralkyl, S(O)-alkyl, S(O)-aryl, S(O)-aralkyl, S(O)-benzyl, $S(O)_2$-alkyl, $S(O)_2$-aryl, $S(O)_2$-aralkyl, amino, NH-alkyl, NH-aryl, NH-aralkyl, NR9R10, SiR13R14R15 wherein R9, R10, R13, R14, R15 are alkyl.

According to the invention it is further preferred that R1 is selected from the group consisting of H, Cl, Br, I, F, $N_3$, $NO_2$, OH, SH, $NH_2$, $CF_3$, 2-furyl, 3-furyl, 2-bromo-5-furyl, (2-furyl)thio, (3-(2-methyl)furyl)thio, (3-furyl)thio, 2-thienyl, 3-thienyl, (5-(1-methyl)tetrazolyl)thio, 1,1,2-trifluoro-1-butenthio, (2-(4-phenyl)imidazolyl)thio, (2-benzothiazolyl)thio, (2,6-dichlorophenoxypropyl)thio, 2-(N-(7-nitrobenz-2-oxa-1,3-diazol-4-yl)amino)ethylthio, (4-bromo-2,3-dioxobutyl)thio, [2-[(fluoresceinylthioureido)amino]ethyl]thio, 2,3,5,6-tetrafluorophenylthio, (7-(4-methyl)coumarinyl)thio, (4-(7-methoxy)coumarinyl)thio, (2-naphtyl)thio, (2-(1-bromo)naphtyl)thio, benzimidazolyl-2-thiobenzothiazolylthio, 4-pyridyl, (4-pyridyl)thio, 2-pyridylthio, 5-amino-3-oxopentylamino, 8-amino-3,6-dioxaoctylamino, 19-amino-4,7,10,13,16-pentaoxanonadecylamino, 17-amino-9-aza-heptadecylamino, 4-(N-methylanthranoyl)aminobutylamino, dimethylamino, diethylamino, 4-morpholino, 1-piperidino, 1-piperazino, triphenyliminophosphoranyl or as depicted in Table 2.

TABLE 2

Residue $R_1$.

Entry  Residue

1 wherein
m = 0-6.
Q = S, S(O), $S(O)_2$, O, NH, Se, $CH_2$, C(O).
$X_1$, $X_2$ and $X_3$ can be equal or independently be H, OH, $NH_2$, $N_3$, SH, CN, $NO_2$, F, Cl, Br, I, $(CH_2)_nCH_3$ (with n = 0-5), i-Pr, t-Bu, $(CH_2)_n$=CH (with n = 0-5), $(CH_2)C$=$CH_2$ (with n = 0-5), $CH_2OH$, $(CH_2)_nOCH_3$ (with n = 1-2), $CH_2N(CH_3)_2$, $O(CH_2)_nCH_3$ (with n = 0-5), Oi-Pr, OCy, OCyp, OBn, $OC(O)CH_3$, $OC(O)Ph$, $OCF_3$, $N(CH_3)_2$, $NH(CH_2)_nCH_3$ (with n = 0-5), NHC(O)t-Bu, NHC(O)Ph, NHC(O)Ot-Bu, $NHC(O)CH_3$, $NHC(O)CH_2N_3$, $B(OH)_2$, $CF_3$, C(O)OH, $C(O)OCH_3$, C(O)Oi-Pr, C(O)Ot-Bu, C(O)OPh, C(O)OBn, $C(O)NH_2$, $C(O)N(CH_3)_2$, C(O)NHPh, C(O)NHBn, $C(O)CF_3$, $CH_2C(O)OH$, $CH_2C(O)OCH_3$, $CH_2C(O)Oi$-Pr, $CH_2C(O)Ot$-Bu, $CH_2C(O)OBn$, $S(CH_2)_nCH_3$ (with n = 0-5), $S(CH_2)_nOEt$ (with n =

1-4), SBn, $SO_2CH_3$, $SO_2CF_3$, (with $Y_1$ = H, SH, CN, Ph, F, $CH_3$, $OCH_3$, $SCH_3$, 4-thiophenyl, $NO_2$, pentyl), (with $Y_2$ = H, SH, F), (with $Y_3$ = H, SH),

.

2 wherein
m = 0-6.
Q = S, S(O), $S(O)_2$, O, NH, Se.

According to the invention it is especially preferred that R1 is selected from the group consisting of H, Cl, Br, I, F, $N_3$, $NO_2$, OH, SH, $NH_2$, $CF_3$, 2-furyl, 3-furyl, (2-furyl)thio, (3-(2-methyl)furyl)thio, (3-furyl)thio, 2-thienyl, 3-thienyl, (5-(1-methyl)tetrazolyl)thio, 1,1,2-trifluoro-1-butenthio, (2-(4-phenyl)imidazolyl)thio, (2-benzothiazolyl)thio, (2,6-dichlorophenoxypropyl)thio, 2-(N-(7-nitrobenz-2-oxa-1,3-diazol-4-yl)amino)ethylthio, (4-bromo-2,3-dioxobutyl)thio, [2-[(fluoresceinylthioureido)amino]ethyl]thio, 2,3,5,6-tetrafluorophenylthio, (7-(4-methyl)coumarinyl)thio, (4-(7-methoxy)coumarinyl)thio, (2-naphtyl)thio, (2-(1-bromo)naphtyl)thio, benzimidazolyl-2-thio, benzothiazolylthio, 4-pyridyl, (4-pyridyl)thio, 2-pyridylthio, 5-amino-3-oxo-pentyl amino, 8-amino-3,6-dioxaoctylamino, 19-amino-4,7,10,13,16-pentaoxanonadecylamino, 17-amino-9-aza-heptadecylamino, 4-N methylanthranoyl)aminobutyl amino, dimethylamino, diethylamino, 4-morpholino, 1-piperidino, 1-piperazino, triphenyliminophosphoranyl or as depicted in Table 3.

TABLE 3

Residue $R_1$.

wherein
m = 0-6.
Q = S, S(O), S(O)$_2$, NH.
$X_1$, $X_2$ and $X_3$ can equal or independently be H, OH, $NH_2$, $N_3$, SH, CN, $NO_2$, F, Cl, Br, I, $(CH_2)_nCH_3$ (with n = 0-5), i-Pr, t-Bu, Ph, $(CH_2)_nC\equiv CH$ (with n = 0-5), $(CH_2)_nC=CH_2$ (with n = 0-5), $CH_2OH$, $(CH_2)_nOCH_3$ (with n = 1-2), $CH_2N(CH_3)_2$, $O(CH_2)_nCH_3$ (with n = 0-5), Oi-Pr, OCy, OCyp, OPh, OBn, $OC(O)CH_3$, $OC(O)Ph$, $OCF_3$, $N(CH_3)_2$, $NH(CH_2)_nCH_3$ (with n = 0-5), NHC(O)t-Bu, NHC(O)Ph, NHC(O)Ot-Bu, NHC(O)$CH_3$, NHC(O)$CH_2N_3$, $B(OH)_2$, $CF_3$, C(O)OH, C(O)$OCH_3$, C(O)Oi-Pr, C(O)Ot-Bu, C(O)OPh, C(O)OBn, C(O)$NH_2$, C(O)$N(CH_3)_2$, C(O)NHPh, C(O)NHBn, C(O)$CF_3$, $CH_2C(O)OH$, $CH_2C(O)OCH_3$, $CH_2C(O)Oi$-Pr, $CH_2C(O)Ot$-Bu, $CH_2C(O)OBn$, $S(CH_2)_nCH_3$ (with n = 0-5), $S(CH_2)_nOEt$ (with n = 1-4), SBn, SPh, wherein
m = 0-6.
n = 1-6.
Q = S, S(O), S(O)$_2$, NH.

According to the invention it is even more preferred that R1 is selected from the group consisting of H, Cl, Br, SH, 2-furyl, 3-furyl, (2-furyl)thio, (3-(2-methyl)furyl)thio, (3-furyl)thio, 2-thienyl, 3-thienyl, (5-(1-methyl)tetrazolyl)thio, 1,1,2-trifluoro-1-butenthio, (2-(4-phenyl)imidazolyl)thio, (2-benzothiazolyl)thio, (2,6-dichlorophenoxypropyl)thio, 2-(N-(7-nitrobenz-2-oxa-1,3-diazol-4-yl)amino)ethylthio, (4-bromo-2,3-dioxobutyl)thio, [2-[(fluoresceinylthioureido)amino]ethyl]thio, 2,3,5,6-tetrafluorophenylthio, (7-(4-methyl)coumarinyl)thio, (4-(7-methoxy)coumarinyl)thio, (2-naphtyl)thio, (2-(1-bromo)naphtyl)thio, benzimidazolyl-2-thio, benzothiazolylthio, 4-pyridyl, (4-pyridyl)thio, 2-pyridylthio, triphenyliminophosphoranyl or as depicted in Table 4.

TABLE 4

Residue $R_1$.

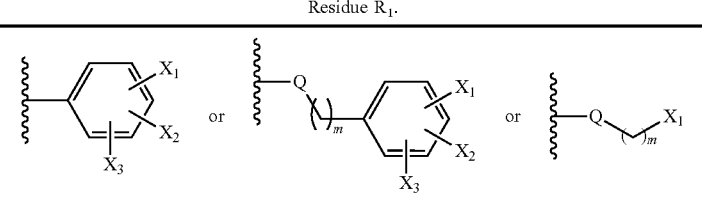

wherein
m = 0-3.
Q = S.
$X_1$, $X_2$ and $X_3$ can be equal or independently be H, OH, $NH_2$, $N_3$, SH, CN, $NO_2$, F, Cl, Br, I, $(CH_2)_nCH_3$ (with n = 0-5), i-Pr, t-Bu, Ph, $(CH_2)_nC\equiv CH$ (with n = 0-5), $(CH_2)_nC=CH_2$ (with n = 0-5), $CH_2OH$, $(CH_2)_nOCH_3$ (with n = 1-2), $CH_2N(CH_3)_2$, $O(CH_2)_nCH_3$ (with n = 0-5), Oi-Pr, OCy, OCyp, OPh, OBn, $OC(O)CH_3$, $OC(O)Ph$, $OCF_3$, $N(CH_3)_2$, $NH(CH_2)_nCH_3$ (with n = 0-5), NHC(O)t-Bu, NHC(O)Ph, NHC(O)Ot-Bu, $NHC(O)CH_3$, $NHC(O)CH_2N_3$, $B(OH)_2$, $CF_3$, C(O)OH, $C(O)OCH_3$, C(O)Oi-Pr, C(O)Ot-Bu, C(O)OPh, C(O)OBn, $C(O)NH_2$, $C(O)N(CH_3)_2$, C(O)NHPh, C(O)NHBn, $C(O)CF_3$, $CH_2C(O)OH$, $CH_2C(O)OCH_3$, $CH_2C(O)Oi$-Pr, $CH_2C(O)Ot$-Bu, $CH_2C(O)OBn$, $S(CH_2)_nCH_3$ (with n = 0-5), $S(CH_2)_nOEt$ (with n = 1-4), SBn, SPh, wherein m = 0-6, n = 1-6, Q = S.

In addition to the above or independent to the above it is preferred that according the invention that R4 is selected from group consisting of H, amino, alkyl, aralkyl, nitro, N-oxide or R4 can form together with Y and $R_5$ and the carbon bridging Y and $R_5$ an imidazole ring which can be unsubstituted or substituted with alkyl, aryl or aralkyl, or can form together with Y and $R_5$ and the carbon bridging Y and $R_5$ an imidazolinone as depicted above (structure IV, V, n=1) or an homologous ring (n=2 to 8) which each can be unsubstituted or substituted (not depicted) with alkyl, aryl or aralkyl.

According to the invention it is further preferred that R4 is absent or selected from the group consisting of amino, N-oxide or as depicted in Table 5.

TABLE 5

Residue $R_4$.

Entry   Residue

1

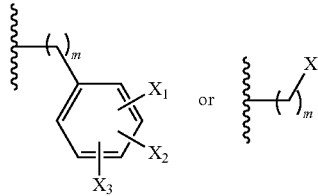

wherein
m = 1-6.
$X_1$, $X_2$ and $X_3$ can be equal or independently be H, $N_3$, CN, $NO_2$, F, Cl, Br, I, $(CH_2)_nCH_3$ (with n = 0-5), i-Pr, t-Bu, $(CH_2)_nC\equiv CH$ (with n = 0-5), $(CH_2)_nC=CH_2$ (with n = 0-5), $(CH_2)_nOCH_3$ (with n = 1-2), $CH_2N(CH_3)_2$, $O(CH_2)_nCH_3$ (with n = 0-5), Oi-Pr, OBn, $OC(O)CH_3$, OC(O)Ph, $OCF_3$, $N(CH_3)_2$, NHC(O)t-Bu, NHC(O)Ph, NHC(O)Ot-Bu, $NHC(O)CH_3$, $NHC(O)CH_2N_3$, $CF_3$, $C(O)OCH_3$, C(O)Oi-Pr, C(O)Ot-Bu, C(O)OPh, C(O)OBn, $C(O)NH_2$, $C(O)N(CH_3)_2$, C(O)NHPh, C(O)NHBn, $C(O)CF_3$, $CH_2C(O)OCH_3$, $CH_2C(O)Oi$-Pr, $CH_2C(O)Ot$-Bu, $CH_2C(O)OBn$, $S(CH_2)_nCH_3$ (with n = 0-5), $S(CH_2)_nOEt$ (with n = 1-4), SBn, SPh, $SO_2CF_3$, TABLE 5-continued

| Residue $R_4$. |
| --- |

| Entry | Residue |
| --- | --- |

(with $Y_1$ = H, CN, Ph, F, $CH_3$, $OCH_3$, $SCH_3$, $NO_2$, pentyl),      (with $Y_2$ = H, F),

2

=     or wherein $X_1$ can be H, $CH_3$, Ph.

$X_2$ can be H, Ph, 2-naphtyl, 9-phenanthryl, 1-pyrenyl, 2,3-dihydro-1,4-benzodioxin-6-yl, dibenzo[b,d]furan-2-yl, 2,3-dihydro-1-benzofuran-5-yl, 1-benzothien-5-yl, 1-benzofuran-5-yl, cyclopropyl, 1-adamantyl, $C(Ph)_3$, 2-thienyl, 3-chloro-2-thienyl, 3-thienyl, 1,3-thiazol-2-yl, 2-pyridinyl, 5-chloro-2-thienyl, 1-benzofuran-2-yl, $X_3$, $X_4$ and $X_5$ can independently be OH, NH, $CH_3$, Cl, Br, F, CN, $N_3$, $CF_3$, $OCF_3$, $NO_2$, C(O)OH, $C(O)OCH_3$, $OCH_3$, OBn, O-benzoyl, $SCH_3$, t-Bu, $N(CH_3)_2$, S-phenyl, Ph, $S(O)_2CH_3$, $C(O)NH_2$, $NHS(O)_2CH_3$,

3

=     or wherein deviating from the definition above, any hydrogen atom attached to any of the ring carbon atoms including depicted, implied, or expressly defined hydrogen, or both hydrogen atoms (m = 2) attached to the same particular carbon atom, can be replaced by one or two (equal) "floating groups" $X_1$ respectively, as long as a stable structure is formed while m = 1 or 2.

n = 1-4.

$X_1$ can be H, $CH_3$, Et, Pr, i-Pr, Bu, F, Ph, $(CH_2)_2OH$*

*Only for first case.

4 or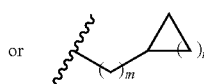

wherein m = 1-6.

n = 1-6.

According to the invention it is especially preferred that R4 is absent or selected from the group consisting of amino, N-oxide or as depicted in Table 6.

TABLE 6

| Residue $R_4$. | |
| --- | --- |
| Entry | Residue |

1 wherein
m = 1-3.
$X_1$, $X_2$ and $X_3$ can be equal or independently be H, $N_3$, CN, $NO_2$, F, Cl, Br, I, $(CH_2)_nCH_3$ (with n = 0-5), i-Pr, t-Bu, Ph, $(CH_2)_nC\equiv CH$ (with n = 0-5), $(CH_2)_nC=CH_2$ (with n = 0-5), $(CH_2)_nOCH_3$ (with n = 1-2), $CH_2N(CH_3)_2$, $O(CH_2)_nCH_3$ (with n = 0-5), Oi-Pr, OPh, OBn, OC(O)CH$_3$, OC(O)Ph, OCF$_3$, N(CH$_3$)$_2$, NHC(O)t-Bu, NHC(O)Ph, NHC(O)Ot-Bu, NHC(O)CH$_3$, NHC(O)CH$_2$N$_3$, CF$_3$, C(O)OCH$_3$, C(O)Oi-Pr, C(O)Ot-Bu, C(O)OPh, C(O)OBn, C(O)NH$_2$, C(O)N(CH$_3$)$_2$, C(O)NHPh, C(O)NHBn, C(O)CF$_3$, CH$_2$C(O)OCH$_3$, CH$_2$C(O)Oi-Pr, CH$_2$C(O)Ot-Bu, CH$_2$C(O)OBn, S(CH$_2$)$_n$CH$_3$ (with n = 0-5), S(CH$_2$)$_n$OEt (with n = 1-4), SBn, SPh, SO$_2$CF$_3$,

2 wherein
$X_1$ can be H, CH$_3$, Ph.
$X_2$ can be H, Ph, 2-naphthyl, 9-phenanthryl, 1-pyrenyl, 2,3-dihydro-1,4-benzodioxin-6-yl, dibenzo[b,d]furan-2-yl, 2,3-dihydro-1-benzofuran-5-yl, 1-benzothien-5-yl, 1-benzofuran-5-yl, cyclopropyl, 1-adamantyl, C(Ph)$_3$, 2-thienyl, 3-chloro-2-thienyl, 3-thienyl, 1,3-thiazol-2-yl, 2-pyridinyl, 1-benzofuran-2-yl;
$X_3$, $X_4$ and $X_5$ can independently be OH, NH, CH$_3$, Cl, Br, F, CN, N$_3$, CF$_3$, OCF$_3$, NO$_2$, C(O)OH, C(O)OCH$_3$, OCH$_3$, OBn, O-benzoyl, SCH$_3$, t-Bu, N(CH$_3$)$_2$, S-phenyl, Ph, S(O)$_2$CH$_3$, C(O)NH$_2$, NHS(O)$_2$CH$_3$,

3 wherein deviating from the definition above, any hydrogen atom attached to any of the ring carbon atoms including depicted, implied, or expressly defined hydrogen, or both hydrogen atoms (m = 2) attached to the same particular carbon atom, can be replaed by one or two (equal) "floating groups" $X_1$ respectively, as long as a stable structure is formed.
while m = 1 or 2.
n = 1-4.
$X_1$ can be H, CH$_3$, Et, Pr, i-Pr, Bu, F, Ph, (CH$_2$)$_2$OH*

TABLE 6-continued

Residue $R_4$.

| Entry | Residue |
|---|---|
| 4 | or (structure) wherein m = 1-6. n = 1-6. |

*Only for first case.

According to the invention it is even more preferred that R4 is absent or as depicted in Table 7.

TABLE 7

Residue $R_4$.

Entry | Residue

1 wherein
m = 1-3.
$X_1$, $X_2$ and $X_3$ can be equal or independently be H, $N_3$, CN, $NO_2$, F, Cl, Br, I.
$(CH_2)_nCH_3$ (with n = 0-5), i-Pr, t-Bu, Ph, $(CH_2)_nC\equiv CH$ (with n = 0-5), $(CH_2)_nC=CH_2$
(with n = 0-5), $(CH_2)_nOCH_3$ (with n = 1-2), $CH_2N(CH_3)_2$, $O(CH_2)_nCH_3$ (with n = 0-5),
Oi-Pr, OPh, OBn, OC(O)CH$_3$, OC(O)Ph, OCF$_3$, N(CH$_3$)$_2$, NHC(O)t-Bu, NHC(O)Ph,
NHC(O)Ot-Bu, NHC(O)CH$_3$, NHC(O)CH$_2$N$_3$, CF$_3$, C(O)OCH$_3$, C(O)Oi-Pr,
C(O)Ot-Bu, C(O)OPh, C(O)OBn, C(O)NH$_2$, C(O)N(CH$_3$)$_2$, C(O)NHPh, C(O)NHBn,
C(O)CF$_3$, CH$_2$C(O)OCH$_3$, CH$_2$C(O)Oi-Pr, CH$_2$C(O)Ot-Bu, CH$_2$C(O)OBn,
S(CH$_2$)$_n$CH$_3$ (with n = 0-5), S(CH$_2$)$_n$OEt (with n = 1-4), SBn, SPh, SO$_2$CF$_3$,

2 wherein
$X_1$ can be H, CH$_3$, Ph.
$X_2$ can be H, Ph, 2-naphthyl, 9-phenanthryl, 1-pyrenyl, 2,3-dihydro-1,4-benzodioxin-6-
yl, dibenzo[b,d]furan-2-yl, 2,3-dihydro-1-benzofuran-5-yl, 1-benzothien-5-yl, 1-
benzofuran-5-yl, cyclopropyl, 1-adamantyl, C(Ph)$_3$, 2-thienyl, 3-chloro-2-thienyl, 3-
thienyl, 1,3-thiazol-2-yl, 2-pyridinyl, 1-benzofuran-2-yl;
$X_3$, $X_4$ and $X_5$ can independently be OH, NH, CH$_3$, Cl, Br, F, CN, N$_3$, CF$_3$, OCF$_3$, NO$_2$,
C(O)OH, C(O)OCH$_3$, OCH$_3$, OBn, O-benzoyl, SCH$_3$, t-Bu, N(CH$_3$)$_2$, S-phenyl, Ph,
S(O)$_2$CH$_3$, C(O)NH$_2$, NHS(O)$_2$CH$_3$, TABLE 7-continued Residue R$_4$.

| Entry | Residue |
| --- | --- |
| 3 | | wherein
n = 1-4.

| 4 | | wherein
m = 1-3.
n = 1-6.

In addition to the above or independent to the above it is preferred that according the invention that R5 is selected from the group consisting of H, halogen, azido, acyl, aracyl, nitro, alkyl, aryl, aralkyl, amido-alkyl, amido-aryl, amido-aralkyl, amido-O-alkyl, amido-O-aryl, amido-O-aralkyl, NH-carbamoyl-alkyl, NH-carbamoyl-aryl, NH-carbamoyl-aralkyl, OH, O-alkyl, O-aryl, O-aralkyl, SH, S-alkyl, S-aryl, S-aralkyl, amino, NH-alkyl, NH-aryl, NH-aralkyl, NR30R31, SiR34R35R36 wherein R30, R31, R34, R35, R36 are alkyl, or can form together with R$_4$, Y and the carbon bridging Y and R$_5$ an imidazole ring which can be unsubstituted or substituted with alkyl, aryl or aralkyl, or can form together with R$_4$, Y and the carbon bridging Y and R$_5$ an imidazolinone ring as depicted above (structure IV, V, n=1) or an homologous ring (n=2 to 8) which each can be unsubstituted or substituted (not depicted) with alkyl, aryl or aralkyl.

According to the invention it is further preferred that R5 is selected from the group consisting of H, NH$_2$, F, Cl, Br, I, nitro, methyl, ethyl, n-propyl, n-hexyl, 6-amino-n-hexyl, trifluoromethyl, phenyl, 4-N,N-dimethylaminophenyl, benzyl, 4-azidobenzyl, amido-n-butyl, amidoisobutyl, amido(6-amino-n-hexyl), OH, methyloxy, n-hexyloxy, phenyloxy, benzyloxy, SH, methylthio, ethylthio, 6-amino-n-hexylthio, phenylthio, 4-azidophenylthio, benzylthio, 4-azidobenzylthio, methylamino, NH-benzyl, NH-phenyl, NH-4-azidophenyl, NH-phenylethyl, NH-phenylpropyl, 2-aminoethylamino, n-hexylamino, 6-amino-n-hexylamino, 8-amino-3,6-dioxaoctylamino, dimethylamino, 1-piperidino, 1-piperazino, trimethylsilyl, triethylsilyl, tert-butyldimethylsilyl or can form together with R$_4$, Y and the carbon bridging Y and R$_5$ a ring system as depicted in Table 5 (entry 2 and 3).

According to the invention it is especially preferred that R5 is selected from the group consisting of H, NH$_2$, F, Cl, Br, I, nitro, SH, methylthio, ethylthio, 6-amino-n-hexylthio, phenylthio, 4-azidophenylthio, benzylthio, 4-azidobenzylthio, methylamino, NH-benzyl, NH-phenyl, NH-4-azidophenyl, NH-phenylethyl, NH-phenylpropyl, 2-aminoethylamino, n-hexylamino, 6-amino-n-hexylamino, 8-amino-3,6-dioxaoctylamino, dimethylamino, 1-piperidino, 1-piperazino or can form together with R$_4$, Y and the carbon bridging Y and R$_5$ a ring system as depicted in Table 6 (entry 2 and 3).

According to the invention it is even more preferred that R5 is NH$_2$, or can form together with R$_4$, Y and the carbon bridging Y and R$_5$ a ring system as depicted in Table 7 (entry 2 and 3).

In addition to the above or independent to the above it is preferred that according the invention that R8 is selected from group consisting of SH, S-alkyl, S-aryl, S-aralkyl, borano (BH$_3$), methylborano, dimethylborano, cyanoborano (BH$_2$CN), S-PAP, Se-PAP, S-BAP or Se-BAP wherein PAP is a photo-activatable protecting group with PAP=o-nitro-benzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged) and 6,7-bis(carboxymethoxy)coumarin-4-yl)methyl (BCMCM-caged).

and wherein BAP is a bio-activatable protecting group with BAP=methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, 4-benzoyloxybenzyl.

According to the invention it is further preferred that R8 is selected from the group consisting of SH, methylthio, acetoxymethylthio, pivaloyloxymethylthio, methoxymethylthio, propionyloxymethylthio, butyryloxymethylthio, cyanoethylthio, phenylthio, benzylthio, 4-acetoxybenzylthio, 4-pivaloyloxybenzylthio, 4-isobutyryloxybenzylthio, 4-octanoyloxybenzylthio, 4-benzoyloxybenzylthio, borano (B1H$_3$), methylborano, dimethylborano, cyanoborano (BH$_2$CN).

According to the invention it is especially preferred that R8 is selected from the group consisting of SH, methylthio, acetoxymethylthio, pivaloyloxymethylthio, methoxymethylthio, propionyloxymethylthio, butyryloxymethylthio, cyanoethylthio, phenylthio, benzylthio, 4-acetoxybenzylthio, 4-pivaloyloxybenzylthio, 4-isobutyryloxybenzylthio, 4-octanoyloxybenzylthio, 4-benzoyloxybenzylthio.

According to the invention it is even more preferred that R8 is SH.

In addition to the above or independent to the above it is preferred that according the invention residues involved in connecting a G unit with another G unit or a dye or another reporting group can be $R_1$, $R_4$ and/or $R_5$ in which case the particular residue is as defined for the preferred embodiment above, wherein an endstanding group is replaced by or transformed to the coupling function or selected from the group depicted in Table 8 (wherein if present, Q1 connects to the G unit).

TABLE 8

Residues $R_1$, $R_4$ and $R_5$ involved in connecting a G unit with another G unit or a dye or another reporting group (if present $Q_1$ connects to the G unit)

n = 0-6; m = 0-6;
Q1 = absent, S, NH, O;
Q2 = NH, S, O, C(O), CH₂,
OC(O), NC(O);

n = 0-4, m = 0-4
Q1 = absent, S, NH, O;

n1 = 0-4, n = 0-4, n3 = 0-4,
Q1 = absent, S, NH, O;
Q2 = NH, S, O, C(O), CH₂,
OC(O), NC(O);

TABLE 8-continued

Residues $R_1$, $R_4$ and $R_5$ involved in connecting a G unit with another G unit or a dye or another reporting group (if present $Q_1$ connects to the G unit)

According to the invention it is further preferred that residues involved in connecting a G unit with another G unit or a dye or another reporting group can be $R_1$, $R_4$ and/or $R_5$, in which case the particular residue is as defined for its preferred embodiment, wherein an endstanding group is replaced by or transformed to a coupling function or selected from the group depicted in Table 9 (wherein if present, Q1 connects to the G unit)

TABLE 9

Residues $R_1$, $R_4$ and $R_5$ involved in connecting a G unit with another G unit or a dye or another reporting group (if present $Q_1$ connects to the G unit)

| $R_1$ | $R_4$ | $R_4 + R_5$ |
|---|---|---|
| n= 0-4, m = 0-4<br>Q₁ = absent, S; | n = 0-4, m = 0-4 | 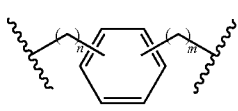 |

TABLE 9-continued

Residues $R_1$, $R_4$ and $R_5$ involved in connecting a G unit with another G unit or a dye or
another reporting group (if present $Q_1$ connects to the G unit)

| $R_1$ | $R_4$ | $R_4$ + $R_5$ |
|---|---|---|

$n_1$ = 0-4, $n_2$ = 0-4, $n_3$= 0-4,
$Q_1$ = absent (for $n_1$ = 0), S;
$Q_2$ = NH, S, O, $CH_2$,
NC(O);

n = 0-6, m = 0-6 n = 0-6; m = 0-6;
Q1 = S;
Q2 = NH, S, O, $CH_2$,
NC(O);

In addition to the above or independent to the above it is preferred that according the invention that coupling functions ($C^{1-4}$ and $C^{1'-4'}$) are absent or selected from the group depicted in Table 10.

TABLE 10

Coupling functions ($C^{1-4}$ and $C^{1'-4'}$).

TABLE 10-continued

Coupling functions ($C^{1-4}$ and $C^{1'-4'}$).

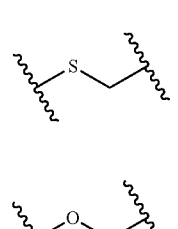

TABLE 10-continued

Coupling functions ($C^{1-4}$ and $C^{1'-4'}$).

$X_3$ = NH, O, S

X = O, S, NH, S(O), S(O)$_2$,
CH$_2$, C(O)

According to the invention it is further preferred that coupling functions ($C^{1-4}$ and $C^{1'-4'}$) are absent or selected from the group depicted in Table 11.

TABLE 11

Coupling functions ($C^{1-4}$ and $C^{1'-4'}$).

TABLE 11-continued

Coupling functions ($C^{1-4}$ and $C^{1'-4'}$).

$X_3$ = NH, O, S

X = O, S, NH, CH$_2$

In addition to the above or independent to the above it is preferred that according the invention the linker (L) is absent or selected from the group depicted in Table 12.

TABLE 12

Linker (L).

n = 0-4 n = 0-4

TABLE 12-continued

| Linker (L). |
| --- | n = 0-4 n = 0-6 n = 0-12

X = C, Si; n = 0-6
or m = 0-24, n = 0-6 n = 0-6 n = 0-6

TABLE 12-continued

| Linker (L). |
| --- |

X = O, S; n = 1-4

X = O, S; n = 1-4

X = B, Si; n = 1-4 n = 1-4

X = N, CH; n = 1-6;
m = 0-10

TABLE 12-continued

Linker (L).

n = 1-6; m = 1-11

While n for each sidechain within a particular linker can have an equal or individual value as defined.

In addition to the above or independent to the above it is preferred that in case of formula (I) according to the invention $G^4$ or $G^4$ and $G^3$ are absent or in case of formula (II) $G^4$ and $LR^4$ or $G^4$, $LR^4$, $G^3$ and $LR^3$ are absent.

According to the invention it is even more preferred that in case of formula (I) $G^4$ and $G^3$ are absent or in case of formula (II) $G^4$, $LR^4$, $G^3$ and $LR^3$ are absent.

Particularly preferred embodiments of the invention based on the above exemplifications, are as defined in anyone of the claims 5, 6, 7 and 8.

Especially preferred according to the invention are the compounds of Table 13, and as defined in claim 9. It has to be noted that in case of doubt the chemical structure as depicted in the formula is the valid one. It further has to be noted, that the compounds of Table 13 are displayed as the free acid. The present invention, however, also comprises salts of these compounds, featuring cations such as but not limited to $Na^+$, $Li^+$, $NH_4^+$, $Et_3NH^+$ and $(i\text{-}Pr)_2EtNH^+$.

TABLE 13

Structures of novel equatorially modified polymer linked multimeric cGMP compounds according to the invention.

| En-try | Compound | Structure |
|---|---|---|
| 1 | Guanosine-3′,5′-cyclic monophosphorothioate[Rp]-[8-thiomethylamido-(octaethoxy)-ethylamidomethylthio-8]-guanosine-3′,5′-cyclic monophosphorothioate[Rp] | Rp-cGMP-8-TMAmd-(EO)8-EAmdMT-8-Rp-cGMPS |
| 2 | β-Phenyl-1, N²-ethenoguanosine-3′,5′-cyclic monophosphorothioate[Rp]-[8-thiomethylamido-(octaethoxy)-ethylamidomethylthio-8]-β-phenyl-1,N²-ethenoguanosine-3′,5′-cyclic monophosphorothioate[Rp] | PET-Rp-cGMPS-8-TMAmd-(EO)8-EAmdMT-8-Rp-cGMPS-PET |

TABLE 13-continued

Structures of novel equatorially modified polymer linked multimeric cGMP
compounds according to the invention.

| En-try | Compound | Structure |
|--------|----------|-----------|
| 3 | β-1,N²-Acetylguanosine-3',5'-cyclic monophosphorothioate[Rp]-[8-thiomethylamido-(octaethoxy)-ethylamidomethylthio-8]-β-1,N²-acetylguanosine-3',5'-cyclic monophosphorothioate[Rp] | β-1, N²-Ac-Rp-cGMPS-8-TMAmd-(EO)₈-EAmdMT-8-Rp-cGMPS-β-1,N²-Ac |
| 4 | β-Phenyl-1,N²-ethenoguanosine-3',5'-cyclic monophosphorothioate[Rp]-[8-thio-(pentaethoxy)-ethylthio-8]-β-phenyl-1,N²-ethenoguanosine-3',5'-cyclic monophosphorothioate[Rp] | PET-Rp-cGMPS-8-T-(EO)₅-ET-8-Rp-cGMPS-PET |

TABLE 13-continued

Structures of novel equatorially modified polymer linked multimeric cGMP compounds according to the invention.

| Entry | Compound | Structure |
|---|---|---|
| 5 | Guanosine-3',5'-cyclic monophosphorothioate[Rp]-[8-thiomethylamido-(EO)$_n$-ethylamidomethylthio-8]-guanosine-3',5'-cyclic monophosphorothiate[Rp] | Rp-cGMPS-8-TMAmd-(EO)$_n$-EAmd/MT-8-Rp-cGMPS<br><br>(with n = 4-20 or (EO)$_n$ referring to PEG polydispers 2000 Da) |
| 6 | β-Phenyl-1,N$^2$-ethenoguanosine-3',5'-cyclic monophosphorothioate[Rp]-[8-thiomethylamido-(EO)$_n$-ethylamidomethylthio-8]-β-phenyl-1,N$^2$-ethenoguanosine-3',5'-cyclic monophosphorothiate[Rp] | PET-Rp-cGMPS-8-TMAmd-(EO)$_n$-EAmdMT-8-Rp-cGMPS-PET<br><br>(with n= 4-20 or (EO)$_n$ referring to PEG polydispers 2000 Da) |

TABLE 13-continued

Structures of novel equatorially modified polymer linked multimeric cGMP compounds according to the invention.

| En-try | Compound | Structure |
|---|---|---|
| 7 | Guanosine-3',5'-cyclic monophosphorothioate[Rp]-[8-thio-(pentaethoxy)-ethylthio-8]-guanosine-3',5'-cyclic monophosphorothioate[Rp] | |
| 8 | Guanosine-3',5'-cyclic monophosphorothioate[Rp]-[8-thio-(dodecanyl)-thio-8]-guanosine-3',5'-cyclic monophosphorothioate[Rp] | |

Rp-cGMPS-8-T-(EO)₅-ET-8-Rp-cGMPS

Rp-cGMPS-8-T-(CH₂)₁₂-T-8-Rp-cGMPS

TABLE 13-continued

Structures of novel equatorially modified polymer linked multimeric cGMP compounds according to the invention.

| En-try | Compound | Structure |
|---|---|---|
| 9 | 8-Bromoguanosine-3',5'-cyclic monophosphorothioate[Rp]-[1, N²-etheno-β-phenyl-4-yl-(1-[1,2,3]-triazole-4-yl)-methoxy-(hexaethoxy)-methyl-(4-[1, 2,3]-triazole-1-yl)-β-phenyl-1, N²-etheno)]-8-bromoguanosine-3',5'-cyclic monophosphorothioate[Rp] |  8-Br-Rp-cGMPS-ETP-p(1-[1,2,3]-Tz-4)-MeO-(EO)₆-Me-p(4-[1,2,3]-Tz-1)-PET-Rp-cGMPS-8-Br |
| 10 | Guanosine-3',5'-cyclic monophosphorothioate[Rp]-[8-thiomethylamiodo-(octaethoxy)-ethylamiodomethylthio-8]-β-phenyl-1,N²-ethenoguanosine-3', 5'-cyclic monophosphorothioate[Rp] |  Rp-cGMPS-8-TMAmd-(EO)₈-EAmdMT-8-Rp-cGMPS-PET |

TABLE 13-continued

Structures of novel equatorially modified polymer linked multimeric cGMP compounds according to the invention.

| En-try | Compound | Structure |
|---|---|---|
| 11 | Benzene-1,3,5-tri-[(8-amiodomethyl-(pentaethoxy)-propylamidomethyl-thio)guanosine-3',5'-cyclic monophosphorothioate[Rp]] | Bn-1,3,5-tri(AmdPr-(OE)₅-MAmdMT-8-Rp-cGMPS |

TABLE 13-continued

Structures of novel equatorially modified polymer linked multimeric cGMP compounds according to the invention.

| En-try | Compound | Structure |
|---|---|---|
| 12 | Ethylene glycol-bis(2-aminoethylether)-N,N,N′,N′-tetra-[(8-methylamidoethylthio)-guanosine-3′,5′-cyclic monophosphorothioate[Rp]] | EG-N,N,N′,N′-tetra(8-MAmdET-Rp-cGMPS) |

TABLE 13-continued

Structures of novel equatorially modified polymer linked multimeric cGMP compounds according to the invention.

| Entry | Compound | Structure |
|---|---|---|
| 13 | Guanosine-3',5'-cyclic monophosphorothioate[Rp]-[8-thioethylamidomethyl-(1-[1,2,3]-triazole-4-yl)-methoxy-(hexaethoxy)-methyl-(4-[1,2,3]-triazole-1-yl)-methylamidoethylthio-8]-guanosine-3',5'-cyclic monophosphorothioate[Rp] | Rp-cGMPS-8-TEAmdM-(1-[1,2,3]-Tz-4)-MeO-(EO)₆-Me-(4-[1,2,3]-Tz-1)-MAmdEt-8-Rp-cGMPS |
| 14 | Guanosine-3',5'-cyclic monophosphorothioate[Rp]-[8-thioethylamidomethyl-(1-[1,2,3]-triazole-4-yl)-methoxy-(hexaethoxy)-methyl-(4-[1,2,3]-triazole-1-yl)-β-phenyl-1,N²-etheno)]-8-bromoguanosine-3',5'-cyclic monophosphorothioate[Rp] | Rp-cGMPS-8-TEAmdM-(1-[1,2,3]-Tz-4)-MeO-(EO)₆-Me-(4-[1,2,3]-Tz-1)-PET-8-Br-Rp-cGMPS |

TABLE 13-continued

Structures of novel equatorially modified polymer linked multimeric cGMP compounds according to the invention.

| En-try | Compound | Structure |
|---|---|---|
| 15 | 8-Bromoguanosine-3',5'-cyclic monophosphorothioate[Rp]-[1-(pentaethoxy)-ethyl-1]-8-bromoguanosine-3',5'-cyclic monophosphorothioate[Rp] | <br>8-Br-Rp-cGMPS-1-(EO)₅-E-1-Rp-cGMPS-8-Br |
| 16 | 8-Bromoguanosine-3',5'-cyclic monophosphorothioate[Rp]-[1-propylamidomethyl-(pentaethoxy)-propyliodopropyl-1]-8-bromoguanosine-3',5'-cyclic monophosphorothioate[Rp] | <br>8-Br-Rp-cGMPS-1-PrAmdM-(EO)₅-PrAmdPr-1-Rp-cGMPS-8-Br |

TABLE 13-continued

Structures of novel equatorially modified polymer linked multimeric cGMP compounds according to the invention.

| En-try | Compound | Structure |
|---|---|---|
| 17 | 8-Bromoguanosine-3′,5′-cyclic monophosphorothioate[Rp]-[1-propylamidomethyl-(pentaethoxy)-propylamidomethylthio-8]-guanosine-3′,5′-cyclic monophosphorothioate[Rp] | 8-Br-Rp-cGMPS-1-PrAmdM-(EO)₅-PrAmdMT-8-Rp-cGMPS |
| 18 | 8-Bromoguanosine-3′,5′-cyclic monophosphorothioate[Rp]-[1-propylamidomethyl-(pentaethoxy)-propylamidomethylthio-8]-β-phenyl-1,N²-ethenoguanosine-3′,5′-cyclic monophosphorothioate[Rp] | 8-Br-Rp-cGMPS-1-PrAmdM-(EO)₅-PrAmdMT-8-Rp-cGMPS-PET |

TABLE 13-continued

Structures of novel equatorially modified polymer linked multimeric cGMP compounds according to the invention.

| Entry | Compound | Structure |
|---|---|---|
| 19 | Guanosine-3',5'-cyclic monophosphorothioate[Rp]-[8-(phenyl-4-thio)-(pentaethoxy)-ethyl-(4-thiophenyl)-8]-guanosine-3',5'-cyclic monophosphorothioate[Rp] | <br>Rp-cBMPS-8-PpT-(EO)₅-EpTP-8-Rp-cGMPS |
| 20 | β-(3-Thiophenyl)-1,N²-ethenoguanosine-3',5'-cyclic monophosphorothioate[Rp]-[8-thiomethylamido-(PEG pd 2000)-amidomethylthio-8]-β-(3-thiophenyl)-1,N²-ethenoguanosine-3',5'-cyclic monophosphorothioate[Rp] | <br>(with (CH₂CH₂O)ₙ referring to PEG polydispers 2000 Da)<br>(3-Tp)ET-Rp-cGMPS-8-TMAmd-(PEG pd 2000)-AmdMT-8-Rp-cGMPS-(3-Tp)ET |

It has to be noted, that the term equatorially modified, as used herein, refers to modifications of the $R_8$ position as depicted in formula III. For the non limiting example of the invention, wherein $R_8$ is SH, representing a phosphorothioate group, the resulting configuration is Rp. Care should be taken, not to confuse this situation with the mirrored case (displayed below), which is not part of the invention and wherein the sulfur modification is also in equatorial position, but the resulting configuration is Sp.

Structures 1, 2, 4-13 and 15-19 from priority application contained this obviously editorially false structural element and were corrected in this respect, as unambiguaously and directly derivable for a person skilled in the art from priority application. The editorially false structural element is easily created by mistake, when flipping the lower ribose part for optical or symmetrical reasons during drawing of the structure. Flipping, however, leads to mirroring the chiral phosphorous center, wherein an Rp configuration is mistakenly converted into Sp. The described editorially false structural element with Sp configuration thus is an obvious clerical mistake for one skilled in the art, as for once the generic formula III does not allow this situation and second all applied monomeric precursors for synthesis of the depicted explicit examples of the invention (Table 13), were Rp configured. A person skilled in the art without doubt knows, that this configuration can not be inverted under the used reaction conditions, thus all G units within the assembled multimers of Table 13 must be Rp configurated.

Monomeric equatorially modified precursor cGMP analogues (G units) for the synthesis of equatorially modified polymer linked multimeric cGMP analogues (PLMs) are compounds of formula (III). As described above, potencies to prevent cell death in primary rod-like cells and retinal explants from rd1 mouse, is strongly increased, once the monomeric precursor is linked to additional one(s) within a PLM. Non limiting examples of new robust and regioselective methods for the transformation of monomeric precursors into exemplary equatorially modified PLMs are given in the examples section. In addition Table 1 gives an overview of exemplary endstanding groups, that can be used for coupling reactions and the corresponding coupling functions within the PLM, to which they are transformed according to established methods of the art.

The invention in one aspect also relates to monomeric compounds of formula (III) and/or monomeric precursors according to formula (III), of any compound of the invention as described herein above, wherein the monomeric compound of formula (III) and/or the monomeric precursor of formula (III) is defined in the context of any said compounds herein above, and preferably wherein the monomeric compound of formula (III) and/or monomeric precursor of formula (III) complies with the following proviso:

$R_8$ is not a substituted or unsubstituted borano function and in addition complies with the proviso, that the monomeric compound of formula (III) and/or the monomeric precursor compound of formula (III) is not selected from the group of compounds consisting of Rp- isomer
with $X_1$ = NH or S;
$X_2$ = F, Cl, Br, I, OH, SH, $NH_2$, $NO_2$, $OCH_3$, $CH_3$, or $CF_3$
$R_6$ = OH Rp-isomer,
with $R_1$ = H, F, Cl, Br, I, $CF_3$, $NH(CH_2)_2NH_2$, $S(CH_2)_2NH_2$ or $R_6$ = OH Rp-isomer Rp-isomer -continued Rp-isomer Rp-isomer,
with R₁ = H, CF₃, Br, Cl,
NH(CH₂)NH₂, S(CH₂)₂NH₂

$R_6$ = OH

Rp-isomer

In a preferred embodiment of the invention the monomeric compound of formula (III) and/or monomeric precursor according to formula (III), of any compound of the invention as described herein above, complies with the provisos, that $R_8$ is not a substituted or unsubstituted borano function and $R_4$ is not H and R5 is NH₂
or $R_5$ is not NH₂, H, 4-methoxytrityl and $R_4$ and $R_5$ are not or
$R_4$ and $R_5$ are and $R_1$ is selected from the group defined above featuring an attachment via a —NH—, —S—, —S(O)— or —S(O)₂— bridge or via carbon-carbon bond, excluding —SH, NH₂, —S(CH₂)ₙNH₂, —S(CH₂)ₙOH, —NH(CH₂)ₙNH₂ and —NH(CH₂)ₙOH (with n=1-100)
or
$R_1$ is as described just above excluding mono para-substituted phenylthio and mono para-substituted phenylamino.

In another preferred embodiment of the invention the monomeric compound of formula (III) and/or monomeric precursor according to formula (III), of any compound of the invention as described herein above, complies with the provisos, that $R_8$ is not a substituted or unsubstituted borano function and $R_4$ is not H and $R_4$+$R_5$ is not or
$R_4$ is H and $R_5$ is not NH₂ and
(a) R1 is not H
or
(b) $R_5$ is not H or 4-methoxytrityl
or
$R_4$ and $R_5$ are and $R_1$ is selected from the group defined above featuring an attachment via a —NH—, —S—, —S(O)— or —S(O)₂— bridge or via carbon-carbon bond, excluding —SH, NH₂, —S(CH₂)ₙNH₂, —S(CH₂)ₙOH, —NH(CH₂)ₙNH₂ and —NH(CH₂)ₙOH (with n=1-100)
or
$R_1$ is as described just above excluding mono para-substituted phenylthio and mono para-substituted phenylamino.

In a further preferred embodiment of the invention the monomeric compound of formula (III) and/or monomeric precursor according to formula (III), of any compound of the invention as described herein above, the monomeric compound of formula (III) and/or the monomeric precursor of the invention is selected from the group depicted in Table 14.

TABLE 14

| En-try | Com-pound | Structure |
|---|---|---|
| | | Structures of novel monomeric precursor compounds according to the invention. |

21 β-1,N²-Acetyl-8-bromoguanosine-3',5'-cyclic monophosphorothioate, Rp-isomer

Rp-β-1,N²-Ac-8-Br-cGMPS 22 8-Bromo-(4-methyl-β-phenyl-1,N²-etheno)guanosine-3',5'-cyclic monophosphorothioate, Rp-isomer Rp-8-Br-pMe-PET-cGMPS 23 8-Bromo-(3-thiophen-1-yl-1,N²-etheno)guanosine-3',5'-cyclic monophosphorothioate, Rp-isomer Rp-8-Br-(3-Tp)ET-cGMPS TABLE 14-continued Structures of novel monomeric precursor compounds according to the invention.

| En- try | Com- pound | Structure |
|---|---|---|
| 24 | 8-Bromo-(2-naphthyl-1,N²-etheno)guanosine-3',5'-cyclic monophosphorothioate, Rp-isomer | <br>Rp-8-Br-(2-N)ET-cGMPS |
| 25 | 8-Bromo-(α-methyl-β-phenyl-1,N²-etheno)guanosine-3',5'-cyclic monophosphorothioate, Rp-isomer | <br>Rp-8-Br-αMβP-ET-cGMPS |
| 26 | 1-Benzyl-8-bromoguanosine-3',5'-cyclic monophosphorothioate, Rp-isomer | <br>Rp-1-Bn-8-Br-cBMPS |

TABLE 14-continued

Structures of novel monomeric precursor compounds according to the invention.

| En-try | Com-pound | Structure |
|--------|-----------|-----------|
| 27 | 8-Thioguanosine-3',5'-cyclic monophosphorothioate, Rp-isomer | (Rp-8-T-cGMPS) |
| 28 | 8-(4-Isopropyl-phenylthio)guanosine-3',5'-cyclic monophosphorothioate, Rp-isomer | Rp-8-pIPrPT-cGMPS |
| 29 | 8-Carboxymethylthioguanosine-3',5'-cyclic monophosphorothioate, Rp-isomer | Rp-8-CMT-cGMPS |

TABLE 14-continued

Structures of novel monomeric precursor compounds according to the invention.

| En- try | Com- pound | Structure |
|---|---|---|
| 30 | 8-(2-Aminophenylthio)guanosine-3', 5'-cyclic monophosphorothioate, Rp-isomer | Rp-8-oAPT-cGMPS |
| 31 | 8-Phenyl-amiodomethylthioguanosine-3',5'-cyclic monophosphorothioate, Rp-isomer | Rp-8-PAmdMT-cGMPS |
| 32 | 8-Carboxymethylthio-β-phenyl-1,$N^2$-ethenoguanosine-3',5'-cyclic monophosphorothioate, Rp-isomer | Rp-8-CMT-PET-cGMPS |

TABLE 14-continued

Structures of novel monomeric precursor compounds according to the invention.

| En-try | Com-pound | Structure |
|---|---|---|
| 33 | β-Phenyl-1,N²-etheno-8-phenylamidomethyl-thioguanosine-3′,5′-cyclic monophosphorothioate, Rp-isomer | <br>Rp-PET-8-PAmdMT-cGMPS |
| 34 | 8-(4-Hydroxyphenylthio)-β-phenyl-1,N²-ethenoguanosine-3′,5′-cyclic monophosphorothioate, Rp-isomer | <br>Rp-8-pHPT-PET-cGMPS |
| 35 | 8-(4-Isopropylphenylthio)-β-phenyl-1,N²-ethenoguanosine-3′,5′-cyclic monophosphorothioate, Rp-isomer | <br>Rp-8-pIPrPT-PET-cGMPS |

TABLE 14-continued

Structures of novel monomeric precursor compounds according to the invention.

| En-try | Com-pound | Structure |
|---|---|---|
| 36 | 8-(2-Aminophenylthio)-β-phenyl-1,N²-ethenoguanosine-3',5'-cyclic monophosphorothioate, Rp-isomer | <br>Rp-8-oAPT-PET-cGMPS |
| 37 | β-Phenyl-1,N²-etheno-8-thioguanosine-3',5'-cyclic monophosphorothioate, Rp-isomer | <br>Rp-PET-8-T-cGMPS |
| 38 | 8-(4-Isopropyl-phenylthio)guanosine-3',5'-cyclic monophosphorothioate, Rp-isomer | <br>Rp-8-pIPrPT-cGMPS |

TABLE 14-continued

Structures of novel monomeric precursor compounds according to the invention.

| En-try | Com-pound | Structure |
|---|---|---|
| 39 | β-(4-Azidophenyl)-1,$N^2$-etheno-8-bromoguanosine-3',5'-cyclic monophosphorothioate, Rp-isomer | <br>Rp-4-N₃-PET-8-Br-cGMPS |
| 40 | 8-(2-Aminoethyl)-(octaethoxy)-amiodomethylthioguanosine-3',5'-cyclic monophosphorothioate, Rp-isomer | <br>Rp-8-AE-(EO)₈-AmdMT-cGMPS |
| 41 | 8-(3-Aminopropyl)-(pentaethoxy)-methylamidomethylthio-guanosine-3',5'-cyclic monophosphorothioate, Rp-isomer | <br>Rp-8-APr-(EO)₅-MAmdMT-cGMPS |

TABLE 14-continued

Structures of novel monomeric precursor compounds according to the invention.

| En-try | Com-pound | Structure |
|---|---|---|
| 42 | 8-Azido-methylamiodoethylthioguano-sine-3',5'-cyclic monophosphorothioate, Rp-isomer | Rp-8-N₃-MAmdET-cGMPS |
| 43 | 8-(4-(Propargyloxy-(hexaethoxy)-methyl)-[1,2,3]-triazole-1-yl)-methylamioethylthioguanosine-3',5'-cyclic monophosphorothioate, Rp-isomer | 8-(Rp-4-(PargO-(EO)₆-Me)-[1,2,3]-Tz-1)-MAmdET-cGMPS |
| 44 | 8-Bromo-1-(3-carboxypropyl)guanosine-3',5'-cyclic monophosphorothioate, Rp-isomer | Rp-8-Br-1-CPr-cGMPS |

TABLE 14-continued

Structures of novel monomeric precursor compounds according to the invention.

| En-try | Com-pound | Structure |
|---|---|---|
| 45 | 8-Bromo-δ-1,N²-butyrylguanosine-3',5'-cyclic monophosphorothioate, Rp-isomer | Rp-8-Br-δ-1,N²-But-cGMPS |
| 46 | 1-[Aminomethyl-(pentaethoxy)-propylamidopropyl]-8-bromoguanosine-3',5'-cyclic monophosphorothioate, Rp-isomer | Rp-1-AM-(EO)₅-PrAmdPr-8-Br-cGMPS |
| 47 | 8-Phenylguanosine-3',5'-cyclic monophosphorothioate, Rp-isomer | Rp-8-Phe-cGMPS |

TABLE 14-continued

Structures of novel monomeric precursor compounds according to the invention.

| En- try | Com- pound | Structure |
|---------|-----------|-----------|
| 48 | 8-(2-Furyl)guanosine-3',5'- cyclic monophosphorothioate, Rp-isomer | <br>Rp-8-(2-Fur)-cGMPS |
| 49 | 8-(4-Chlorophenyl)guanosine-3', 5'-cyclic monophosphorothioate, Rp-isomer | <br>Rp-8-pCP-cGMPS |
| 50 | 8-Phenyl-β-phenyl-1,N$^2$- ethenoguanosine-3',5'-cyclic monophosphorothioate, Rp- isomer | <br>Rp-8-Phe-PET-cGMPS |

TABLE 14-continued

Structures of novel monomeric precursor compounds according to the invention.

| En-try | Com-pound | Structure |
|---|---|---|
| 51 | 8-(4-Chlorophenyl)-β-phenyl-1,N²-ethenoguanosine-3',5'-cyclic monophosphorothioate, Rp-isomer | RP-8-pCP-PET-cGMPS |
| 52 | 8-(4-Chlorophenyl-sulfoxide)guanosine-3',5'-cyclic monophosphorothioate, Rp-isomer | Rp-8-pCPS(O)-cGMPS |
| 53 | 8-(4-Chlorophenyl-sulfonyl)guanosine-3',5'-cyclic monophosphorothioate, Rp-isomer | Rp-8-pCPS(O)₂-cGMPS |

TABLE 14-continued

Structures of novel monomeric precursor compounds according to the invention.

| En-try | Com-pound | Structure |
|---|---|---|
| 54 | 8-(4-Chlorophenylsulfonyl)-β-phenyl-1,N²-ethenoguanosine-3',5'-cyclic monophosphorothioate, Rp-isomer | Rp-8-pCPS(O)₂-PET-cGMPS |

As described above, the compounds according to the present invention may further be labelled, according to well-known labelling techniques. For example, fluorescent dyes may be coupled to the compounds in order to, but not limited to, localize the intracellular distribution of cyclic nucleotide binding proteins in living cells by means of confocal or other microscopy, for fluorescence correlation spectrometry, for fluorescence energy transfer studies, or for determination of their concentration in living cells.

It should be understood that hydrates of the compounds are also within the scope of the present invention.

Instead of or additional to fluorescent dyes the compounds according to the inventions may be labelled with (radio) nuclides. The person skilled in the art knows many techniques and suitable isotopes that can be used for this.

As described above, the invention also comprises PEGy-lated forms of the specified compounds, wherein PEGy-lation is generally known to greatly improve water solubility, pharmacokinetic and biodistribution properties.

The invention further comprises prodrug forms of the described compounds, wherein the negative charge of the equatorially modified phosphate moiety is masked by a bio-activatable protecting group. It is widely accepted that such structures increase lipophilicity and with that, membrane-permeability and bioavailability resulting in a 10-1000 fold enhanced potency compared to the mother-compound. Such bio-activatable protecting groups can be introduced according to well known techniques of the art and include, but are not limited to acetoxymethyl, propionyloxymethyl, butyryloxymethyl, pivaloyloxymethyl, acetoxyethyl, acetoxybutyl, acetoxyisobutyl. Non limiting examples of corresponding residue R8 according to the invention are acetoxymethylthio, propionyloxymethylthio and butyryloxymethylthio. More labile examples of protecting groups include alkyl or aryl groups as well as substituted alkyl or aryl groups. Non limiting examples for chemically labile protection groups of the R8 position are methyl, ethyl, 2-cyanoethyl, propyl, benzyl, phenyl and polyethylene glycol. These compounds are inactive per se, but extremely membrane-permeable, leading to strongly increased intrac-ellular concentrations. Upon hydrolysis of the ester bond, the biologically active mother compounds are released.

Compounds according to the invention can also feature a photolysable group (also-called "caged"- or photo-activatable protecting group), which can be introduced according to well known techniques of the art. For example, but not limited to, caged groups may be coupled to an R8 thio-function, leading to compounds with significantly increased lipophilicity and bioavailability. Non limiting examples for caged groups are o-nitro-benzyl, 1-(o-nitrophenyl)-ethyl-idene, 4,5-dimethoxy-2-nitro-benzyl, 7-dimethylamino-cou-marin-4-yl (DMACM-caged), 7-diethylamino-coumarin-4-yl (DEACM-caged) and 6,7-bis(carboxymethoxy) coumarin-4-yl)methyl (BCMCM-caged).

The compounds according to the present invention can also be immobilized to insoluble supports, such as, but not limited to, agarose, dextran, cellulose, starch and other carbohydrate-based polymers, to synthetic polymers such as polacrylamide, polyethyleneimine, polystyrol and similar materials, to apatite, glass, silica, gold, graphene, fullerenes, carboranes, titania, zirconia or alumina, to the surface of a chip suitable for connection with various ligands.

The compounds according to the present invention can also be encapsulated within nanoparticles or liposomes for directed or non-directed delivery and release purposes of the compounds as described in the literature.[13]

Further, the compounds according to the present invention are suitable for use as research tool compound, preferably as research tool compound in regard of a disease or disorder, preferably a disease or disorder selected from the group consisting of retinal disease or disorder or neuronal or neurodegenerative disease or disorder.

The terms "research tool" or "research tool compound" as used herein defines any experimental use in laboratory and preclinical research of a compound, and particularly excludes any use in humans as well as any use in the prophylaxis and/or medical treatment. Particularly, the said terms relate to any experimental use in laboratory and preclinical research of a compound, wherein the compound is not applied in human, but used in a laboratory and/or preclinical setting to study a disease or disorder, preferably a disease or disorder selected from the group consisting of retinal disease or disorder or neuronal or neurodegenerative disease or disorder. The compounds according to the present invention are suitable for use in the treatment of a disease or disorder, preferably a disease or disorder selected from the group consisting of retinal disease or disorder or neuronal or neurodegenerative disease or disorder.

It is to be understood herein that the treatment of a pathology, condition or disorder also includes the prevention thereof, even if not explicitly mentioned, unless specifically otherwise indicated.

Preferably the equatorially modified cGMP-analogues of the invention are used for treating or preventing a disease or condition of the retina. Diseases and conditions of the retina are preferably treated with equatorially modified cGMP analogues that inhibit the disease-related unbalanced cGMP-system, and include rare hereditary diseases of the retina such as retinitis pigmentosa, Stargardt's disease, fundus flavimaculatus, juvenile Best's disease, adult vitelliform fove-omacular dystrophy (adult vitelliform degeneration), familial drusen (North Carolina macular dystrophy), Bietti's crystalline dystrophy, progressive cone dystrophies, Alport's syndrome, benign familial fleck retina, Leber's congenital amaurosis, congenital monochromatism and hereditary macular dystrophies.

In addition, these equatorially modified cGMP-analogues of the invention may be used to treat secondary pigmentary retinal degeneration as it occurs in a number of metabolic and neurodegenerative diseases, various syndromes and other eye diseases, including: retinitis pigmentosa and hearing loss also associated with Usher syndrome, Waardenburg's syndrome, Alström's syndrome, Alport's syndrome, Refsum's syndrome, and other systemic conditions, all of which have their own systemic manifestations, short stature, renal dysfunction, and polydactyly are some signs of Bardet-Biedl syndrome or Laurence-Moon syndrome when associated with pigmentary retinopathy, the mucopolysaccharidoses may be associated with retinitis pigmentosa (e.g., Hurl-er's syndrome, Scheie's syndrome, Sanfilippo's syndrome), as well as the mitochondrial disorder Kearns-Sayre syndrome. In addition to those mentioned above, these include: Friedreich's ataxia, mucopolysaccharidosis, muscular dystrophy (myotonic dystrophy), Batten's syndrome, Bassen-Kornzweig syndrome, homocystinuria, oxalosis, eye and retinal trauma, glaucoma with retinal pigment epithelial changes, end-stage chloroquine retinopathy, end-stage thioridazine retinopathy, end-stage syphilitic neuroretinitis and cancer-related retinopathy. These equatorially modi-fled cGMP-analogues of the invention may also be used to treat other common diseases of the retina such as e.g. diabetic retinopathy, age related macular degeneration, macular Hole/Pucker, ocular malignancies, such as retinoblastoma, retinal detachment and river blind-ness/Onchocerciasis.

Furthermore the equatorially modified cGMP-analogues of the invention may be used to treat entirely different conditions that are associated with the disease-related unbalanced cGMP-system such as neuronal or neurodegenerative disorders, stroke, anosmia, inflammatory and neu-ropathic pain, axonal regrowth and recovery after spinal cord injury. The equatorially modified cGMP-analogues of the invention may also be used to treat cardiovascular diseases, hypotension, acute shock, and cancer. This also includes certain parasitic diseases like malaria, sleeping disease (African trypanosomiasis), and Chagas disease, in which the parasite survival is critically depending on the active cGMP-system.

In another aspect, the invention relates to a method for treating or preventing any of the above pathologies, conditions or disorders by administration of a therapeutically or prophylactically effective amount of an equatorially modi-fied cGMP-analogue of the invention to a subject in need of prophylaxis or therapy.

The invention is further illustrated by the following examples describing preferred embodiments of the present invention which are, however, not intended to limit the invention in any way.

Examples

1. Compound Synthesis

General Experimental Methods

All applied solvents and reagents were available from commercial suppliers. Rp-8-Br-cGMPS and Rp-8-Br-PET-cGMPS were available from Biolog Life Science Institute (Bremen, Germany). Solvents used were specified as analytical or hplc grade. Dimethyl sulfoxide was stored over activated molecular sieves for at least two weeks before use. Chromatographic operations were performed at ambient temperature. Both reaction progress and purity of isolated products were determined by reversed phase hplc (RP-18, ODS-A-YMC, 120-5-11, 250×4 mm, 1.5 mL/min), wherein UV detection was performed either at 263 nm, an intermediate wavelength suitable to detect most cyclic GMP products and—impurities, or at the $\lambda_{max}$ of the particular starting material or product. Syntheses were typically performed in a 20-200 µmol scale in 2 mL polypropylene reaction vials with screw cap (reactions requiring inert gas atmosphere and/or degassing were performed in round bottom flasks (typically 10 or 25 mL)). Dissolution of poorly soluble reactants was achieved through sonification or heating (70° C.) prior to addition of reagents. In case dissolution was not elicited by these techniques, which mainly applied to some cGMP analogues carrying a PET-moiety, the suspension was used. Purification of products was accomplished by preparative reversed phase hplc (RP-18, ODS-A-YMC, 12 nm-S-10, 250×16 mm, UV 254 nm). The eluent composition is described in the particular synthetic example and, unless stated otherwise, can be used for analytical purposes as well. Desalting of products was accomplished by repeatedly freeze-drying or by preparative reversed phase hplc (RP-18, ODS-A-YMC, 12 nm-S-10, 250×16 mm, UV 254 nm) according to standard procedures for nucleotides. Solutions were frozen at −70° C. for 15 min prior to evaporation, in case a speedvac concentrator was used to remove the solvent. Products were either isolated as sodium or triethylammonium salt, depending on the applied buffer. Yields refer to the fraction of isolated product featuring the reported purity. They were calculated from UV-absorbance at the $\lambda_{max}$, measured on a JASCO V-650 Spectrophotometer (JASCO Germany GmbH, Gross-Umstadt, Germany) according to Lambert-Beer's law. Extinction coefficients were estimated from literature known values of structurally related compounds. Mass spectra were obtained with an Esquire LC 6000 spectrometer (Bruker Daltronics, Bremen, Germany) in the ESI-MS mode with 50% water/50% methanol as matrix.

Experimental Procedures for the Preparation of 8-Thio-Substituted Equatorially Modified Guanosine-3',5'-Cyclic Monophosphate Analogues

General Procedure A

In a typical experiment the corresponding thiol reactant (8 eq) and NaOH (2 M, 4 eq) were added successively to a solution of the corresponding 8-Br-substituted equatorially modified cGMP analogue (sodium salt, 65 mM, 1 eq) in $H_2O$/i-PrOH (1:1, v/v). The reaction mixture was heated to 90° C. and stirred until the bromide starting material was completely consumed or no further reaction progress was observed. The solution was then allowed to reach room temperature, neutralized with HCl (1 M) and the solvent was removed through high vacuum evaporation with a speedvac concentrator. The residue was dissolved in water (1 mL) and washed with MTBE (3×).* The aqueous phase was evaporated under reduced pressure using a rotary evaporator, the residue redissolved in water, subjected to preparative reversed phase hplc and desalted, giving the 8-thio-substituted equatorially modified cGMP analogue.

*In case the residue was not soluble in water, the obtained suspension was washed with MTBE and (if necessary) diluted with MeOH to dissolve remaining precipitate.

General Procedure A2

In a typical experiment the corresponding thiol(ate) reactant (4.5 eq) was added to a solution of the corresponding 8-Br-substituted equatorially modified cGMP analogue (sodium salt, 65 mM, 1 eq) in $H_2O$/i-PrOH (1:1, v/v). The reaction mixture was stirred at room temperature until the bromide starting material was completely consumed or no further reaction progress was observed. The solution was then adjusted to pH 6 with NaOH (10%) and the solvent was removed through high vacuum evaporation with a speedvac concentrator. The residue was dissolved in water (1 mL) and washed with $CH_2Cl_2$ (3×). The aqueous phase was evaporated under reduced pressure using a rotary evaporator, the residue redissolved in water, subjected to preparative reversed phase hplc and desalted, giving the 8-thio-substituted equatorially modified cGMP analogue.

General Procedure B

In a typical experiment a solution of the 8-Br-substituted equatorially modified cGMP analogue (sodium salt, 87 mM, 1 eq) was added portionwise over 2 h to a suspension of the corresponding dithiol (50 mM in water/i-PrOH, 2:3, v/v, 10 eq) and NaOH (2 M, 5 eq). The reaction mixture was heated to 90° C. and stirred until the bromide starting material was completely consumed or no further reaction progress was observed. The solvent was removed through high vacuum evaporation with a speedvac concentrator. The residue was suspended in water (1 mL), neutralized with HCl (1 M) and filtered. The crude product solution was subjected to preparative reversed phase hplc and desalted, giving the thiol analogue.

General Procedure C

In a typical experiment NaOH (2 M, 16 eq) and the corresponding thiol reactant (8 eq) were added successively to a solution of the 8-Br-substituted cGMP analogue (sodium salt, 200 mM, 1 eq) in borate buffer (100 mM, pH 12). The reaction mixture was heated to 90° C. and stirred until the bromide starting material was completely consumed or no further reaction progress was observed. The solution was then allowed to reach room temperature and neutralized with HCl (1 M). The solvent was removed under reduced pressure using a rotary evaporator. The residue was dissolved in water (1 mL), subjected to preparative reversed phase hplc and desalted.

General Procedure D

In a typical experiment N,N-diisopropylethylamine (2 eq) and the corresponding bromide (1 eq) were added successively to a solution of the 8-SH-substituted equatorially modified cGMP analogue (sodium or triethylammonium salt, 100 mM, 1 eq) in DMSO. The reaction mixture was stirred until the thiol starting material was completely consumed or no further reaction progress was observed. The solvent was removed through high vacuum evaporation with a speedvac concentrator. The residue was dissolved in water (1 mL), washed with ethyl acetate (3×), subjected to preparative reversed phase hplc and desalted.

General Procedure E

For the formation of dimeric equatorially modified cGMP analogues general Procedure D was followed using N,N-diisopropylethylamine (2 eq), the corresponding bis-bromide spacer (0.5 eq) and the 8-SH-substituted equatorially modified cGMP analogue (sodium or triethylammonium salt, 100 mM, 1 eq) in DMSO.

Experimental Procedure for the Transformation of Carboxylic Acid Ester Functionalized Equatorially Modified Guanosine-3',5'-Cyclic Monophosphate Analogues into the Corresponding Carboxylic Acid or Amide

General Procedure F

In a typical experiment NaOH (2 M, 10 eq) was added to a solution of the corresponding ester (80 mM, 1 eq) in water/MeOH (1:1, v/v). The reaction mixture was stirred until the ester starting material was completely consumed or no further reaction progress was observed. The solution was then neutralized with HCl (1 M) and the solvent was removed under reduced pressure using a rotary evaporator. The residue was dissolved in water (1 mL), subjected to preparative reversed phase hplc and desalted, giving the carboxylic acid analogue.

General Procedure G

In a typical experiment the corresponding ester (1 eq) was dissolved in excess methanolic ammonia (4.2 M, 200 eq). The reaction mixture was stirred until the starting material was completely consumed or no further reaction progress was observed. The solvent was removed through high vacuum evaporation with a speedvac concentrator. The residue was dissolved in water (1 mL), neutralized with HCl (1 M) and filtered through a syringe filter. The crude product was subjected to preparative reversed phase hplc and desalted, giving the carboxylic acid amide analogue.

Experimental Procedures for the Formation of Amide Bonds with Equatorially Modified Guanosine-3',5'-Cyclic Monophosphate Analogues

General Procedure H

In a typical experiment HOBt (1.1 eq), N,N-diisopropylethylamine (2.2 eq) and EDC (1.1 eq) were added successively to a solution of the corresponding acid-substituted equatorially modified cGMP analogue (100 mM in DMSO, 1 eq) and the corresponding amine (1.1 eq)*. The reaction mixture was stirred until the starting material was completely consumed or no further reaction progress was observed. The solvent was removed through high vacuum evaporation with a speedvac concentrator. The residue was dissolved in water (1 mL) and washed with ethyl acetate (5×). The aqueous phase was evaporated under reduced pressure using a rotary evaporator, redissolved in water, subjected to preparative reversed phase hplc and desalted, giving the coupled equatorially modified cGMP analogue.

*The less valuable reactant was added in slight excess, thus for the reaction with reversed functions the amine-substituted equatorially modified cGMP analogue (100 mM in DMSO, 1 eq) and the acid reactant (1.1 eq) were used.

General Procedure I

In a typical experiment HOBt (1.1 eq), N,N-diisopropylethylamine (2.2 eq) and EDC (1.1 eq) were added successively to a solution of the corresponding acid-substituted equatorially modified cGMP analogue (100 mM in DMSO, 1 eq) and the corresponding bis-amino spacer (0.5 eq). Workup was performed as described in general procedure H, giving the dimeric equatorially modified cGMP analogue.

General Procedure J

In a typical experiment N,N-diisopropylethylamine (2.2 eq) and PyBOP (1.1 eq) were added successively to a solution of the corresponding carboxylic acid-substituted equatorially modified cGMP analogue (100 mM in DMSO, 1 eq) and the corresponding amine (1.1 eq)*. The reaction mixture was stirred until the starting material was completely consumed or no further reaction progress was observed (usually <10 min). Water (100 μL) was added, stirring was continued for 10 min and the solvent was removed through high vacuum evaporation with a speedvac concentrator. The residue was dissolved in water (1 mL), if necessary the pH was adjusted to 6 with NaOH (2 M) or HCl (1 M) and the solution washed with ethyl acetate (5×). The aqueous phase was evaporated under reduced pressure using a rotary evaporator, redissolved in water, subjected to preparative reversed phase hplc and desalted, giving the coupled equatorially modified cGMP analogue.

*The less valuable reactant was added in slight excess, thus for the reaction with reversed functions the amine-substituted equatorially modified cGMP analogue (100 mM in DMSO, 1 eq) and the acid reactant (1.1 eq) were used.

General Procedure K

In a typical experiment a solution of the corresponding carboxylic acid-substituted equatorially modified cGMP analogue (100 mM in DMSO, 1 eq) was added portionwise over 40 min to a solution of the bis-amino spacer (400 mM in DMSO, 5 eq), N,N-diisopropyethylamine (2.2 eq) and PyBOP (1.1 eq). More PyBOP (1 eq) was added and the reaction mixture was stirred until the starting material was completely consumed or no further reaction progress was observed (usually <10 min). Workup was performed as described in general procedure J, giving the monomeric equatorially modified cGMP analogue coupling product.

General Procedure L

General procedure J was followed using the corresponding acid-substituted equatorially modified cGMP analogue (100 mM in DMSO, 1 eq), the bis-amino spacer (0.5 eq), N,N-diisopropylethylamine (2.2 eq) and PyBOP (1.1 eq) to obtain the dimeric equatorially modified cGMP analogue.

General Procedure M

General procedure J was followed using the corresponding amine-substituted equatorially modified cGMP analogue (33 mM in DMSO, 1 eq), the linker tri-acid (0.3 eq), N,N-diisopropylethylamine (2 eq) and PyBOP (1.3 eq) to obtain the trimeric equatorially modified cGMP analogue.

General Procedure N

General procedure J was followed using the corresponding amine-substituted equatorially modified cGMP analogue (diisopropylethylammonium salt, 50 mM in DMSO, 1 eq)*, the linker tetra-acid (tetra-diisopropylethylammonium salt, 0.25 eq)*, N,N-diisopropylethylamine (3 eq) and PyBOP (1.3 eq) to obtain the tetrameric equatorially modified cGMP analogue.

*To transform the reactants into the diisopropylethylammonium salt they were subjected to N,N-diisopropylethylamine (3 eq per acidic function) in water (0.1-0.3 M) and evaporated to dryness using a speedvac concentrator at high vacuum.

Experimental Procedures for the Preparation of 8-Sulfonyl- and 8-Sulfoxide-Substituted Equatorially Modified Guanosine-3',5'-Cyclic Monophosphate Analogues

General Procedure O

In a typical experiment a solution of OXONE© (180 mM, 5 eq) in NaOAc buffer (2 M, pH 4.2) was added dropwise to a solution of the corresponding 8-thio-substituted guanosine analogue (40 mM, 1 eq) in water/MeOH (1:1, v/v). The reaction mixture was stirred until the thio starting material was completely consumed or no further reaction progress was observed. The solution was then neutralized with NaOH (2 M) and filtered through a syringe filter. The solvent was removed under reduced pressure using a rotary evaporator. The residue was dissolved in water (1 mL), subjected to preparative reversed phase hplc and desalted, giving the 8-sulfonyl-substituted guanosine analogue. Transformation to the corresponding equatorially modified cGMP analogue was then performed according to established thiophosphorylation protocol[2b].

General Procedure P

General procedure O was followed, favoring the formation of the 8-sulfoxide-substituted equatorially modified cGMP analogue through shorter reaction time and decreased equivalents of oxidizing agent OXONE© (1.5 eq).

Experimental Procedure for the Generation of 8-Azidoalkylthio-Substituted Equatorially Modified Guanosine-3',5'-Cyclic Monophosphate Analogues

General Procedure Q

In a typical experiment NaN$_3$ (22.5 eq) was added portionwise over 5 h to a solution of 1,2-dibromoalkane (1.5 M, 15 eq) in DMF in an amber flask. The reaction mixture was stirred for 23 h and the 8-SH-substituted equatorially modified cGMP analogue (triethylammonium salt, 1 eq) as well as N,N-diisopropylethylamine (1 eq) were added successively. Stirring was continued until the equatorially modified cGMP analogue starting material was completely consumed or no further reaction progress was observed (usually about 1 h). The solvent was removed through high vacuum evaporation with a speedvac concentrator. The residue was dissolved in water (1 mL) and washed with MTBE (5×). The aqueous phase was evaporated under reduced pressure using a rotary evaporator, the residue was redissolved in water, subjected to preparative reversed phase hplc and desalted, giving the 8-azidoalkylthio-substituted analogue.

Experimental Procedures for the [3+2] Cycloaddition of Azides and Terminal Alkynes on Equatorially Modified Guanosine-3',5'-Cyclic Monophosphate Analogues

General Procedure R

In a typical experiment a solution of the corresponding azide (0.5 M in $CH_2Cl_2$, 1.1 eq) was added to the alkyne-substituted equatorially modified cGMP analogue (40 mM in $H_2O$, 1 eq) in an amber flask. Bromotris(triphenylphosphine)copper(I) ([$Cu(PPh_3)_3Br$]) (0.05 eq) was added and the reaction mixture was stirred until the alkyne starting material was completely consumed or no further reaction progress was observed. The mixture was diluted with water (to 1.5 mL) and washed with $CH_2Cl_2$ (3×). The aqueous phase was evaporated under reduced pressure using a rotary evaporator, the residue was redissolved in water, subjected to preparative reversed phase hplc and desalted, giving the triazole-containing product.

General Procedure S

In a typical experiment [$Cu(PPh_3)_3Br$] (0.05 eq) was added to a solution of the corresponding azide (13 mM, 1 eq) and the corresponding alkyne (13 mM, 1 eq) in water/N,N-diisopropylethylamine (7:1, v/v) in an amber flask. The reaction mixture was stirred at 65° C. until the starting material was completely consumed or no further reaction progress was observed. The solvent was removed through high vacuum evaporation with a speedvac concentrator. The residue was dissolved in water (1 mL) and washed with $CH_2Cl_2$ (3×). The aqueous phase was evaporated under reduced pressure using a rotary evaporator, the residue was redissolved in water, subjected to preparative reversed phase hplc and desalted, giving the triazole-containing product.

General Procedure T

General Procedure S was followed, using [$Cu(PPh_3)_3Br$] (0.05 eq), the corresponding azide-substituted equatorially modified cGMP analogue (23 mM, 1 eq) and the corresponding bis-alkyne (12 mM, 2 eq) in water/N,N-diisopropylethylamine (8:1, v/v). Conditions were chosen to obtain both the monomeric and the dimeric triazole-containing product.

General Procedure U

General Procedure S was followed, using [$Cu(PPh_3)_3Br$] (0.05 eq), the corresponding azide-substituted equatorially modified cGMP analogue (33 mM, 1 eq) and the corresponding bis-alkyne (16 mM, 0.5 eq) in water/N,N-diisopropylethylamine (10:1, v/v) to obtain the dimeric triazole-containing product.

Experimental Procedure for the Transformation of Azido-Substituted Equatorially Modified Guanosine-3',5'-Cyclic Monophosphate Analogues into the Corresponding Amines

General Procedure V

In a typical experiment a solution of the azido-substituted equatorially modified cGMP analogue (2.5 mM in water, 1 eq) in an amber flask was adjusted to pH 10 by addition of triethylamine and cooled to 10° C. DL-Dithiothreitol (5 eq) was added and the reaction mixture was stirred until the azide starting material was completely consumed or no further reaction progress was observed (usually <20 min). The mixture was evaporated to dryness under reduced pressure using a rotary evaporator. The residue was dissolved in water (1 mL), subjected to preparative reversed phase hplc and desalted, giving the amine-substituted equatorially modified cGMP analogue.

Experimental Procedure for the Suzuki Cross-Coupling of Br-Substituted Equatorially Modified Guanosine-3',5'-Cyclic Monophosphate Analogues with Organoboronic Acids

General Procedure W

In a typical experiment aqueous $K_2CO_3$ (2 M, 3 eq) and Pd(dppf)$Cl_2$ (0.05 eq) were added successively to a solution of the Br-substituted equatorially modified cGMP analogue (52 mM, 1 eq) and the boronic acid (72 mM, 1.4 eq) in EtOH/$H_2O$ (1:1, v/v). The reaction mixture was immediately degased applying three cycles of freeze-pump-thaw technique and stirred at 90° C. under argon until the bromide starting material was completely consumed or no further reaction progress was observed. The solvent was removed through high vacuum evaporation with a speedvac concentrator. The residue was suspended in water and washed with $CHCl_3$ (3×). Methanol was added until dissolution of the precipitate (up to $H_2O$/MeOH=1:1). If an organic phase, containing residual $CHCl_3$, emerged from this composition, it was separated. The aqueous phase was then filtered through a Macherey-Nagel Chromafix C 18 (S) 270 mg cartridge (preconditioned with 10 mL of MeOH, 50% MeOH and 30% MeOH respectively) and rinsed with 30% MeOH (6 mL). The solvent was removed under reduced pressure using a rotary evaporator. The residue was dissolved in water (1 mL), subjected to preparative reversed phase hplc and desalted, giving the cross-coupling product.

All solvents used, were degassed through sonification under reduced pressure prior to the experiment.

General Procedure X (Preparation of Bis Boronic Acid Reagent 4-B(OH)$_2$PhS-(EO)$_5$—(CH$_2$)$_2$-4-SPhB(OH)$_2$)

In a typical experiment N,N-diisopropylethylamine (2 eq) was added to a solution of 4-mercaptophenylboronic acid (0.2 M, 1 eq) and Br-(EO)$_5$—(CH$_2$)$_2$—Br (0.5 eq) in DMF. The reaction mixture was stirred until the boronic acid starting material was completely consumed or no further reaction progress was observed. The solvent was removed through high vacuum evaporation with a speedvac concentrator. The residue was dissolved in methanol (1 mL) and subjected to preparative reversed phase hplc (62% MeOH) giving 4-B(OH)$_2$PhS-(EO)$_5$—(CH$_2$)$_2$-4-SPhB(OH)$_2$ (34% yield).

Experimental Procedure for the Preparation of 1, $N^2$-Functionalized Equatorially Modified Guanosine-3',5'-Cyclic Monophosphate Analogues

General Procedure Y

In a typical experiment DBU (7 eq) and the corresponding 2-bromo-aceto-reactant (3.5 eq) were added successively to a solution of the corresponding equatorially modified cGMP analogue (50 mM, 1 eq) in DMSO. The reaction mixture was stirred under exclusion of light until the equatorially modified cGMP analogue starting material was completely consumed or no further reaction progress was observed. The solvent was removed through high vacuum evaporation with a speedvac concentrator. The residue was dissolved in methanol (0.5 mL) and the pH adjusted to 6-7 with HCl (1 M). In case a precipitate was formed thereby, methanol was added to redissolve it. Otherwise, water was slowly added up until all components just remained soluble (max. H$_2$O/MeOH=5:1). The solution was subjected to preparative reversed phase hplc and desalted, giving the 1, N$^2$-etheno-functionalized equatorially modified cGMP analogue.

General Procedure Y2

In a typical experiment DBU (2 eq) and the corresponding alkyl bromoacetate-reactant (1.1 eq) were added successively to a solution of the corresponding equatorially modified cGMP analogue (100 mM, 1 eq) in DMSO. The reaction mixture was stirred until the equatorially modified cGMP analogue starting material was completely consumed or no further reaction progress was observed. The solvent was removed through high vacuum evaporation with a speedvac concentrator. The residue was dissolved in H$_2$O (0.5 mL) and the pH adjusted to 6-7 with HCl (1 M). The solution was subjected to preparative reversed phase hplc and desalted, giving the 1, N$^2$-acyl-functionalized equatorially modified cGMP analogue.

General Procedure Y3

In a typical experiment N,N-diisopropylethylamine (2 eq) and PyBOP (1.1 eq) were added successively to a solution of the corresponding 1-carboxyalkyl-substituted equatorially modified cGMP analogue (10 mM in DMSO, 1 eq). The reaction mixture was stirred until the equatorially modified cGMP analogue starting material was completely consumed or no further reaction progress was observed. Water (100 µL) was added, stirring was continued for 10 min and the solvent was removed through high vacuum evaporation with a speedvac concentrator. The residue was dissolved in water (1 mL), the pH adjusted to 5-6 with NaOH (2 M) and the solution washed with ethyl acetate (5×). The aqueous phase was evaporated under reduced pressure using a rotary evaporator, redissolved in water, subjected to preparative reversed phase hplc and desalted, giving the 1, N$^2$-acyl-functionalized equatorially modified cGMP analogue.

Experimental Procedures for the Preparation of 1-Substituted Equatorially Modified Guanosine-3',5'-Cyclic Monophosphate Analogues

General Procedure Z

In a typical experiment DBU (4 eq) and the corresponding bromide- (or iodide) reactant (4 eq) were added successively to a solution of the corresponding equatorially modified cGMP analogue (50-300 mM, 1 eq) in DMSO. The reaction mixture was stirred until the equatorially modified cGMP analogue starting material was completely consumed or no further reaction progress was observed. The solvent was removed through high vacuum evaporation with a speedvac concentrator. The residue was dissolved in H$_2$O (0.5 mL) and, in case the resulting solution was not neutral, the pH was adjusted to 7 with HCl (1 M). The solution was washed with ethyl acetate (4×). The aqueous phase was evaporated under reduced pressure using a rotary evaporator, the residue was redissolved in water, subjected to preparative reversed phase hplc and desalted, giving the 1-substituted equatorially modified cGMP analogue.

General Procedure Z2

In a typical experiment DBU (2 eq) and the corresponding dibromide-reactant (0.5 eq) were added successively to a solution of the corresponding equatorially modified cGMP analogue (15 mM, 1 eq) in DMSO. The reaction mixture was stirred at 90° C. until the equatorially modi-fled cGMP analogue starting material was completely consumed or no further reaction progress was observed. The solvent was removed through high vacuum evaporation with a speedvac concentrator. The residue was dissolved in H$_2$O (0.5 mL), the pH adjusted to 5-7 with HCl (1 M) and the solution was washed with ethyl acetate (4×). The aqueous phase was evaporated under reduced pressure using a rotary evapora-tor, the residue was redissolved in water, subjected to preparative reversed phase hplc and desalted, giving the 1-substituted dimeric equatorially modified cGMP analogue.

The invention is further illustrated by the figures and examples of describing preferred embodiments of the present invention (Table 15) which are, however, not intended to limit the invention in any way. Structural examples of novel compounds are depicted in the free acid form. After HPLC workup, compounds are obtained as salts of the applied buffer, but can be transformed to other salt forms or to the free acid by cation exchange according to standard procedures for nucleotides.

TABLE 15

Examples of novel equatorially modified polymer linked multimeric cGMP compounds according to the invention.

| Entry | Compound/Structure |
|---|---|
| 1 | Guanosine-3',5'-cyclic monophosphorothioate[Rp]-[8-thiomethylamido-(octaethoxy)-ethylamidomethylthio-8]-guanosine-3',5'-cyclic monophosphorothioate[Rp](Rp-cGMPS-8-TMAmd-(EO)$_8$-EAmdMT-8-Rp-cGMPS)<br><br>Using general procedure L, Rp-8-CMT-cGMPS was reacted with NH$_2$-(EO)$_8$-(CH$_2$)$_2$NH$_2$ to give the title compound.<br>Yield (Purity): 52% (>99%).<br>HPLC: (14% MeCN, 50 mM NaH$_2$PO$_4$ buffer, pH 6.8).<br>UV-VIS: $\lambda$max = 275 nm (pH 7), $\epsilon$ = 24660 (est.).<br>ESI-MS (+): m/z calculated for C$_{42}$H$_{65}$N$_{12}$O$_{22}$P$_2$S$_4$ ([M + H]$^+$): 1279.27, found: 1279.<br>ESI-MS (−): m/z calculated for C$_{42}$H$_{63}$N$_{12}$O$_{22}$P$_2$S$_4$ ([M − H]$^-$): 1277.25, found: 1277. |
| 2 | |

TABLE 15-continued

Examples of novel equatorially modified polymer linked multimeric cGMP compounds according to the invention.

| Entry | Compound/Structure |
|---|---|
| | β-Phenyl-1,N²-ethenoguanosine-3',5'-cyclic monophosphorothioate[Rp]-[8-thiomethylamido-(octaethoxy)-ethylamidomethylthio-8]-β-phenyl-1,N²-ethenoguanosine-3',5'-cyclic monophosphorothioate[Rp](PET-Rp-cGMPS-8-TMAmd-(EO)₈-EAmdMT-8-Rp-cGMPS-PET) Using general procedure L, Rp-8-CMT-PET-cGMPS was reacted with NH₂-(EO)₈-(CH₂)₂NH₂ to give the title compound. Yield (Purity): 57% (>99%). HPLC: (25% MeCN, 80 mM NaH₂PO₄ buffer, pH 6.8). UV-VIS: λmax = 272 nm (pH 7), ε = 72000 (est.). ESI-MS (+): m/z calculated for $C_{58}H_{73}N_{12}O_{22}P_2S_4$ ([M + H]⁺): 1479.33, found: 1479. ESI-MS (−): m/z calculated for $C_{58}H_{71}N_{12}O_{22}P_2S_4$ ([M + H]⁺): 1477.32, found: 1477. |
| 3 | β-1,N²-Acetylguanosine-3',5'-cyclic monophosphorothioate[Rp]-[8-thiomethylamido-(octaethoxy)-ethylamidomethylthio-8]-β-1,N²-acetylguanosine-3',5'-cyclic monophosphorothioate[Rp](β-1,N²-Ac-Rp-cGMPS-8-TMAmd-(EO)₈-EAmdMT-8-Rp-cGMPS-β-1,N²-Ac) Using general procedure C, Rp-β-1, N²-Ac-8-Br-cGMPS is reacted with mercaptoacetic acid to give the 8-carboxymethylthio-substituted analogue, which is transferred into the title compound applying general procedure L in the presence of NH₂-(EO)₈-(CH₂)₂NH₂. |

TABLE 15-continued

Examples of novel equatorially modified polymer linked multimeric cGMP
compounds according to the invention.

Entry Compound/Structure

4

β-Phenyl-1,N²-ethenoguanosine-3′,5′-cyclic monophosphorothioate[Rp]-[8-
thio-(pentaethoxy)-ethylthio-8]-β-phenyl-1,N²-ethenoguanosine-3′,5′-cyclic
monophosphorothioate[Rp](PET-Rp-cGMPS-8-T-(EO)₅-ET-8-Rp-cGMPS-PET)
Using general procedure E, Rp-PET-8-T-cGMPS was reacted with Br-(EO)₅-CH₂CH₂Br
to give the title compound.
Yield (Purity): 20% (>95%).
HPLC: (28% ACN, 50 mM NaH₂PO₄ buffer, pH 6.8).
UV-VIS: λmax = 272 nm (pH 7), ε = 40000 (est.).
ESI-MS (+): m/z calculated for C₄₈H₅₅N₁₀O₁₇P₂S₄ ([M + Et₃NH]⁺): 1233.21, found:
1233.
ESI-MS (−): m/z claculated for C₄₈H₅₃N₁₀O₁₇P₂S₄ ([M + H]⁻): 1231.19, found: 1231.

TABLE 15-continued

Examples of novel equatorially modified polymer linked multimeric cGMP compounds according to the invention.

Entry Compound/Structure

5

Guanosine-3′,5′-cyclic monophosphorothioate[Rp]-[8-thiomethylamido-(EO)$_n$-ethylamidomethylthio-8]-guanosine-3′,5′-cyclic monophosphorothioate[Rp] (Rp-cGMPS-8-TMAmd-(PEG)$_n$-EAmdMT-8-Rp-cGMPS)
Using general procedure L, Rp-8-CMT-cGMPS is reacted with NH$_2$-(EO)$_n$-(CH$_2$)$_2$NH$_2$ (with n = 4 to 50, preferably n = 4-20 or (EO)$_n$ referring to PEG polydispers 2000 Da) to give the title compound.

6

β-Phenyl-1,N$^2$-ethenoguanosine-3′,5′-cyclic monophosphorothioate[Rp]-[8-thiomethylamido-(EO)$_n$-ethylamidomethylthio-8]-β-phenyl-1,N$^2$-ethenoguanosine-3′,5′-cyclic monophosphorothioate[Rp](PET-Rp-cGMPS-8-TMAmd-(EO)$_n$-EAmdMT-8-Rp-cGMS-PET)
Using general procedure L, Rp-8-CMT-PET-cGMPS is reacted with NH$_2$-(EO)$_n$-(CH$_2$)$_2$NH$_2$ (with n = 4 to 50, preferably n = 4-20 or (EO)$_n$ referring to PEG polydispers 2000 Da) to give the title compound.

TABLE 15-continued

Examples of novel equatorially modified polymer linked multimeric cGMP
compounds according to the invention.

Entry  Compound/Structure

7

Guanosine-3',5'-cyclic monophosphorothioate[Rp]-[8-thio-(pentaethoxy)-
ethylthio-8]-guanosine-3',5'-cyclic monophosphorothioate[Rp](Rp-cGMPS-8-
T-(EO)₅-ET-8-Rp-cGMPS)
Using general prodcedure E, Rp-8-T-cGMPS is reacted with Br-(EO)₅-CH₂CH₂Br to give
the title compound.

8

Guanosine-3',5'-cyclic monophosphorothioate[Rp]-[8-thio-(dodecanyl)-thio-
8]-guanosine-3',5'-cyclic monophosphorothioate[Rp](Rp-cGMPS-8-T-(CH₂)₁₂-
T-8-Rp-cGMPS)
Using general procedure E, Rp-8-T-cGMPS is reacted with 1,12-dibromdodecane to
give the title compound.

TABLE 15-continued

Examples of novel equatorially modified polymer linked multimeric cGMP
compounds according to the invention.

| Entry | Compound/Structure |
|-------|-------------------|

9

8-Bromoguanosine-3',5'-cyclic monophosphorothioate[Rp]-[1,N²-etheno-β-
phenyl-4-yl-(1-[1,2,3]-triazole-4-yl)-methoxy-(hexaethoxy)-methyl-(4-(4-
[1,2,3]-triazole-1-yl)-β-phenyl-1,N²-etheno)]-8-bromoguanosine-3',5'-cyclic
monophosphorothioate[Rp](8-Br-Rp-cGMPS-ETP-p(1-[1,2,3]-Tz-4)-MeO-(EO)₆-
Me-p(4-[1,2,3]-Tz-1)-PET-Rp-cGMPS-8-Br)
Using general procedure U, Rp-4-N₃-PET-8-Br-cGMPS is reacted with bis-propargyl-
(EO)₇ to give the title compound.

10

Guanosine-3',5'-cyclic monophosphorothioate[Rp]-[8-thiomethylamido-
(octaethoxy)-ethylamidomethylthio-8]-β-phenyl-1,N²-ethenoguanosine-3',5'-
cyclic monophosphorothioate[Rp](Rp-cGMPS-8-TMAmd-(EO)₈-EAmdMT-8-Rp-
cGMPS-PET)
Using general procedure J, Rp-8-CMT-PET-cGMPS (1 eq) is reacted with Rp-8-AE-
(EO)₈-AmdMI-cGMPS (1 eq) to give the title compound.

TABLE 15-continued

Examples of novel equatorially modified polymer linked multimeric cGMP compounds according to the invention.

Entry Compound/Structure

11

Benzene-1,3,5-tri-[(8-amidomethyl-(pentaethoxy)-propylamiodomethylthio)guanosine-3',5'-cyclic monophosphorothioate[Rp]](Bn-1,3,5-tri(AmdPr-(OE)$_5$-MAmdMT-8-Rp-cGMPS)

Using general procedure M, Rp-8-APr-(EO)$_5$-MAmdMT-cGMPS is reacted with 1,3,5-benzenetricarboxylic acid to give the title compound.

TABLE 15-continued

Examples of novel equatorially modified polymer linked multimeric cGMP compounds according to the invention.

Entry    Compound/Structure

12

Ethylene glycol-bis(2-aminoether)-N,N,N′,N′-tetra-1[(8-methylamidoethylthio]guanosine-3′,5′-cyclic monophosphorothioate[Rp]](EG-N,N,N′,N′-tetra(8-MAmdET-Rp-cGMPS))

Using general procedure N, Rp-8-AET-cGMPS is reacted with ethylene glycol-bis(2-aminoethylether)-N,N,N′,N′-tetraacetic acid (EGTA) to give the title compound.

TABLE 15-continued

Examples of novel equatorially modified polymer linked multimeric cGMP compounds according to the invention.

| Entry | Compound/Structure |
|---|---|
| 13 | <br><br>Guanosine-3′,5′-cyclic monophosphorothioate[Rp]-[8-thioethylamidomethyl-(1-[1,2,3]-triazole-4-yl)-methoxy-(hexaethoxy)-methyl-(4-[1,2,3]-triazole-1-yl)-methylamidoethylthio-8]-guanosine-3′,5′-cyclic monophosphorothioate[Rp] (Rp-cGMPS-8-TEAmdM-(1-[1,2,3]-Tz-4)-MeO-(EO)₆-Me-(4-[1,2,3]Tz-1)-MAmdET-8-Rp-cGPS)<br>Using general procedure S. Rp-8-N₃-MAmdET-cGMPS (1 eq) is reacted with bis-propargyl-(EO)₆ (2 eq) to give the title compound and the PEGylated monomeric analogue. Decreasing equivalents of PEG reagent favors formation of the title product. |
| 14 | <br><br>Guanosine-3′,5′-cyclic monophosphorothioate[Rp]-[8-thioethylamidomethyl-(1-[1,2,3]-triazole-4-yl)-methoxy-(hexaethoxy)-methyl-(4-(4-[1,2,3]-triazole-1-yl)-β-phenyl-1,N²-etheno]-8-bromoguanosine-3′,5′-cyclic monophosphorothioate[Rp](Rp-cGMPS-8-TEAmdM-(1-[1,2,3]-Tz-4)-MeO-(EO)₆-Me-(4-[1,2,3]-Tz-1)-PET-8-Br-Rp-cGMPS) |

TABLE 15-continued

Examples of novel equatorially modified polymer linked multimeric cGMP
compounds according to the invention.

Entry  Compound/Structure

Using general procedure S, Rp-4-N₃-PET-8-Br-cGMPS (1 eq) is reacted with Rp-8-(4-
(PargO-(EO)₆-Me)-[1,2,3]-Tz-1)-MAmdET-cGMPS (1 eq) to give the title compound.

15

8-Bromoguanosine-3',5'-cyclic monophosphorothioate[Rp]-[1-(pentaethoxy)-
ethyl-1]-8-bromoguanosine-3',5'-cyclic monophosphorothioate[Rp](8-Br-Rp-
cGMPS-1-(EO)₅-E-1-Rp-cGMPS-8-Br)
Using general procedure Z2, Rp-8-Br-cGMPS is reacted with B-(EO)₅-(CH₂)₂-Br to
give the title compound.

16

8-Bromoguanosine-3',5'-cyclic monophosphorothioate[Rp]-[1-
propylamidomethyl-(pentaethoxy)-propylamidopropyl-1]-8-bromoguanosine-
3',5'-cyclic monophosphorothioate[Rp](8-Br-Rp-cGMPA-1-PrAmdM-(EO)₅-
PrAmdPr-1-Rp-cGMPS-8-Br) and
Using equivalent-adapted general procedure L, Rp-8-Br-1-CPr-cGMPS is reacted with TABLE 15-continued Examples of novel equatorially modified polymer linked multimeric cGMP
compounds according to the invention.

Entry Compound/Structure

NH$_2$CH$_2$-(EO)$_5$-(CH$_2$)$_3$—NH$_2$ (3 eq) to give the title compound and the corresponding
PEGylated monomeric analogue. Decreasing equivalents of PEG reagent favors
formation of the title product.

17

8-Bromoguanosine-3',5'-cyclic monophosphorothioate[Rp]-[1-
propylamidomethyl-(pentaethoxy)-propylamidomethylthio-8]-guanosine-3',5'-
cyclic monophosphorothioate[Rp](8-Br-Rp-cGMPA-1-PrAmdM-(EO)$_5$-
PrAmdMT-8-Rp-cGMPS)
Using general procedure J, Rp-1-Am-(EO)$_5$-PrAmdPr-8-Br-cGMPS is reacted with Rp-
8-CMT-cGMPS to give the title compound.

TABLE 15-continued

Examples of novel equatorially modified polymer linked multimeric cGMP
compounds according to the invention.

| Entry | Compound/Structure |
|---|---|
| 18 | |
| | 8-Bromoguanosine-3′,5′-cyclic monophosphorothioate[Rp]-[1-propylamidomethyl-(pentaethoxy)-propylamidomethylthio-8]-β-phenyl-1,N²-ethenoguanosine-3′,5′-cyclic monophosphorothioate[Rp](8-Br-Rp-cGMPS-1-PrAmdM-(EO)₅-PrAmdMT-8-Rp-cGMPS-PET)<br><br>Using general procedure J, Rp-1-Am-(EO)₅-PrAmdPr-8-Br-cGMPS is reacted with Rp-8-CMT-PET-cGMPS to give the title compound. |
| 19 | |
| | Guanosine-3′,5′-cyclic monophosphorothioate[Rp]-[8-(phenyl-4-thio)-(pentaethoxy)-ethyl-(4-thiophenyl)-8]-guanosine-3′,5′-cyclic monophosphorothioate[Rp][(Rp-cGMPS-8-PpT-(EO)₅-EpTP-8-Rp-cGMPS) monophosphorothioate W, Rp-8-Br-cGMPS is reacted with 4-B(OH)₂PhS-(EO)₅-(CH₂)₂-4-SPhB(OH)₂ (0.5 eq) to give the title compound. |

TABLE 15-continued

Examples of novel equatorially modified polymer linked multimeric cGMP compounds according to the invention.

Entry   Compound/Structure

20

(with $CH_2CH_2O)_n$ referring to PEG polydispers 2000 Da)
β-(3-Thiophenyl)-1,$N^2$-etheno)guanosine-3',5'-cyclic monophosphorothioate[Rp]-[8-thiomethylamido-(PEG pd 2000)-amidomethylthio-8]-β-(3-thiophenyl)-1,$N^2$-ethenoguanosine-3',5'-cyclic monophosphorothioate[Rp]((3-Tp)ET-Rp-cGMPS-8-TMAmd-(PEG pd 2000)-AmdMT-8-Rp-cGMPS-(3-Tp)ET)
Using general procedure C, Rp-8-Br-(3-Tp)ET-cGMPS is reacted with mercaptoacetic acid to give the 8-carboxymethylthio-substituted analogue, which is transferred into the title compound applying general procedure L in the presence of $NH_2$-$PEG_n$-$(CH_2)_2$-$NH_2$ (2000 Da, polydispers).

|

Monomeric precursors of the invention and/or momomeric compounds of the invention are further illustrated by the figures and examples of Table 16 describing preferred embodiments of the present invention which are, however, not intended to limit the invention in any way. Structural examples of novel compounds are depicted in the free acid form. After TIPLC workup, compounds are obtained as salts of the applied buffer, but can be transformed to other salt forms or to the free acid by cation exchange according to standard procedures for nucleotides.

TABLE 16

Examples of monomeric precursors and/or monomeric compounds of the invention.

| Entry | Compound/Structure |
|---|---|
| 21 | |

$\beta$-1,$N^2$-Acetyl-8-bromoguanosine-3',5'-cyclic monophosphorothioate, Rp-isomer (Rp-$\beta$-1,$N^2$-Ac-8-Br-cGMPS)
Using general procedure Y2, Rp-8-Br-cGMPS was reacted with methyl bromoacetate to give the title compound.
Yield (Purity): 48% (>99%).
HPLC: (4% i-PrOH, 20 mM TEAF buffer, pH 6.7).
UV-VIS: $\lambda_{max}$ = 266 nm (pH 7), $\epsilon$ = 17400 (est.).
ESI-MS (+): m/z calculated for $C_{12}H_{12}BrN_5O_7PS$ ([M + H]$^+$): 479.94, found: 480.
ESI-MS (−): m/z calculated for $C_{12}H_{10}BrN_5O_7PS$ ([M − H]$^-$): 477.92, found: 478.

| 22 | |

8-Bromo-(4-methyl-3-phenyl-1,$N^2$-etheno)guanosine-3',5'-cyclic monophosphorothioate, Rp- isomer (Rp-8-Br-pMe-PET-cGMPS)
Using general procedure Y, Rp-8-Br-cGMPS was reacted with 2-bromo-4'-methylacetophenone to give the title compound.
Yield (Purity): 47% (>99%).
HPLC: (24% MeCN, 50 mM NaH$_2$PO$_4$ buffer, pH 6.8).
UV-VIS: $\lambda_{max}$ = 261 nm (pH 7), $\epsilon$ = 40000 (est.).
ESI-MS (+): m/z calculated for $C_{19}H_{18}BrN_5O_6PS$ ([M + H]$^+$): 553.99, found: 554.
ESI-MS (−): m/z calculated for $C_{19}H_{16}BrN_5O_6PS$ ([M − H]$^-$): 551.97, found: 552.

| 23 | |

TABLE 16-continued

| Examples of monomeric precursors and/or monomeric compounds of the invention. | |
| --- | --- |
| Entry | Compound/Structure |

8-Bromo-(3-thiophen-yl-1,$N^2$-etheno)guanosine-3',5'-cyclic
monophosphorothioate, Rp- isomer (Rp-8-Br-(3-Tp)ET-cGMPS)
Using general procedure Y, Rp-8-Br-cGMPS was reacted with 3-(bromoacetyl)-
thiophene to give the title compound.
Yield (Purity): 61% (>99%).
HPLC: (24% MeCN, 50 mM NaH$_2$PO$_4$ buffer, pH 6.8).
UV-VIS: λmax = 261 nm (pH 7), ε = 40000 (est.).
ESI-MS (+): m/z calculated for C$_{16}$H$_{14}$BrN$_5$O$_6$PS$_2$ ([M + H]$^+$): 545.93, found: 546.
ESI-MS (–): m/z calculated for C$_{16}$H$_{12}$BrN$_5$O$_6$PS$_2$ ([M – H]$^-$): 543.92, found: 544.

24

8-Bromo-(2-naphthyl-1,$N^2$-etheno)guanosine-3',5'-cyclic
monophosphorothioate, Rp- isomer (Rp-8-Br-(2-N)ET-cGMPS)
Using general procedure Y, Rp-8-Br-cGMPS was reacted with 2-bromo-2'-
acetonapthone to give the title compound.
Yield (Purity): 12% (>98%).
HPLC: (33% MeCN, 50 mM NaH$_2$PO$_4$ buffer, pH 6.8).
UV-VIS: λmax = 256 nm (pH 7), ε = 40000 (est.).
ESI-MS (+): m/z calculated for C$_{22}$H$_{18}$BrN$_5$O$_6$PS ([M + H]$^+$): 589.99, found: 590.
ESI-MS (–): m/z calculated for C$_{22}$H$_{16}$BrN$_5$O$_6$PS ([M – H]$^-$): 587.97, found: 588.

25

8-Bromo-(α-methyl-β-phenyl-1,$N^2$-etheno)guanosine-3',5'-cyclic
monophosphorothioate, Rp- isomer (Rp-8-Br-aMpP-ET-cGMPS)
Using general procedure Y, Rp-8-Br-cGMPS was reacted with 2-bromo-propiophenone
to give the title compound.
Yield (Purity): 24% (>98%).
HPLC: (24% MeCN, 50 mM NaH$_2$PO$_4$ buffer, pH 6.8).
UV-VIS: λmax = 252 nm (pH 7), ε = 40000 (est.).
ESI-MS (+): m/z calculated for C$_{19}$H$_{18}$BrN$_5$O$_6$PS ([M + H]$^+$): 553.99, found: 554.
ESI-MS (–): m/z calculated for C$_{19}$H$_{16}$BrN$_5$O$_6$PS ([M – H]$^-$) 551.97 found: 552.

TABLE 16-continued

Examples of monomeric precursors and/or monomeric compounds of the invention.

| Entry | Compound/Structure |
| --- | --- |

26

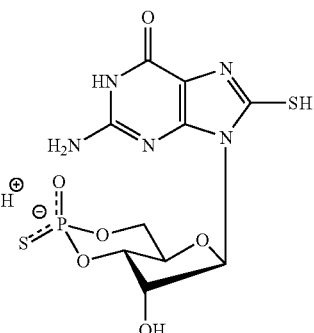

1-Benzyl-8-bromoguanosine-3',5'-cyclic monophosphorothioate, Rp- isomer (Rp-1-Bn-8-Br-cGMPS)

Using general procedure Z, Rp-8-Br-cGMPS was reacted with benzyl bromide to give the title compound.

Yield (Purity): 33% (>99%).

HPLC: (20% MeCN, 50 mM $NaH_2PO_4$ buffer, pH 6.8).

UV-VIS: $\lambda$max = 265 nm (pH 7), $\epsilon$ = 16500 (est.).

ESI-MS (+): m/z calculated for $C_{17}H_{18}BrN_5O_6PS$ ([M + H]$^+$): 529.99, found: 530.

ESI-MS (−): m/z calculated for $C_{17}H_{16}BrN_5O_6PS$ ([M − H]$^−$) 527.97 found: 528.

27

8-Thioguanosine-3',5'-cyclic monophosphorothioate, Rp- isomer (Rp-8-T- cGMPS)

Using modified general procedure C, Rp-8-Br-cGMPS was reacted with NaSH (50 eq)

in borate buffer (pH 9) at 75° C. (without addition of a further base) to give the title compound.

Yield (Purity): 52% (>99%).

HPLC: (3% i-PrOH, 20 mM TEAF buffer, pH 6.8).

UV-VIS: $\lambda$max = 286 nm (pH 7), $\epsilon$ = 17300 (est.).

ESI-MS (+): m/z calculated for $C_{16}H_{28}N_6O_6PS_2$ ([M + $Et_3$NH]$^+$): 495.12, found: 495.

ESI-MS (−): m/z calculated for $C_{10}H_{11}N_5O_6PS_2$ ([M − H]$^−$): 391.99, found: 392.

TABLE 16-continued

Examples of monomeric precursors and/or monomeric compounds of the invention.

| Entry | Compound/Structure |
| --- | --- |

28

8-(4-Isopropylphenylthio)guanosine-3',5'-cyclic monophosphorothioate, Rp-
isomer (Rp-8-pIPrPT-cGMPS)
Using general procedure A, Rp-8-Br-cGMPS was reacted with 4-isopropylthiophenol to
give the title compound.
Yield (Purity): 32% (>99%).
HPLC: (26% MeCN, 20 mM NaH$_2$PO$_4$ buffer, pH 6.8).
UV-VIS: λmax = 278 nm (pH 7), ε = 21500 (est.).
ESI-MS (+): m/z calculated for C$_{19}$H$_{23}$N$_5$O$_6$PS$_2$ ([M+H]$^+$): 512.08, found: 512.
ESI-MS (−): m/z calculated for C$_{19}$H$_{21}$N$_5$O$_6$PS$_2$ ([M − H]$^-$): 510.07, found: 510.

29

8-Carboxymethylthioguanosine-3',5'-cyclic monophosphorothioate, Rp- isomer
(Rp-8-CMT-cGMPS)
Using general procedure C, Rp-8-Br-cGMPS was reacted with mercaptoacetic acid to
give the title compound.
Yield (Purity): 74% (>99%).
HPLC: (4% MeCN, 30 mM NaH$_2$PO$_4$ buffer, pH 6.8).
UV-VIS: λmax = 275 nm (pH 7), ε = 13700 (est.).
ESI-MS (+): m/z calculated for C$_{12}$H$_{16}$N$_5$O$_8$PS$_2$ ([M + H]$^+$): 453.02, found: 453.
ESI-MS (−): m/z calculated for C$_{12}$H$_{14}$N$_5$O$_8$PS$_2$ ([M − H]$^-$): 451.00, found: 451.

30

8-(2-Aminophenylthio)guanosine-3',5'-cyclic monophosphorothioate, Rp- isomer
(Rp-8-oAPT-cGMPS)
Using general procedure A2, Rp-8-Br-cGMPS was reacted with 2-aminothiophenol to
give the title compound.
Yield (Purity): 47% (>99%).

TABLE 16-continued

Examples of monomeric precursors and/or monomeric compounds of the invention.

| Entry | Compound/Structure |
| --- | --- |

HPLC: (40% MeOH, 20 mM TEAF buffer, pH 6.8).
UV-VIS: λmax = 278 nm (pH 7), ε = 18000 (est.).
ESI-MS (+): m/z calculated for $C_{16}H_{18}N_6O_6PS_2$ ([M + H]$^+$): 485.05, found: 485.
ESI-MS (−): m/z calculated for $C_{16}H_{16}N_6O_6PS_2$ ([M − H]$^-$) 483.03, found: 483.

31

8-Phenylamidomethylthioguanosine-3',5'-cyclic monophosphorothioate, Rp-
isomer (Rp-8-PAmdMT-cGMPS)
Using general procedure J, Rp-8-CMT-cGMPS was reacted with aniline to give the title
compound.
Yield (Purity): 66% (>99%).
HPLC: (38% MeOH, 50 mM TEAF buffer, pH 6.8).
UV-VIS: λmax = 273 nm (pH 7), ε = 13700 (est.).
ESI-MS (+): m/z calculated for $C_{18}H_{20}N_6O_7PS_2$ ([M + H]$^+$): 527.06, found: 527.
ESI-MS (−): m/z calculated for $C_{18}H_{18}N_6O_7PS_2$ ([M − H]$^-$) 525.04, found: 525.

32

8-Carboxymethylthio-β-phenyl-1,N$^2$-ethenoguanosine-3',5'-cyclic
monophosphorothioate, Rp- isomer (Rp-8-CMT-PET-cGMPS)
Using general procedure C, Rp-8-Br-PET-cGMPS was reacted with mercaptoacetic acid
to give the title compound.
Yield (Purity): 75% (>99%).
HPLC: (17% MeCN, 30 mM NaH$_2$PO$_4$ buffer, pH 6.8; for preparative HPLC polar
byproducts are first separated using 10% MeCN, 30 mM NaH$_2$PO$_4$ buffer, pH 6.8,
before switching to the described eluent).
UV-VIS: λmax = 273 nm (pH 7), ε = 40000 (est.).
ESI-MS (+): m/z calculated for $C_{20}H_{19}N_5O_8PS_2$ ([M + H]$^+$): 552.04, found: 552.
ESI-MS (−): m/z calculated for $C_{20}H_{17}N_5O_8PS_2$ ([M − H]$^-$): 550.03, found: 550.

33

TABLE 16-continued

| Examples of monomeric precursors and/or monomeric compounds of the invention. | |
| --- | --- |
| Entry | Compound/Structure |

β-Phenyl-1,N$^2$-etheno-8-phenylamidomethylthioguanosine-3',5'-cyclic
monophosphorothioate, Rp- isomer (Rp-PET-8-PAmdMT-cGMPS)
Using general procedure J, Rp-8-CMT-PET-cGMPS was reacted with aniline to give the
title compound.
Yield (Purity): 43% (>99%).
HPLC: (35% MeCN, 50 mM NaH$_2$PO$_4$ buffer, pH 6.8).
UV-VIS: λmax = 274 nm (pH 7), ε = 40000 (est.).
ESI-MS (+): m/z calculated for C$_{26}$H$_{24}$N$_6$O$_7$PS$_2$ ([M + H]$^+$): 627.09, found: 627.
ESI-MS (−): m/z calculated for C$_{26}$H$_{22}$N$_6$O$_7$PS$_2$ ([M − H]$^-$) 625.07, found: 625.

34

8-(4-Hydroxyphenylthio)-β-phenyl-1,N$^2$-ethenoguanosine-3',5'-cyclic
monophosphorothioate, Rp- isomer (Rp-8-pHPT-PET-cGMPS)
Using general procedure A, Rp-8-Br-PET-cGMPS was reacted with 4-mercaptophenol
(6 eq) in the presence of NaOH (2 M, 2.5 eq) to give the title compound.
Yield (Purity): 54% (>99%).
HPLC: (26% MeCN, 10 mM NaH$_2$PO$_4$ buffer, pH 6.8; for preparative HPLC polar
byproducts are first separated using 22% MeCN, 10 mM NaH$_2$PO$_4$ buffer, pH 6.8,
before switching to the described eluent).
UV-VIS: λmax = 274 nm (pH 7), ε = 40000 (est.).
ESI-MS (+): m/z calculated for C$_{24}$H$_{21}$N$_5$O$_7$PS$_2$ ([M + H]$^+$): 586.06, found: 586.
ESI-MS (−): m/z calculated for C$_{24}$H$_{19}$N$_5$O$_7$PS$_2$ ([M − H]$^-$) 584.05, found: 584.

35

8-(4-Isopropylphenylthio)-β-phenyl-1,N$^2$-ethenoguanosine-3',5'-cyclic
monophosphorothioate, Rp- isomer (Rp-8-pIPrPT-PET-cGMPS)
Using modified general procedure A, Rp-8-Br-PET-cGMPS was reacted with 4-
isopropylthiophenol (4 eq) in the presence of NaOH (2 M, 1 eq) and N,N-
diisopropylethylamine (2 eq) in H2O/MeOH (1:3) at 60° C. to give the title compound.
Yield (Purity): 32% (>99%).
HPLC: (35% MeCN, 50 mM NaH$_2$PO$_4$ buffer, pH 7).
UV-VIS: λmax = 274 nm (pH 7), ε = 40000 (est.).
ESI-MS (+): m/z calculated for C$_{27}$H$_{27}$N$_5$O$_6$PS$_2$ ([M + H]$^+$): 612.11, found: 612.
ESI-MS (−): m/z calculated for C$_{27}$H$_{25}$N$_5$O$_6$PS$_2$ ([M − H]$^-$): 610.10, found: 610.

TABLE 16-continued

Examples of monomeric precursors and/or monomeric compounds of the invention.

| Entry | Compound/Structure |
| --- | --- |
| 36 | |

8-(2-Aminophenylthio)-β-phenyl-1,$N^2$-ethenoguanosine-3',5'-cyclic
monophosphorothioate, Rp- isomer (Rp-8-oAPT-PET-cGMPS)
Using general procedure A2, Rp-8-Br-PET-cGMPS was reacted with 2-aminothiophenol
(7.7 eq) to give the title compound.
Yield (Purity): 31% (>99%).
HPLC: (30% MeCN, 20 mM TEAF buffer, pH 6.8).
UV-VIS: λmax = 272 nm (pH 7), ε = 40000 (est.).
ESI-MS (+): m/z calculated for $C_{24}H_{22}N_6O_6PS_2$ ([M + H]$^+$): 585.08, found: 585.
ESI-MS (−): m/z calculated for $C_{24}H_{20}N_6O_6PS_2$ ([M − H]$^-$): 583.06, found: 583.

37

β-Phenyl-1,$N^2$-etheno-8-thioguanosine-3',5'-cyclic monophosphorothioate, Rp-
isomer (Rp-PET-8-T-cGMPS)
Using modified general procedure C, Rp-8-Br-cGMPS was dissolved in water (to a 5 M
solution) containing NaOH (10%, 2 eq), diluted with NaHCO₃-buffer (pH 9.3) by a
factor of 10 and reacted with NaSH (58 eq) at 95° C. to give the title compound.
Yield (Purity): 65% (>95%).
HPLC: (28% ACN, 50 mM NaH₂PO₄ buffer, pH 6.8).
UV-VIS: λmax = 288 nm (pH 7), ε = 40000 (est.).
ESI-MS (+): m/z calculated for $C_{18}H_{17}N_5O_6PS_2$ ([M + Et₃NH]$^+$): 494.04, found: 494.
ESI-MS (−): m/z calculated for $C_{18}H_{15}N_5O_6PS_2$ ([M − H]$^-$): 492.02, found: 492.

38

8-(4-Isopropylphenylthio)guanosine-3',5'-cyclic monophosphorothioate, Rp-
isomer (Rp-8-pIPrPT-cGMPS)
Using general procedure A, Rp-8-Br-cGMPS is reacted with sodium methanethiolate to
give the title compound.

TABLE 16-continued

Examples of monomeric precursors and/or monomeric compounds of the invention.

| Entry | Compound/Structure |
|---|---|
| 39 | |

β-(4-Azidophenyl)-1,N²-etheno-8-bromoguanosine-3',5'-cyclic
monophosphorothioate, Rp- isomer ( Rp-4-N₃-PET-8-Br-cGMPS )
Using general procedure Y, Rp-8-Br-cGMPS is reacted with 4-azidophenacylbromide to
give the title compound.

| 40 | |

8-(2-Aminoethyl)-(octaethoxy)-amidomethylthioguanosine-3',5'-cyclic
monophosphorothioate, Rp- isomer (Rp-8-AE-(EO)₈-AmdMT-cGMPS)
Using general procedure K, Rp-8-CMT-cGMPS (1 eq) is reacted with NH₂—(EO)₈—
(CH₂)₂NH₂ (6 eq) to give the title compound.

| 41 | |

8-(3-Aminopropyl)-(pentaethoxy)-methylamidomethylthio-guanosine-3',5'-
cyclic monophosphorothioate, Rp- isomer (Rp-8-APr-(EO)₈-MAmdMT-cGMPS)
Using general procedure K, Rp-8-CMT-cGMPS (1 eq) is reacted with NH₂CH₂—(EO)₅—
(CH₂)₃NH₂ (6 eq) to give the title compound.

TABLE 16-continued

Examples of monomeric precursors and/or monomeric compounds of the invention.

| Entry | Compound/Structure |
| --- | --- |

42

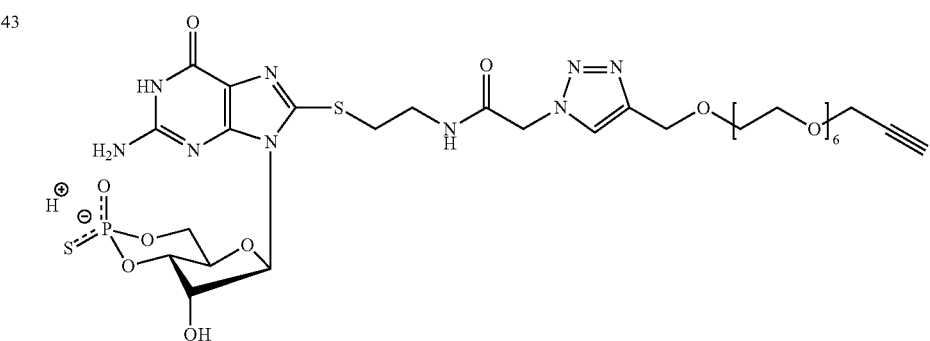

8-Azidomethylamidoethylthioguanosine-3',5'-cyclic monophosphorothioate, Rp-
isomer (Rp-8-N$_3$-MAmdET-cGMPS)
Using general procedure J, Rp-8-AET-cGMPS is reacted with azidoacetic acid to give
the title compound.

43

8-(4-(Propargyloxy-(hexaethoxy)-methyl)-[1,2,3]-triazole-1-yl)-
methylamidoethylthioguanosine-3',5'-cyclic monophosphorothioate, Rp- isomer
(8-(Rp-4-(PargO-(EO)$_6$-Me)-[1,2,3]-Tz-1)-MAmdET-cGMPS) and
Using general procedure S, Rp-8-N$_3$-MAmdET-cGMPS (1 eq) is reacted with bis-
propargyl-(EO)$_7$ (2 eq) to give the title compound and the corresponding dimeric
analogue. Increasing equivalents of PEG reagent favors formation of the PEGylated
monomeric product.

44

8-Bromo-1-(3-carboxypropyl)guanosine-3',5'-cyclic monophosphorothioate, Rp-
isomer (Rp-8-Br-1-CPr-cGMPS)
Using general procedure Z, Rp-8-Br-cGMPS is reacted with ethyl 4-bromobutyrate to
give the corresponding ethylester of the title compound. The crude product is
transformed into the titel compound without prior chromatographic workup using
general procedure F.

TABLE 16-continued

| Examples of monomeric precursors and/or monomeric compounds of the invention. | |
| --- | --- |
| Entry | Compound/Structure |

45

8-Bromo-δ-1,N²-butyrylguanosine-3',5'-cyclic monophosphorothioate, Rp-
isomer (Rp-8-Br-6-1,N²-But-cGMPS)
Using general procedure Y3, Rp-8-Br-1-CPr-cGMPS is transformed into the title
compound.

46

1-[Aminomethyl-(pentaethoxy)-propylamidopropyl]-8-bromoguanosine-3',5'-
cyclic monophosphorothioate, Rp- isomer (Rp-1-AM-(EO)₅-PrAmdPr-8-Br-
cGMPS)
Using equivalent-adapted general procedure L, Rp-8-Br-1-CPr-cGMPS is reacted with
NH₂CH₂—(EO)₅—(CH₂)₃—NH₂ (3 eq) to give the title compound and the corresponding
dimeric analogue. Increasing equivalents of PEG reagent favors formation of the
PEGylated monomeric product.

47

8-Phenylguanosine-3',5'-cyclic monophosphorothioate, Rp- isomer (Rp-8-Phe-
cGMPS)
Using general procedure W, Rp-8-Br-cGMPS is reacted with phenylboronic acid to give
the title compound.

TABLE 16-continued

Examples of monomeric precursors and/or monomeric compounds of the invention.

| Entry | Compound/Structure |
| --- | --- |
| 48 | |

8-(2-Furyl)guanosine-3',5'-cyclic monophosphorothioate, Rp- isomer (Rp-8-(2-
Fur)-cGMPS)
Using general procedure W, Rp-8-Br-cGMPS isr eacted with 2-furylboronic acid to give
the title compound.

49

8-(4-Chlorophenyl)guanosine-3',5'-cyclic monophosphorothioate, Rp- isomer
(Rp-8-pCP-cGMPS)
Using general procedure W, Rp-8-Br-cGMPS is reacted with 4-chlorophenylboronic
acid to give the title compound.

50

8-Phenyl-$\beta$-phenyl-1,$N^2$-ethenoguanosine-3',5'-cyclic monophosphorothioate,
Rp- isomer (Rp-8-Phe-PET-cGMPS)
Using general procedure W, Rp-8-Br-PET-cGMPS is reacted with phenylboronic acid to
give the title compound.

TABLE 16-continued

Examples of monomeric precursors and/or monomeric compounds of the invention.

| Entry | Compound/Structure |
|---|---|

51

8-(4-Chlorophenyl)-β-phenyl-1,$N^2$-ethenoguanosine-3',5'-cyclic
monophosphorothioate, Rp- isomer (Rp-8-pCP-PET-cGMPS)
Using general procedure W, Rp-8-Br-PET-cGMPS is reacted with 4-
chlorophenylboronic acid to give the title compound.

52

8-(4-Chlorophenylsulfoxide)guanosine-3',5'-cyclic monophosphorothioate, Rp-
isomer (Rp-8-pCPS(O)-cGMPS)
Applying general procedure P, 8-(4-Chlorophenylthio)guanosine (commercially
available from Biolog Life Science Institute (Bremen, Germany)) is oxidized to the
corresponding sulfoxide analogue using OXONE ®, followed by thiophosphorylation to
give the title compound.

53

8-(4-Chlorophenylsulfonyl)guanosine-3',5'-cyclic monophosphorothioate, Rp-
isomer (Rp-8-pCPS(O)$_2$-cGMPS)
Applying general procedure O, 8-(4-Chlorophenylthio)guanosine (commercially
available from Biolog Life Science Institute (Bremen, Germany)) is oxidized to the
corresponding sulfonyl analogue using OXONE ®, followed by thiophosphorylation to
give the title compound.

TABLE 16-continued

Examples of monomeric precursors and/or monomeric compounds of the invention.

| Entry | Compound/Structure |
| --- | --- |
| 54 | |

8-(4-Chlorophenylsulfonyl)-β-phenyl-1,$N^2$-ethenoguanosine-3',5'-cyclic
monophosphorothioate, Rp- isomer (Rp-8-pCPS(O)$_2$-PET-cGMPS)
Applying general procedure O, 8-(4-Chlorophenylthio)-β-phenyl-1,$N^2$-
ethenoguanosine (commercially available from Biolog Life Science Institute (Bremen,
Germany)) is oxidized to the corresponding sulfonyl analogue using OXONE ®, followed
by thiophosphorylation to give the title compound.

2. Determination of Lipophilicity

Although a generally accepted indicator for the expected capability of a given analogue to pass through the cellular lipid bilayer by passive diffusion is the octanol/water partition coefficient Log P, the determination of such data is rather difficult for polar structures such as cyclic nucleotides. Lipophilicity information is thus often only obtained by fragment analysis and corresponding calculations.

An established TIPLC method, which is based on retention data on RP-18 reversed phase silica during gradient elution, was used for the determination of lipohilicity.

Instead of log P the method yields the descriptor log $k'_g$, ranking analytes according to their lipophilicity on a logarithmic scale as well. Since charged molecules such as cyclic nucleotides have only hardly any retention on reversed phases, ion pair chromatography with the lipophilic triethylammonium cation is used.

Unmodified cGMP itself (log $k'_g$ 0.77) is considered not to be membrane-permeant by passive diffusion, which means that only analogues with considerable hydrophobic modifications and substituents, respectively, which counteract against the negative charge at the phosphate moiety, can be used for extracellular application.

A prior analysis of widely used cyclic nucleotide analogues in our laboratory has shown that noteworthy diffusion into cells takes place only for analogues having a log $k'_g$ of at least 1.2 and this fits well to a study of Werner et al. (2011).[14]

The results of a corresponding analysis of 12 novel, equatorially modified cGMP analogues with Rp phosphorothioate is shown in Table 17. For comparison and control, 3 established structures (compound A-C) were re-analysed within this series.

TABLE 17 log $k'_g$ values of exemplary compounds of the invention (compound numbers refer to structures depicted in Table 13 and 14.

| Compound | Analogue | log k'g |
| --- | --- | --- |
| A | Rp-cGMPS | 0.894 |
| B | Rp-8-Br-cGMPS | 1.285 |
| C | Rp-8-Br-PET-cGMPS | 2.831 |
| 21 | Rp-β-1,$N^2$-Ac-8-Br-cGMPS | 1.368 |
| 30 | Rp-8-oAPT-cGMPS | 1.974 |
| 31 | Rp-8-PAmdMT-cGMPS | 2.105 |
| 23 | Rp-8-Br-(3-Tp)ET-cGMPS | 2.746 |
| 34 | Rp-8-pHPT-PET-cGMPS | 3.078 |
| 22 | Rp-8-Br-pMe-PET-cGMPS | 3.134 |
| 36 | Rp-8-oAPT-PET-cGMPS | 3.150 |
| 33 | Rp-PET-8-PAmdMT-cGMPS | 3.411 |
| 24 | Rp-8-Br-(2-N)ET-cGMPS | 3.426 |
| 35 | Rp-8-pIPrPT-PET-cGMPS | 3.815 |
| 1 | Rp-cGMPS-8-TMAmd-(EO)$_8$-EAmdMT-8-Rp-cGMPS | 2.039* |
| 2 | PET-Rp-cGMPS-8-TMAmd-(EO)$_8$-EAmdMT-8-Rp-cGMPS-PET | 3.236* |

*values for dimeric analogues are not directly comparable with values for monomeric analogues.

All monomeric analogues had log $k'_g$ values >1.2 and thus have sufficient lipophilicity to cross cellular membranes.

Most of the monomeric analogues have similar or even increased lipophilicity compared to Rp-8-Br-PET-cGMPS. All monomeric analogues with log $k'_g$ values >2.831 are expected to have improved membrane permeation in biological systems and thus improved properties compared to Rp-8-Br-PET-cGMPS.

Table 17 shows lipophilicity data for two cGMPS dimers (compounds 1 and 2) as well. However, since these structures have two negative charges at physiological pH, the corresponding values are not directly comparable with log $k'_g$ values obtained for the monomeric analogues with only a single negative charge.

3. Primary Rod-Like Cells: Assessment of Cell Death Using the Ethidium Homodimer Assay

Background

Primary photoreceptors derived from retinal stem cells after differentiation in vitro have been demonstrated to be an appropriate in vitro system to study mechanisms of cell death related to retinal degeneration and to cGMP unbalance as well as to screen compounds with neuroprotective activities.[5-6] Data obtained by screening of drugs in this in vitro system can then be used for further research studies on retinal explants and in vivo in the eye of animal models of the disease.

Experimental Part

Primary rod-like cells were obtained by isolating stem cells from the ciliary epithelium of murine eyes.[15] The cells are cultured until they form neurospheres in DMEM/F12 with FGF (20 ng/ml), Heparin (2 µg/ml), N2 (lx), Glucose (0,6%), HEPES (5 µM) and 1% Penicillin/Streptomycin. Single neurospheres are picked and plated onto glass slides coated with ECM in the same medium as before with the exception of reduced FGF concentration (10 ng/ml) to induce adhesion. Four days later, the medium is changed to DMEM/F12 with N2, Glucose, HEPES and Penicillin/Streptomycin supplemented with 1% FBS to allow differentiation into rod-like photoreceptors. Treatment with compounds begins at day 10 after neurosphere plating. This timepoint was chosen because cells derived from rd1 mutant eyes show a peak of cell death and activate cell death pathways like in the retina in vivo.[5b] Compounds were dissolved in water and then diluted in the differentiation medium at concentrations of 1 nM to 100 µM. 24 hours after treatment cells were washed with PBS and fixed in 4% PFA. Afterwards slides were dipped into 2 µM Ethidium Homodimer for 2 minutes and nuclei were stained with DAPI. Ethidium Homodimer stains nuclei of dying cells. To assess cell death, microphotographs were taken from three different slides for each compound concentration and the total number of cells, as well as the number of dying Ethidium Homodimer positive cells, were counted in each picture. To statistically assess significant differences between untreated and treated cells, the unpaired Student's t-test was used and a p value ≤0.05 was considered significant (*≤0.05, ≤0.01, *≤0.001).

Results

FIG. 2 shows the protective effects of exemplary compounds of the invention. All tested compounds of the invention led to significantly improved survival rates of primary rod-like cells compared to not treated cells (black bars) and compared to the reference compounds Rp-8-Br-cGMPS and Rp-8-Br-PET-cGMPS (dashed bars) at both tested compound concentrations of 0.1 µM (FIG. 2*a*) and 1 µM (FIG. 2*b*). The most potent precedents of the exemplary compounds of the invention display 4.7- to 9-fold better reduction of cell death compared to the known compounds.

4. Retinal Explants: Determination of Photoreceptor Cell Death

Background

In addition to using cellular systems of degenerating retinal photoreceptors or photore-ceptor-like cells for assessing the properties of various cyclic nucleotide analogues, it is possible to use a serum-free, organotypic explant culturing system, in which retinas from young animals are explanted and kept in culture for up to 3 weeks.[4, 9] The explant system will allow evaluation of the photoreceptor survival in an in vivo-like histological context, with much of the cytoarchitecture kept intact, but without the risk of for instance degradation or dilution, via body fluids etc., of any treatment compounds, which otherwise is a risk in vivo. The rd1 mouse is a very well studied model for RD and due to its degeneration characteristics, which include an early onset and a rapid progress of the photoreceptor cell death. The rd1 degeneration can readily be made to take place under the time frame of the explant culturing. This gives the benefit of easy pharmacological interventions to look for neuroprotective possibilities, which has been repeatedly taken advantage of.[4, 8] The studies have among other things allowed an outlining of some of the disease steps.

Experimental Part

The effects of different compounds of formula (I), (II) and monomeric precursors thereof formula (III) on the degeneration of retinal photoreceptors from model mice suffering from inherited retinal degeneration was investigated by means of a retinal explant system as described above. In this, retinas are dissected out from young animals, usually on postnatal day 5 (PN5) and cultured in serum free medium for several days (see also FIG. 3 for the rdl culturing paradigm), with medium change usually every second day.

In order to observe the effects of the different analogues on the degeneration, the retinas are at the end of experiment fixated (preserved). After this they are prepared for histological and other analyses, notably so called TUNEL staining to allow a quantification of photoreceptor cell death.

Results

FIG. 4 shows the outcome of a series of tests with the analogues of the invention, and in which the effects on the photoreceptor cell death is expressed as a ratio of treated to untreated (see figure legend). The left-most bar represents the untreated rd1 explants, while the other bars show selected analogues of the invention, used at concentrations that are either 50 µM, 10 µM or 1 µM. The effects of these analogues are compared with an analogue previously available, Rp-8-Br-PET-cGMPS, in a concentration matched way. Note that at all concentrations of Rp-8-Br-cGMPS and Rp-8-Br-PET-cGMPS, there are one or more analogues of the invention that are performing better.

| List of Acronyms | | | |
|---|---|---|---|
| cAMP | adenosine-3',5'-cyclic monophosphate | HEPES | 4-(2-hydroxyethyl)-1-piperazineethanesulfonic acid |
| cGMP | guanosine-3',5'-cyclic monophosphate | HOBt | 1-hydroxybenzotriazole |
| | | HPLC | high performance liquid |

-continued

List of Acronyms

| | | | |
|---|---|---|---|
| cGMPS | guanosine-3',5'-cyclic monophosphorothioate | | chromatography |
| | | $(i-Pr)_2EtNH^+$ | diisopropylethylammonium |
| CNGC | cyclic nucleotide gated ion channel | i-PrOH | 2-propanol |
| Cy | cyclohexyl | m/z | mass-to-charge ratio |
| Cyp | cyclopentyl | MeCN | acetonitrile |
| Da | Dalton | MTBE | tert-butyl methyl ether |
| DAPI | 4',6-diamidino-2-phenylindole | $M_w$ | molecular weight |
| DBU | 1,8-diazabicyclo[5.4.0]undec-7-ene | N2 | N2-supplement for cell |
| DMEM/F12 | Dulbecco's modifiziertes eagle | | culture |
| | medium in combination with | NHS | N-hydroxysuccinimid |
| | Ham's F-12 medium | PBS | phosphate buffered saline |
| DMF | N,N-dimethylformamide | $Pd(dppf)Cl_2$ | 1,1'- |
| DMSO | dimethyl sulfoxide | | bis(diphenylphosphino)- |
| dppf | 1,1'- | | ferrocene- |
| | Bis(diphenylphosphino)ferrocene | | palladium(II)dichloride |
| ECM | extracellular matrix | PDE | phosphodiesterase |
| EDC | 1-ethyl-3-(3- | PEG | polyethylene glycol |
| | dimethylaminopropyl)carbodiimide | PET | $\beta$-Phenyl-1, $N^2$-etheno |
| EGTA | ethylene glycol-bis(2- | PFA | paraformaldehyde |
| | ami noethyl ether)-N,N,N',N'- | PKG | cGMP-dependent protein |
| | tetraacetic acid | | kinase |
| ESI-MS | electrospray Ionization mass | PLD | polymer linked dimer |
| | spectrometry | PLM | polymer linked multimer |
| est. | estimated | PN | postnatal |
| $Et_3NH^+$ | triethylammonium | SD | standard deviation |
| FGF | fibroblast growth factor | TEA | triethylammonium |
| HCN | hyperpolarization-activated cyclic | TEAF | triethylammonium formate |
| | nucleotide-gated | UV-VIS | ultraviolet and visible |
| PyBOP | benzotriazole-1-yl- | | (spectroscopy) |
| | oxytripyrrolidinophosphonium | VS | vinylsulfone |
| | hexafluorophosphate | $\varepsilon$ | extinction coefficient |
| RD | retinal dystrophies | $\lambda_{max}$ | wavelength at which |
| rd 1 | retinal degeneration 1 | | absorbance is highest |
| rd 2 | retinal degeneration 2 | | |
| RP | retinitis pigmentosa | | |
| Rp | as in Rp-cGMPS refers to configuration of the chiral phosphorus, wherein R/S follows the Cahn-Ingold-Prelog rules while "p" stands for phosphorus. | | |
| RP-18 | reversed phase octadecyl modified material | | |

LITERATURE

1. Schlossmann, J.; Schinner, E., cGMP becomes a drug target. *Naunyn Schmiedebergs Arch Pharmacol* 2012, 385 (3), 243-52.
2. (a) Kawada, T.; Toyosato, A.; Islam, M. O.; Yoshida, Y.; Imai, S., cGMP-kinase mediates cGMP- and cAMP-induced Ca2+ desensitization of skinned rat artery. *Eur J Pharmacol* 1997, 323 (1), 75-82; (b) Genieser, H.-G.; Walter, U.; Butt, E. Derivatives of cyclic guanosine-3',5'-monophosphorothioate. U.S. Pat. No. 5,625,056 Apr. 29, 1997.
3. Butt, E.; Pohler, D.; Genieser, H. G.; Huggins, J. P.; Bucher, B., Inhibition of cyclic GMP-dependent protein kinase-mediated effects by (Rp)-8-bromo-PET-cyclic GMPS. *Br J Pharmacol* 1995, 116 (8), 3110-6.
4. Paquet-Durand, F.; Hauck, S. M.; van Veen, T.; Ueffing, M.; Ekstrom, P., PKG activity causes photoreceptor cell death in two retinitis pigmentosa models. *J Neurochem* 2009, 108 (3), 796-810.
5. (a) Mussolino, C.; Sanges, D.; Marrocco, E.; Bonetti, C.; Di Vicino, U.; Marigo, V.; Auricchio, A.; Meroni, G.; Surace, E. M., Zinc-finger-based transcriptional repression of rhodopsin in a model of dominant retinitis pigmentosa. *EMBO Mol Med* 2011, 3 (3), 118-128; (b) Sanges, D.; Comitato, A.; Tammaro, R.; Marigo, V., Apoptosis in retinal degeneration involves cross-talk between apoptosis-inducing factor (AIF) and caspase-12 and is blocked by calpain inhibitors. *Proc Natl Acad Sci USA* 2006, 103 (46), 17366-17371.
6. Comitato, A.; Sanges, D.; Rossi, A.; Humphries, M. M.; Marigo, V., Activation of Bax in Three Models of Retinitis Pigmentosa. *Invest Ophthalmol Vis Sci* 2014, 55 (6), 3555-3562.
7. Arango-Gonzalez, B.; Trifunovid, D.; Sahaboglu, A.; Kranz, K.; Michalakis, S.; Farinelli, P.; Koch, S.; Koch, F.; Cottet, S.; Janssen-Bienhold, U.; Dedek, K.; Biel, M.; Zrenner, E.; Euler, T.; Ekström, P.; Ueffing, M.; Paquet-Durand, F., Identification of a common non-apoptotic cell death mechanism in hereditary retinal degeneration. *PloS One* 2014, 9 (11), el 12142-el 12142.
8. Paquet-Durand, F.; Beck, S.; Michalakis, S.; Goldmann, T.; Huber, G.; Muhlfriedel, R.; Trifunovic, D.; Fischer, M. D.; Fahl, E.; Duetsch, G.; Becirovic, E.; Wolfrum, U.; van Veen, T.; Biel, M.; Tanimoto, N.; Seeliger, M. W., A key role for cyclic nucleotide gated (CNG) channels in cGMP-related retinitis pigmentosa. *Hum Mol Genet* 2011, 20 (5), 941-7.
9. Caffe, A. R.; Ahuja, P.; Holmqvist, B.; Azadi, S.; Forsell, J.; Holmqvist, I.; Soderpalm, A. K.; van Veen, T., Mouse retina explants after long-term culture in serum free medium. *J Chem Neuroanat* 2001, 22 (4), 263-73.
10. Kramer, R. H.; Karpen, J. W., Spanning Binding Sites on Allosteric Proteins with Polymer-linked Ligand Dimers. *Nature* 1998, 395, 710-713.

11. Kramer, R. H.; Karpen, J. W. Multimeric Tethered Ligands and Their Use in Receptor-Ligand Interaction. WO 99/25384 1999.

12. Strassmaier, T.; Karpen, J., Novel N7- and N1-substituted cGMP Derivatives Are Potent Activators of Cyclic Nucleotide-Gated Channels. *J. Med. Chem.* 2007, 50, 4186-4194.

13. (a) Bala, I.; Hariharan, S.; Kumar, M. N., PLGA nanoparticles in drug delivery: the state of the art. *Crit Rev Ther Drug Carrier Syst* 2004, 21 (5), 387-422; (b) Basu, S. C.; Basu, M., Liposome Methods and Protocols. Humana Press: 2002; (c) Gregoriadis, G., *Liposome Technology*. Informa Healthcare: 2006; (d) Paquet-Durand, F.; Gaillard, P. J.; Maringo, V.; Ekström, P.; Genieser, H.-G.; Rentsch, A. Targeted liposomal delivery of cGMP analogues. PCT/EP2016/055659.

14. Werner, K.; Schwede, F.; Genieser, H. G.; Geiger, J.; Butt, E., Quantification of cAMP and cGMP analogs in intact cells: pitfalls in enzyme immunoassays for cyclic nucleotides. *Naunyn Schmiedebergs Arch Pharmacol* 2011, 384 (2), 169-76.

15. Giordano, F.; De Marzo, A.; Vetrini, F.; Marigo, V., Fibroblast growth factor and epidermal growth factor differently affect differentiation of murine retinal stem cells in vitro. *Mol Vis* 2007, 13, 1842-50.

We claim:

1. A method of treating a neurodegenerative disorder in a human comprising administering an effective amount of a compound to the human in need thereof wherein the compound is selected from the group consisting of:
- (22) 8-Bromo-(4-methyl-β-phenyl-1, $N^2$-etheno)guanosine-3', 5'-cyclic monophosphorothioate, Rp-isomer;
- (23) 8-Bromo-(3-thiophen-yl-1, $N^2$-etheno)guanosine-3', 5'-cyclic monophosphorothioate, Rp-isomer;
- (24) 8-Bromo-(2-naphthyl-1, $N^2$-etheno)guanosine-3', 5'-cyclic monophosphorothioate, Rp-isomer;
- (32) 8-Carboxymethylthio-β-phenyl-1, $N^2$-ethenoguanosine-3', 5'-cyclic monophosphorothioate, Rp-isomer;
- (33) β-Phenyl-1, $N^2$-etheno-8-phenylamidomethylthioguanosine-3', 5'-cyclic monophosphorothioate, Rp-isomer;
- (34) 8-(4-Hydroxyphenylthio)-β-phenyl-1, $N^2$-ethenoguanosine-3', 5'-cyclic monophosphorothioate, Rp-isomer;
- (35) 8-(4-Isopropylphenylthio)-β-phenyl-1, $N^2$-ethenoguanosine-3', 5'-cyclic monophosphorothioate, Rp-isomer;
- (36) 8-(2-Aminophenylthio)-β-phenyl-1, $N^2$-ethenoguanosine-3', 5'-cyclic monophosphorothioate, Rp-isomer;
- (37) β-Phenyl-1, $N^2$-etheno-8-thioguanosine-3', 5'-cyclic monophosphorothioate, Rp-isomer;
- (39) β-(4-Azidophenyl)-1, $N^2$-etheno-8-bromoguanosine-3', 5'-cyclic monophosphorothioate, Rp-isomer;
- (50) 8-Phenyl-β-phenyl-1, $N^2$-ethenoguanosine-3', 5'-cyclic monophosphorothioate, Rp-isomer;
- (51) 8-(4-Chlorophenyl)-β-phenyl-1, $N^2$-ethenoguanosine-3', 5'-cyclic monophosphorothioate, Rp-isomer;
- (52) 8-(4-Chlorophenylsulfoxide) guanosine-3', 5'-cyclic monophosphorothioate, Rp-isomer; and
- (54) 8-(4-Chlorophenylsulfonyl)-β-phenyl-1, $N^2$-ethenoguanosine-3', 5'-cyclic monophosphorothioate, Rp-isomer;

or a pharmaceutically acceptable salt thereof.

2. The method of claim 1, wherein the neurodegenerative disorder is spinal cord injury.

3. The method of claim 2, wherein the compound is:
8-Bromo-(4-methyl-β-phenyl-1, $N^2$-etheno)guanosine-3', 5'-cyclic monophosphorothioate, Rp-isomer;
or a pharmaceutically acceptable salt thereof.

4. The method of claim 1, comprising administering 0.1μM to 50μM of the compound.

5. A method of treating a human with a disorder selected from retinitis pigmentosa, secondary pigmentary retinal degeneration, diabetic retinopathy, age related macular degeneration, a macular hole, an ocular malignancy, retinoblastoma, retinal detachment, or river blindness, comprising administering an effective amount of a compound to the human in need thereof wherein the compound is selected from the group consisting of:
- (22) 8-Bromo-(4-methyl-β-phenyl-1, $N^2$-etheno)guanosine-3', 5'-cyclic monophosphorothioate, Rp-isomer;
- (23) 8-Bromo-(3-thiophen-yl-1, $N^2$-etheno)guanosine-3', 5'-cyclic monophosphorothioate, Rp-isomer;
- (24) 8-Bromo-(2-naphthyl-1, $N^2$-etheno)guanosine-3', 5'-cyclic monophosphorothioate, Rp-isomer;
- (32) 8-Carboxymethylthio-β-phenyl-1, $N^2$-ethenoguanosine-3', 5'-cyclic monophosphorothioate, Rp-isomer;
- (33) β-Phenyl-1, $N^2$-etheno-8-phenylamidomethylthioguanosine-3', 5'-cyclic monophosphorothioate, Rp-isomer;
- (34) 8-(4-Hydroxyphenylthio)--phenyl-1, $N^2$-ethenoguanosine-3', 5'-cyclic monophosphorothioate, Rp-isomer;
- (35) 8-(4-Isopropylphenylthio)-β-phenyl-1, $N^2$-ethenoguanosine-3', 5'-cyclic monophosphorothioate, Rp-isomer;
- (36) 8-(2-Aminophenylthio)-β-phenyl-1, $N^2$-ethenoguanosine-3', 5'-cyclic monophosphorothioate, Rp-isomer;
- (37) β-Phenyl-1, $N^2$-etheno-8-thioguanosine-3', 5'-cyclic monophosphorothioate, Rp-isomer;
- (39) β-(4-Azidophenyl)-1, $N^2$-etheno-8-bromoguanosine-3', 5'-cyclic monophosphorothioate, Rp-isomer;
- (50) 8-Phenyl-β-phenyl-1, $N^2$-ethenoguanosine-3', 5'-cyclic monophosphorothioate, Rp-isomer,
- (51) 8-(4-Chlorophenyl)-β-phenyl-1, $N^2$-ethenoguanosine-3', 5'-cyclic monophosphorothioate, Rp-isomer;
- (52) 8-(4-Chlorophenylsulfoxide)guanosine-3', 5'-cyclic monophosphorothioate, Rp-isomer; and
- (54) 8-(4-Chlorophenylsulfonyl)-β-phenyl-1, $N^2$-ethenoguanosine-3', 5'-cyclic monophosphorothioate, Rp-isomer;

or a pharmaceutically acceptable salt thereof.

6. The method of claim 5, wherein the disorder is retinitis pigmentosa.

7. The method of claim 6, wherein the compound is:
8-Bromo-(4-methyl-β-phenyl-1, $N^2$-etheno)guanosine-3', 5'-cyclic monophosphorothioate, Rp-isomer;
or a pharmaceutically acceptable salt thereof.

8. The method of claim 5, wherein the disorder is secondary pigmentary retinal degeneration.

9. The method of claim 8, wherein the compound is:
8-Bromo-(4-methyl-β-phenyl-1, $N^2$-etheno)guanosine-3', 5'-cyclic monophosphorothioate, Rp-isomer;
or a pharmaceutically acceptable salt thereof.

10. The method of claim 5, wherein the disorder is diabetic retinopathy.

11. The method of claim 10, wherein the compound is:
8-Bromo-(4-methyl-β-phenyl-1, $N^2$-etheno)guanosine-3', 5'-cyclic monophosphorothioate, Rp-isomer;
or a pharmaceutically acceptable salt thereof.

12. The method of claim 5, wherein the disorder is age related macular degeneration.

13. The method of claim 12, wherein the compound is:

8-Bromo-(4-methyl-β-phenyl-1, $N^2$-etheno)guanosine-3',
5'-cyclic monophosphorothioate, Rp-isomer;

or a pharmaceutically acceptable salt thereof.

14. The method of claim 5, wherein the disorder is a macular hole.

15. The method of claim 14, wherein the compound is:

8-Bromo-(4-methyl-β-phenyl-1, $N^2$-etheno)guanosine-3',
5'-cyclic monophosphorothioate, Rp-isomer;

or a pharmaceutically acceptable salt thereof.

16. The method of claim 5, wherein the disorder is an ocular malignancy.

17. The method of claim 16, wherein the compound is:

8-Bromo-(4-methyl-β-phenyl-1, $N^2$-etheno)guanosine-3',
5'-cyclic monophosphorothioate, Rp-isomer;

or a pharmaceutically acceptable salt thereof.

18. The method of claim 5, wherein the disorder is retinoblastoa, retinal detachment, or river blindness.

19. The method of claim 18, wherein the compound is:

8-Bromo-(4-methyl-β-phenyl-1, $N^2$-etheno)guanosine-3',
5'-cyclic monophosphorothioate, Rp-isomer;

or a pharmaceutically acceptable salt thereof.

* * * * *